US007488804B2

(12) United States Patent
Saxon et al.

(10) Patent No.: US 7,488,804 B2
(45) Date of Patent: Feb. 10, 2009

(54) MODIFIED FUSION MOLECULES FOR TREATMENT OF ALLERGIC DISEASE

(75) Inventors: Andrew Saxon, Santa Monica, CA (US); Ke Zhang, Los Angeles, CA (US); Daocheng Zhu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 307 days.

(21) Appl. No.: 11/050,113

(22) Filed: Feb. 2, 2005

(65) Prior Publication Data

US 2006/0171942 A1    Aug. 3, 2006

(51) Int. Cl.
C12P 21/08    (2006.01)
(52) U.S. Cl. .............. 530/387.3; 424/133.1; 424/134.1; 424/144.1; 424/185.1; 424/192.1; 530/388.22; 530/866; 530/868
(58) Field of Classification Search ........................ None
See application file for complete search history.

(56) References Cited

U.S. PATENT DOCUMENTS

| | | | |
|---|---|---|---|
| 3,187,748 A | 6/1965 | Mitchell et al. | |
| 3,656,070 A | 4/1972 | Monaghan et al. | |
| 3,658,059 A | 4/1972 | Steil | |
| 3,814,297 A | 6/1974 | Warren | |
| 3,826,413 A | 7/1974 | Warren | |
| 4,208,479 A * | 6/1980 | Zuk et al. ..................... 435/7.9 | |
| 4,527,769 A | 7/1985 | Stogner et al. | |
| 4,592,348 A | 6/1986 | Waters, IV et al. | |
| 4,648,393 A | 3/1987 | Landis et al. | |
| 4,677,975 A | 7/1987 | Edgar et al. | |
| 4,683,195 A | 7/1987 | Mullis et al. | |
| 4,790,305 A | 12/1988 | Zoltan et al. | |
| 4,803,978 A | 2/1989 | Johnson et al. | |
| 4,896,832 A | 1/1990 | Howlett | |
| 4,922,901 A | 5/1990 | Brooks et al. | |
| 4,926,852 A | 5/1990 | Zoltan et al. | |
| 4,943,529 A | 7/1990 | Van Den Berg et al. | |
| 5,329,028 A | 7/1994 | Ashkenazi et al. | |
| 2003/0082190 A1 * | 5/2003 | Saxon et al. ............. 424/178.1 | |
| 2004/0198961 A1 | 10/2004 | An et al. | |

FOREIGN PATENT DOCUMENTS

| | | |
|---|---|---|
| WO | WO 98/09344 | 3/1988 |
| WO | WO 92/09300 A1 | 11/1991 |
| WO | WO 02/088317 | 11/2002 |
| WO | WO 02/102320 A2 | 12/2002 |
| WO | WO 02102320 A2 * | 12/2002 |

OTHER PUBLICATIONS

Zhu et al., Nature Medicine, 2002, 8:518-521.*
Adamczewski, M., Chemical Immun., 59:173-190 1994.
Adelman et al., *DNA* 2:183 1983.
Altschul et al., "Gapped BLAST and PSI-BLAST: A New generation of protein database search programs", 25:3389-3402, (1997).
Ashman et al., J. Immunol, 157:5-11 1996.
Ballance et al., Biochem. Biophys. Res. Commun., 112:284-289 1983.
Barnes, The New England Journal of Medicine, 341:2006-2008 1999.
Beach and Nurse, Nature 290:140 1981.
Beasley et al., J. Allergy Clin. Immunol., 105:466-472 2000.
Benoist and Mathis, Arthritis Res. vol. 2:90-94 2000.
Blom et al., Eur J Immunol., 22, 2025-32 1992.
Blom et al., Scand J Immunol., 44, 54-61 1996.
Blondel et al, Protein Engineering, 4:457-461 1991.
Botstein et al., Science 229:1193 1985.
Brake et al., Proc. Natl. Acad. Sci., 81:4642-4646 1984.
Cambier et al, Proc. Natl. Acad. Sci. 94:5993-5995 1997.
Carter et al., Nucl. Acids Res., 13:4331 1986.
Chan et al., Immunology, 21:967-981 1971.
Daeron et al., Immunity, 3:635-646 1995.
Daeron et al., J. Clin. Invest., 95:577-85 1995.
Daeron et al, Annu. Rev. Immunol., 5:203-234 1997.
Delespesse et al., Immunol. Rev. 125:77-97 1992.
Dombrowicz et al., Journal of Immunology 157, 1645-1651. 1996.
Ellison et al., DNA 1:11-18 1982.
Ellison et al., Nucl. Acid Res. 10:4071-4079 1982.
Ellison et al., Proc. Nat. Acad. Sci. 79:1984-1988 1982.
Fiebiger et al., J. Clin. Invest. 96:2606-12 1995.
Fiebiger et al., J. Clin. Invest. 101:243-251, (1998).
Fridman, W., FASEB J, 5(12):2684-90 1991.
G. Barany and R. B. Merrifield, The Peptide: Analysis Synthesis, Biology, editors E. Gross and J. Meienhofer, vol. 2, Academic Press, New York, (1980), pp. 3-254.
Gollnick et al., J. Immunol. 144:1974-82 1990.
Graham et al, J. Gen. Virol. 36:59 1977.
Hellman, Eur. J. Immunol. 23:159-167 1992.
Helm et al., J. Cell Biol. 271(13):7494-7500 1996.
Hide et al., N. Engl. J. Med. 328:1599-1604 1993.
Ji, T.H. "Bifunctional Reagents", Meth. Enzymol. 91:580-609, (1983).
Kaplan, A. P., Urticaria and Angioedema, In: *Inflammation: Basic Principles and Clinical Correlates* (Galliin and Snyderman eds.), 3rd Edition, Lippincott & Wilkins, Philadelphia, 1999, pp. 915-928.
Kelly and Hynes, EMBO J. 4:475-479 1985.
Kikutani et al., Cell 47:657-665 1986.

(Continued)

*Primary Examiner*—Michael Szperka
(74) *Attorney, Agent, or Firm*—James A. Fox; Ginger R. Dreger; Goodwin Procter LLP

(57) ABSTRACT

The present invention comprises a fusion molecule comprising a Fcε fragment sequence including functionally active CH2, CH3 and CH4 domains of the constant region of an IgE heavy chain (CHε2-CHε3-CHε4 sequence) linked at its C-terminus to the N-terminus of a second polypeptide including functionally active hinge, CH2 and CH3 domains of the constant region of an IgG₁ heavy chain (γhinge-CHγ2-CHγ3 sequence), pharmaceutical compositions comprising the fusion molecule and methods of treatment using the fusion molecule.

1 Claim, 19 Drawing Sheets

OTHER PUBLICATIONS

Kinet, J. P., Annu. Rev. Immunol., 17:931-972 1999.
Kondo et al., Int. Arch. Allergy Immunol., 105:38-48 1994.
Krawinkel et al., EMBO J. 1:403-407 1982.
Kunkel et al., Methods Enzymol. 154:367-82 1987.
Landschulz, W. H., et al. Science 240:1759-1764 1988.
Ludin et al., *EMBO J.* 6:109-114 1987.
Ma et al., J Allergy Clin. Immunol., 112:784-8 2003.
Malbec and Fridman, Curr. Top. Microbiol. Immunol., 244:13-27 1999.
Max et al., Cell 29:691-699 1982.
McKnight, S. L., Scientific American 54-64, 1991.
Metcalfe et al., Physiol. Rev., 77:1033-1079 1997.
O'Shea, E. K. et al., Science 243: 38-542 1989.
Ott and Cambier, J. Allergy Clin. Immunol., 106(3):429-440 2000.
Peat and Li, J. Allergy Clin. Immunol., 103:1-10 1999.
Peng et al., J. Immunol., 148:129-136 1992.
Phillips and Parker, J. Immunol., 132:627-632 1984.
Presta et al., J. Biol. Chem., 269:26368-26373 1994.
Rattan et al., Ann. N.Y Acad. Sci. 663:48-62 1992.
Roitt et al., Immunology, Fifth Edition, , eds., pp. 302-317, 1998.
Saxon et al., Current Opinion in Allergy & Clinical Immunology 4, 563-568, 2004.
Saxon et al., J. Immunol., 147:4000 1991.
Schmidt-Dorr. T. et al., Biochemistry 30:9657-9664 1991.
Seifter et al., "Analysis for protein modifications and nonprotein cofactors," Meth. Enzymol., 182:626-646 1990.
Shields et al., J Biol. Chem., 276, 6591-604 2001.
Sreekrishna et al., J. Basic Microbiol. 28:165-278 1988.
Takahashi et al., Cell 29:671-679 1982.
Tunon de Lara, Rev. Mal. Respir., 13(1):27-36 1996.
Urlaub and Chasin, Proc. Natl. Acad. Sci., 77:4216 1980.
Wang and Hanson, "Parenteral Formulations of Proteins and Peptides: Stability and Stablizers", Journal of Parenteral Science and Technology, Technical Report No. 10, Supp. 42-2S, (1998).
Watson et al., Vet. Immunol. Immunopathol. 73:323-9 2000.
Wells et al., Gene 34:315 1985.
Wells et al., Philos. Trans. R. Soc. London SerA, 317:415 1986.
Wetmur et al., J. Mol. Biol. 31:349-70 1966.
Wetmur et al, Critical Reviews in Biochemistry and Molecular Biology, 26(34):227-59 1991.
Wines et al., J. Immunol., 164(10):5313-5318 2000.
Wold, F., "Posttranslational Protein Modifications: Perspectives and Prospects," in Posttranslational Covalent Modification of Proteins, Johnson, B. C., ed., Academic Press, New York, pp. 1-12, 1981.
Yodoi et al., Ciba Found. Symp., 147:133-148 1989.
Zhang K. et al., J. Allergy Clin. Imm., 114, pp. 321-327 2004.
Zhang et al., J. Exp. Med. 176:233-243 1992.
Zhu D. et al., Nat Med 8, 518-21 2002.
Zoller & Smith, DNA 3:479-488 1984.
Zoller et al., Methods Enzymol., 100:468-500 1983.
Zoller et al., Nucl. Acids Res., 10:6487 1987.

* cited by examiner

FIGURE 1

```
gagcccaaat cttgtgacaa aactcacaca tgcccaccgt gcccagcacc tgaactcctg  60
gggggaccgt cagtcttcct cttcccccca aacccaagg acaccctcat gatctcccgg  120
acccctgagg tcacatgcgt ggtggtggac gtgagccacg aagaccctga ggtcaagttc  180
aactggtacg tggacggcgt ggaggtgcat aatgttaaga caaagccgcg ggaggagcag  240
tacaacagca cgtaccgtgt ggtcagcgtc ctcaccgtcc tgcaccagaa ctggatgaat  300
ggaaaggagt acaagtgcaa ggtctccaac aaagccctcc cagcccccat cgagaaaacc  360
atctccaaag ccaaagtgca gccccgagaa ccacaggtgt acaccctgcc cccatcccgg  420
gatgagctga ccaagaacca ggtcagcctg acctgcctgg tcaaaggctt ctatcccagc  480
gacatcgccg tggagtggga gagcaatggg cagccggaga caactacaa gaccacgcct  540
cccgtgctgg actccgtcgg ctccttcttc ctctacagca agctcaccgt ggacaagagc  600
aggtggcagc aggggaacgt cttctcatgc tccgtgatgc atgaggctct gcacaaccac  660
taccagcaga ggagcctctc cctgtctccg ggtaaa                            696
```

FIGURE 2

```
Ala Ser Thr Lys Gly Pro Ser Val Phe Pro Leu Ala Pro Ser Ser Lys
Ser Thr Ser Gly Gly Thr Ala Ala Leu Gly Cys Leu Val Lys Asp Tyr
Phe Pro Glu Pro Val Thr Val Ser Trp Asn Ser Gly Ala Leu Thr Ser
Gly Val His Thr Phe Pro Ala Val Leu Gln Ser Ser Gly Leu Tyr Ser
Leu Ser Ser Val Val Thr Val Pro Ser Ser Ser Leu Gly Thr Gln Thr
Tyr Ile Cys Asn Val Asn His Lys Pro Ser Asn Thr Lys Val Asp Lys
Lys Val Glu Pro Lys Ser Cys Asp Lys Thr His Thr Cys Pro Pro Cys
Pro Ala Pro Glu Leu Leu Gly Gly Pro Ser Val Phe Leu Phe Pro Pro
Lys Pro Lys Asp Thr Leu Met Ile Ser Arg Thr Pro Glu Val Thr Cys
Val Val Val Asp Val Ser His Glu Asp Pro Glu Val Lys Phe Asn Trp
Tyr Val Asp Gly Val Glu Val His Asn Val Lys Thr Lys Pro Arg Glu
Glu Gln Tyr Asn Ser Thr Tyr Arg Val Val Ser Val Leu Thr Val Leu
His Gln Asn Trp Met Asn Gly Lys Glu Tyr Lys Cys Lys Val Ser Asn
Lys Ala Leu Pro Ala Pro Ile Glu Lys Thr Ile Ser Lys Ala Lys Val
Gln Pro Arg Glu Pro Gln Val Tyr Thr Leu Pro Pro Ser Arg Asp Glu
Leu Thr Lys Asn Gln Val Ser Leu Thr Cys Leu Val Lys Gly Phe Tyr
Pro Ser Asp Ile Ala Val Glu Trp Glu Ser Asn Gly Gln Pro Glu Asn
Asn Tyr Lys Thr Thr Pro Pro Val Leu Asp Ser Val Gly Ser Phe Phe
Leu Tyr Ser Lys Leu Thr Val Asp Lys Ser Arg Trp Gln Gln Gly Asn
Val Phe Ser Cys Ser Val Met His Glu Ala Leu His Asn His Tyr Gln
Gln Arg Ser Leu Ser Leu Ser Pro Gly Lys
```

FIGURE 3

```
Glu Pro Lys Ser Cys Asp Lys Thr His Thr Cys Pro Pro Cys Pro Ala
Pro Glu Leu Leu Gly Gly Pro Ser Val Phe Leu Phe Pro Pro Lys Pro
Lys Asp Thr Leu Met Ile Ser Arg Thr Pro Glu Val Thr Cys Val Val
Val Asp Val Ser His Glu Asp Pro Glu Val Lys Phe Asn Trp Tyr Val
Asp Gly Val Glu Val His Asn Val Lys Thr Lys Pro Arg Glu Glu Gln
Tyr Asn Ser Thr Tyr Arg Val Val Ser Val Leu Thr Val Leu His Gln
Asn Trp Met Asn Gly Lys Glu Tyr Lys Cys Lys Val Ser Asn Lys Ala
Leu Pro Ala Pro Ile Glu Lys Thr Ile Ser Lys Ala Lys Val Gln Pro
Arg Glu Pro Gln Val Tyr Thr Leu Pro Pro Ser Arg Asp Glu Leu Thr
Lys Asn Gln Val Ser Leu Thr Cys Leu Val Lys Gly Phe Tyr Pro Ser
Asp Ile Ala Val Glu Trp Glu Ser Asn Gly Gln Pro Glu Asn Asn Tyr
Lys Thr Thr Pro Pro Val Leu Asp Ser Val Gly Ser Phe Phe Leu Tyr
Ser Lys Leu Thr Val Asp Lys Ser Arg Trp Gln Gln Gly Asn Val Phe
Ser Cys Ser Val Met His Glu Ala Leu His Asn His Tyr Gln Gln Arg
Ser Leu Ser Leu Ser Pro Gly Lys
```

FIGURE 4

```
tccacacaga gcccatccgt cttccccttg acccgctgct gcaaaaacat tccctccaat  60
gccacctccg tgactctggg ctgcctggcc acgggctact tcccggagcc ggtgatggtg  120
acctgggaca caggctccct caacgggaca actatgacct taccagccac caccctcacg  180
ctctctggtc actatgccac catcagcttg ctgaccgtct cgggtgcgtg ggccaagcag  240
atgttcacct gccgtgtggc acacactcca tcgtccacag actgggtcga caacaaaacc  300
ttcagcgtct gctccaggga cttcacaccg cccaccgtga agatcttaca gtcgtcctgc  360
gacggcggcg ggcacttccc cccgaccatc cagctcctgt gcctcgtctc tgggtacacc  420
ccagggacta tcaacatcac ctggctggag gacgggcagg tcatggacgt ggacttgtcc  480
accgcctcta ccacgcagga gggtgagctg gcctccacac aaagcgagct caccctcagc  540
cagaagcact ggctgtcaga ccgcacctac acctgccagg tcacctatca aggtcacacc  600
tttgaggaca gcaccaagaa gtgtgcagat tccaacccga gaggggtgag cgcctaccta  660
agccggccca gcccgttcga cctgttcatc cgcaagtcgc cacgatcac ctgtctggtg  720
gtggacctgg cacccagcaa ggggaccgtg aacctgacct ggtcccgggc cagtgggaag  780
cctgtgaacc actccaccag aaaggaggag aagcagcgca atggcacgtt aaccgtcacg  840
tccaccctgc cggtgggcac ccgagactgg atcgaggggg agacctacca gtgcagggtg  900
acccaccccc acctgcccag ggccctcatg cggtccacga ccaagaccag cggcccgcgt  960
gctgccccgg aagtctatgc gtttgcgacg ccggagtggc cggggagccg ggacaagcgc 1020
accctcgcct gcctgatcca gaacttcatg cctgaggaca tctcggtgca gtggctgcac 1080
aacgaggtgc agctcccgga cgcccggcac agcacgacgc agccccgcaa gaccaagggc 1140
tccggcttct tcgtcttcag ccgcctggag gtgaccaggg ccgaatggga gcagaaagat 1200
gagttcatct gccgtgcagt ccatgaggca gcgagcccct cacagaccgt ccagcgagcg 1260
gtgtctgtaa atccggtaa atgacgtact cctgcctccc tccctcccag ggctccatcc 1320
agctgtgcag tggggaggac tggccagacc ttctgtccac tgttgcaatg accccaggaa 1380
gctaccccca ataaactgtg cctgctcaga gccccagtac accattctt gggagcgggc 1440
agggc                                                              1445
```

FIGURE 5

```
Ser Thr Gln Ser Pro Ser Val Phe Pro Leu Thr Arg Cys Cys Lys Asn
Ile Pro Ser Asn Ala Thr Ser Val Thr Leu Gly Cys Leu Ala Thr Gly
Tyr Phe Pro Glu Pro Val Met Val Thr Trp Asp Thr Gly Ser Leu Asn
Gly Thr Thr Met Thr Leu Pro Ala Thr Thr Leu Thr Leu Ser Gly His
Tyr Ala Thr Ile Ser Leu Leu Thr Val Ser Gly Ala Trp Ala Lys Gln
Met Phe Thr Cys Arg Val Ala His Thr Pro Ser Ser Thr Asp Trp Val
Asp Asn Lys Thr Phe Ser Val Cys Ser Arg Asp Phe Thr Pro Pro Thr
Val Lys Ile Leu Gln Ser Ser Cys Asp Gly Gly Gly His Phe Pro Pro
Thr Ile Gln Leu Leu Cys Leu Val Ser Gly Tyr Thr Pro Gly Thr Ile
Asn Ile Thr Trp Leu Glu Asp Gly Gln Val Met Asp Val Asp Leu Ser
Thr Ala Ser Thr Thr Gln Glu Gly Glu Leu Ala Ser Thr Gln Ser Glu
Leu Thr Leu Ser Gln Lys His Trp Leu Ser Asp Arg Thr Tyr Thr Cys
Gln Val Thr Tyr Gln Gly His Thr Phe Glu Asp Ser Thr Lys Lys Cys
Ala Asp Ser Asn Pro Arg Gly Val Ser Ala Tyr Leu Ser Arg Pro Ser
Pro Phe Asp Leu Phe Ile Arg Lys Ser Pro Thr Ile Thr Cys Leu Val
Val Asp Leu Ala Pro Ser Lys Gly Thr Val Asn Leu Thr Trp Ser Arg
Ala Ser Gly Lys Pro Val Asn His Ser Thr Arg Lys Glu Glu Lys Gln
Arg Asn Gly Thr Leu Thr Val Thr Ser Thr Leu Pro Val Gly Thr Arg
Asp Trp Ile Glu Gly Glu Thr Tyr Gln Cys Arg Val Thr His Pro His
Leu Pro Arg Ala Leu Met Arg Ser Thr Thr Lys Thr Ser Gly Pro Arg
Ala Ala Pro Glu Val Tyr Ala Phe Ala Thr Pro Glu Trp Pro Gly Ser
Arg Asp Lys Arg Thr Leu Ala Cys Leu Ile Gln Asn Phe Met Pro Glu
Asp Ile Ser Val Gln Trp Leu His Asn Glu Val Gln Leu Pro Asp Ala
Arg His Ser Thr Thr Gln Pro Arg Lys Thr Lys Gly Ser Gly Phe Phe
Val Phe Ser Arg Leu Glu Val Thr Arg Ala Glu Trp Glu Gln Lys Asp
Glu Phe Ile Cys Arg Ala Val His Glu Ala Ala Ser Pro Ser Gln Thr
Val Gln Arg Ala Val Ser Val Asn Pro Gly Lys
```

FIGURE 6

```
Phe Thr Pro Pro Thr Val Lys Ile Leu Gln Ser Ser Cys Asp Gly Gly
Gly His Phe Pro Pro Thr Ile Gln Leu Leu Cys Leu Val Ser Gly Tyr
Thr Pro Gly Thr Ile Asn Ile Thr Trp Leu Glu Asp Gly Gln Val Met
Asp Val Asp Leu Ser Thr Ala Ser Thr Thr Gln Glu Gly Glu Leu Ala
Ser Thr Gln Ser Glu Leu Thr Leu Ser Gln Lys His Trp Leu Ser Asp
Arg Thr Tyr Thr Cys Gln Val Thr Tyr Gln Gly His Thr Phe Glu Asp
Ser Thr Lys Lys Cys Ala Asp Ser Asn Pro Arg Gly Val Ser Ala Tyr
Leu Ser Arg Pro Ser Pro Phe Asp Leu Phe Ile Arg Lys Ser Pro Thr
Ile Thr Cys Leu Val Val Asp Leu Ala Pro Ser Lys Gly Thr Val Asn
Leu Thr Trp Ser Arg Ala Ser Gly Lys Pro Val Asn His Ser Thr Arg
Lys Glu Glu Lys Gln Arg Asn Gly Thr Leu Thr Val Thr Ser Thr Leu
Pro Val Gly Thr Arg Asp Trp Ile Glu Gly Glu Thr Tyr Gln Cys Arg
Val Thr His Pro His Leu Pro Arg Ala Leu Met Arg Ser Thr Thr Lys
Thr Ser Gly Pro Arg Ala Ala Pro Glu Val Tyr Ala Phe Ala Thr Pro
Glu Trp Pro Gly Ser Arg Asp Lys Arg Thr Leu Ala Cys Leu Ile Gln
Asn Phe Met Pro Glu Asp Ile Ser Val Gln Trp Leu His Asn Glu Val
Gln Leu Pro Asp Ala Arg His Ser Thr Thr Gln Pro Arg Lys Thr Lys
Gly Ser Gly Phe Phe Val Phe Ser Arg Leu Glu Val Thr Arg Ala Glu
Trp Glu Gln Lys Asp Glu Phe Ile Cys Arg Ala Val His Glu Ala Ala
Ser Pro Ser Gln Thr Val Gln Arg Ala Val Ser Val Asn Pro Gly Lys
```

FIGURE 7A: GE2 DNA and Protein Sequence

```
DNA      1 TATCCATATGATGTTCCAGATTATGCTGGGGCCCAGCCGGCCAGATCTGAGCCCAAATCT    60
Protein1   Y  P  Y  D  V  P  D  Y  A  G  A  Q  P  A  R  S  E  P  K  S    20

61 TGTGACAAAACTCACACATGCCCACCGTGCCCAGCACCTGAACTCCTGGGGGGACCGTCA   120
        21 C  D  K  T  H  T  C  P  P  C  P  A  P  E  L  L  G  G  P  S    40

121 GTCTTCCTCTTCCCCCCAAAACCCAAGGACACCCTCATGATCTCCCGGACCCCTGAGGTC   180
        41 V  F  L  F  P  P  K  P  K  D  T  L  M  I  S  R  T  P  E  V    60

181 ACATGCGTGGTGGTGGACGTGAGCCACGAAGACCCTGAGGTCAAGTTCAACTGGTACGTG   240
        61 T  C  V  V  V  D  V  S  H  E  D  P  E  V  K  F  N  W  Y  V    80

241 GACGGCGTGGAGGTGCATAATGCCAAGACAAAGCCGCGGGAGGAGCAGTACAACAGCACG   300
        81 D  G  V  E  V  H  N  A  K  T  K  P  R  E  E  Q  Y  N  S  T   100

301 TACCGGGTGGTCAGCGTCCTCACCGTCCTGCACCAGGACTGGCTGAATGGCAAGGAGTAC   360
       101 Y  R  V  V  S  V  L  T  V  L  H  Q  D  W  L  N  G  K  E  Y   120

361 AAGTGCAAGGTCTCCAACAAAGCCCTCCCAGCCCCCATCGAGAAAACCATCTCCAAAGCC   420
       121 K  C  K  V  S  N  K  A  L  P  A  P  I  E  K  T  I  S  K  A   140

421 AAAGGGCAGCCCCGAGAACCACAGGTGTACACCCTGCCCCCATCCCGGGATGAGCTGACC   480
       141 K  G  Q  P  R  E  P  Q  V  Y  T  L  P  P  S  R  D  E  L  T   160

481 AAGAACCAGGTCAGCCTGACCTGCCTGGTCAAAGGCTTCTATCCCAGCGACATCGCCGTG   540
       161 K  N  Q  V  S  L  T  C  L  V  K  G  F  Y  P  S  D  I  A  V   180

541 GAGTGGGAGAGCAATGGGCAGCCGGAGAACAACTACAAGACCACGCCTCCCGTGCTGGAC   600
       181 E  W  E  S  N  G  Q  P  E  N  N  Y  K  T  T  P  P  V  L  D   200

601 TCCGACGGCTCCTTCTTCCTCTACAGCAAGCTCACCGTGGACAAGAGCAGGTGGCAGCAG   660
       201 S  D  G  S  F  F  L  Y  S  K  L  T  V  D  K  S  R  W  Q  Q   220

661 GGGAACGTCTTCTCATGCTCCGTGATGCATGAGGCTCTGCACAACCACTACACGCAGAAG   720
       221 G  N  V  F  S  C  S  V  M  H  E  A  L  H  N  H  Y  T  Q  K   240

721 AGCCTCTCCCTGTCTCCGGGTAAAGTCGAGGGTGGAGGCGGTTCAGGCGGAGGTGGCTCT   780
       241 S  L  S  L  S  P  G  K  V  E  G  G  G  S  G  G  G  G  S   260

781 GGCGGTGGCGGATCGTTCACCCCGCCCACCGTGAAGATCTTACAGTCGTCCTGCGACGGC   840
       261 G  G  G  G  S  F  T  P  P  T  V  K  I  L  Q  S  S  C  D  G   280

841 GGCGGGCACTTCCCCCCGACCATCCAGCTCCTGTGCCTCGTCTCTGGGTACACCCCAGGG   900
       281 G  G  H  F  P  P  T  I  Q  L  L  C  L  V  S  G  Y  T  P  G   300

901 ACTATCAACATCACCTGGCTGGAGGACGGGCAGGTCATGGACGTGGACTTGTCCACCGCC   960
       301 T  I  N  I  T  W  L  E  D  G  Q  V  M  D  V  D  L  S  T  A   320

961 TCTACCACGCAGGAGGGTGAGCTGGCCTCCACACAAAGCGAGCTCACCCTCAGCCAGAAG  1020
       321 S  T  T  Q  E  G  E  L  A  S  T  Q  S  E  L  T  L  S  Q  K   340
```

FIGURE 7B: GE2 DNA and Protein Sequence

```
1021 CACTGGCTGTCAGACCGCACCTACACCTGCCAGGTCACCTATCAAGGTCACACCTTTGAG 1080
 341  H   W   L   S   D   R   T   Y   T   C   Q   V   T   Y   Q   G   H   T   F   E   360

1081 GACAGCACCAAGAAGTGTGCAGATTCCAACCCGAGAGGGGTGAGCGCCTACCTAAGCCGG 1140
 361  D   S   T   K   K   C   A   D   S   N   P   R   G   V   S   A   Y   L   S   R   380

1141 CCCAGCCCGTTCGACCTGTTCATCCGCAAGTCGCCCACGATCACCTGTCTGGTGGTGGAC 1200
 381  P   S   P   F   D   L   F   I   R   K   S   P   T   I   T   C   L   V   V   D   400

1201 CTGGCACCCAGCAAGGGGACCGTGAACCTGACCTGGTCCCGGGCCAGTGGGAAGCCTGTG 1260
 401  L   A   P   S   K   G   T   V   N   L   T   W   S   R   A   S   G   K   P   V   420

1261 AACCACTCCACCAGAAAGGAGGAGAAGCAGCGCAATGGCACGTTAACCGTCACGTCCACC 1320
 421  N   H   S   T   R   K   E   E   K   Q   R   N   G   T   L   T   V   T   S   T   440

1321 CTGCCGGTGGGCACCCGAGACTGGATCGAGGGGGAGACCTACCAGTGCAGGGTGACCCAC 1380
 441  L   P   V   G   T   R   D   W   I   E   G   E   T   Y   Q   C   R   V   T   H   460

1381 CCCCACCTGCCCAGGGCCCTCATGCGGTCCACGACCAAGACCAGCGGCCCGCGTGCTGCC 1440
 461  P   H   L   P   R   A   L   M   R   S   T   T   K   T   S   G   P   R   A   A   480

1441 CCGGAAGTCTATGCGTTTGCGACGCCGGAGTGGCCGGGGAGCCGGGACAAGCGCACCCTC 1500
 481  P   E   V   Y   A   F   A   T   P   E   W   P   G   S   R   D   K   R   T   L   500

1501 GCCTGCCTGATCCAGAACTTCATGCCTGAGGACATCTCGGTGCAGTGGCTGCACAACGAG 1560
 501  A   C   L   I   Q   N   F   M   P   E   D   I   S   V   Q   W   L   H   N   E   520

1561 GTGCAGCTCCCGGACGCCCGGCACAGCACGACGCAGCCCCGCAAGACCAAGGGCTCCGGC 1620
 521  V   Q   L   P   D   A   R   H   S   T   T   Q   P   R   K   T   K   G   S   G   540

1621 TTCTTCGTCTTCAGCCGTCTAGAGGTGACCAGGGCCGAATGGGAGCAGAAAGATGAGTTC 1680
 541  F   F   V   F   S   R   L   E   V   T   R   A   E   W   E   Q   K   D   E   F   560

1681 ATCTGCCGTGCAGTCCATGAGGCAGCTAGCCCCTCACAGACCGTCCAGCGAGCGGTGTCT 1740
 561  I   C   R   A   V   H   E   A   A   S   P   S   Q   T   V   Q   R   A   V   S   580

1741 GTAAATCCCGGTAAATGA                                           1758
 581  V   N   P   G   K   *                                       586
```

FIGURE 8A: E2G DNA and Protein Sequence

```
DNA        1  TTCACCCCGCCCACCGTGAAGATCTTACAGTCGTCCTGCGACGGCGGCGGGCACTTCCCC    60
Protein1      F   T   P   P   T   V   K   I   L   Q   S   S   C   D   G   G   H   F   P      20

61  CCGACCATCCAGCTCCTGTGCCTCGTCTCTGGGTACACCCCAGGGACTATCAACATCACC   120
          21  P   T   I   Q   L   L   C   L   V   S   G   Y   T   P   G   T   I   N   I   T      40

121  TGGCTGGAGGACGGGCAGGTCATGGACGTGGACTTGTCCACCGCCTCTACCACGCAGGAG   180
          41  W   L   E   D   G   Q   V   M   D   V   D   L   S   T   A   S   T   T   Q   E      60

181  GGTGAGCTGGCCTCCACACAAAGCGAGCTCACCCTCAGCCAGAAGCACTGGCTGTCAGAC   240
          61  G   E   L   A   S   T   Q   S   E   L   T   L   S   Q   K   H   W   L   S   D      80

241  CGCACCTACACCTGCCAGGTCACCTATCAAGGTCACACCTTTGAGGACAGCACCAAGAAG   300
          81  R   T   Y   T   C   Q   V   T   Y   Q   G   H   T   F   E   D   S   T   K   K     100

301  TGTGCAGATTCCAACCCGAGAGGGGTGAGCGCCTACCTAAGCCGGCCCAGCCCGTTCGAC   360
         101  C   A   D   S   N   P   R   G   V   S   A   Y   L   S   R   P   S   P   F   D     120

361  CTGTTCATCCGCAAGTCGCCCACGATCACCTGTCTGGTGGTGGACCTGGCACCCAGCAAG   420
         121  L   F   I   R   K   S   P   T   I   T   C   L   V   V   D   L   A   P   S   K     140

421  GGGACCGTGAACCTGACCTGGTCCCGGGCCAGTGGGAAGCCTGTGAACCACTCCACCAGA   480
         141  G   T   V   N   L   T   W   S   R   A   S   G   K   P   V   N   H   S   T   R     160

481  AAGGAGGAGAAGCAGCGCAATGGCACGTTAACCGTCACGTCCACCCTGCCGGTGGGCACC   540
         161  K   E   E   K   Q   R   N   G   T   L   T   V   T   S   T   L   P   V   G   T     180

541  CGAGACTGGATCGAGGGGGAGACCTACCAGTGCAGGGTGACCCACCCCCACCTGCCCAGG   600
         181  R   D   W   I   E   G   E   T   Y   Q   C   R   V   T   H   P   H   L   P   R     200

601  GCCCTCATGCGGTCCACGACCAAGACCAGCGGCCCGCGTGCTGCCCCGGAAGTCTATGCG   660
         201  A   L   M   R   S   T   T   K   T   S   G   P   R   A   A   P   E   V   Y   A     220

661  TTTGCGACGCCGGAGTGGCCGGGGAGCCGGGACAAGCGCACCCTCGCCTGCCTGATCCAG   720
         221  F   A   T   P   E   W   P   G   S   R   D   K   R   T   L   A   C   L   I   Q     240

721  AACTTCATGCCTGAGGACATCTCGGTGCAGTGGCTGCACAACGAGGTGCAGCTCCCGGAC   780
         241  N   F   M   P   E   D   I   S   V   Q   W   L   H   N   E   V   Q   L   P   D     260

781  GCCCGGCACAGCACGACGCAGCCCCGCAAGACCAAGGGCTCCGGCTTCTTCGTCTTCAGC   840
         261  A   R   H   S   T   T   Q   P   R   K   T   K   G   S   G   F   F   V   F   S     280

841  CGTCTAGAGGTGACCAGGGCCGAATGGGAGCAGAAAGATGAGTTCATCTGCCGTGCAGTC   900
         281  R   L   E   V   T   R   A   E   W   E   Q   K   D   E   F   I   C   R   A   V     300

901  CATGAGGCAGCTAGCCCCTCACAGACCGTCCAGCGAGCGGTGTCTGTAAATCCCGGTAAA   960
         301  H   E   A   A   S   P   S   Q   T   V   Q   R   A   V   S   V   N   P   G   K     320

961  AGATCTGAGCCCAAATCTTGTGACAAAACTCACACATGCCCACCGTGCCCAGCACCTGAA  1020
         321  R   S   E   P   K   S   C   D   K   T   H   T   C   P   P   C   P   A   P   E     340

1021  CTCCTGGGGGGACCGTCAGTCTTCCTCTTCCCCCCAAAACCCAAGGACACCCTCATGATC  1080
         341  L   L   G   G   P   S   V   F   L   F   P   P   K   P   K   D   T   L   M   I     360
```

FIGURE 8B: E2G DNA and Protein Sequence

```
1081 TCCCGGACCCCTGAGGTCACATGCGTGGTGGTGGACGTGAGCCACGAAGACCCTGAGGTC  1140
 361  S  R  T  P  E  V  T  C  V  V  V  D  V  S  H  E  D  P  E  V   380

1141 AAGTTCAACTGGTACGTGGACGGCGTGGAGGTGCATAATGCCAAGACAAAGCCGCGGGAG  1200
 381  K  F  N  W  Y  V  D  G  V  E  V  H  N  A  K  T  K  P  R  E   400

1201 GAGCAGTACAACAGCACGTACCGGGTGGTCAGCGTCCTCACCGTCCTGCACCAGGACTGG  1260
 401  E  Q  Y  N  S  T  Y  R  V  V  S  V  L  T  V  L  H  Q  D  W   420

1261 CTGAATGGCAAGGAGTACAAGTGCAAGGTCTCCAACAAAGCCCTCCCAGCCCCCATCGAG  1320
 421  L  N  G  K  E  Y  K  C  K  V  S  N  K  A  L  P  A  P  I  E   440

1321 AAAACCATCTCCAAAGCCAAAGGGCAGCCCCGAGAACCACAGGTGTACACCCTGCCCCCA  1380
 441  K  T  I  S  K  A  K  G  Q  P  R  E  P  Q  V  Y  T  L  P  P   460

1381 TCCCGGGATGAGCTGACCAAGAACCAGGTCAGCCTGACCTGCCTGGTCAAAGGCTTCTAT  1440
 461  S  R  D  E  L  T  K  N  Q  V  S  L  T  C  L  V  K  G  F  Y   480

1441 CCCAGCGACATCGCCGTGGAGTGGGAGAGCAATGGGCAGCCGGAGAACAACTACAAGACC  1500
 481  P  S  D  I  A  V  E  W  E  S  N  G  Q  P  E  N  N  Y  K  T   500

1501 ACGCCTCCCGTGCTGGACTCCGACGGCTCCTTCTTCCTCTACAGCAAGCTCACCGTGGAC  1560
 501  T  P  P  V  L  D  S  D  G  S  F  F  L  Y  S  K  L  T  V  D   520

1561 AAGAGCAGGTGGCAGCAGGGGAACGTCTTCTCATGCTCCGTGATGCATGAGGCTCTGCAC  1620
 521  K  S  R  W  Q  Q  G  N  V  F  S  C  S  V  M  H  E  A  L  H   540

1621 AACCACTACACGCAGAAGAGCCTCTCCCTGTCTCCGGGTAAATGA                 1662
 541  N  H  Y  T  Q  K  S  L  S  L  S  P  G  K  *                  554
```

FIGURE 9A: GE2 S mutant DNA and Protein Sequence

```
DNA      1  TATCCATATGATGTTCCAGATTATGCTGGGGCCCAGCCGGCCAGATCTGAGCCCAAATCT      60
Protein1    Y  P  Y  D  V  P  D  Y  A  G  A  Q  P  A  R  S  E  P  K  S    20

61  TGTGACAAAACTCACACATGCCCACCGTGCCCAGCACCTGAACTCCTGGGGGGACCGTCA    120
        21  C  D  K  T  H  T  C  P  P  C  P  A  P  E  L  L  G  G  P  S    40

121  GTCTTCCTCTTCCCCCCAAAACCCAAGGACACCCTCATGATCTCCCGGACCCCTGAGGTC    180
        41  V  F  L  F  P  P  K  P  K  D  T  L  M  I  S  R  T  P  E  V    60

181  ACATGCGTGGTGGTGGACGTGGCACACGAAGACCCTGAGGTCAAGTTCAACTGGTACGTG    240
        61  T  C  V  V  V  D  V  A  H  E  D  P  E  V  K  F  N  W  Y  V    80

241  GACGGCGTGGAGGTGCATAATGCCAAGACAAAGCCGCGGGAGGAGCAGTACAACAGCACG    300
        81  D  G  V  E  V  H  N  A  K  T  K  P  R  E  E  Q  Y  N  S  T   100

301  TACCGGGTGGTCAGCGTCCTCACCGTCCTGCACCAGGACTGGCTGAATGGCAAGGAGTAC    360
       101  Y  R  V  V  S  V  L  T  V  L  H  Q  D  W  L  N  G  K  E  Y   120

361  AAGTGCAAGGTCTCCAACAAAGCCCTCCCAGCCCCCATCGAGAAAACCATCTCCAAAGCC    420
       121  K  C  K  V  S  N  K  A  L  P  A  P  I  E  K  T  I  S  K  A   140

421  AAAGGGCAGCCCCGAGAACCACAGGTGTACACCCTGCCCCCATCCCGGGATGAGCTGACC    480
       141  K  G  Q  P  R  E  P  Q  V  Y  T  L  P  P  S  R  D  E  L  T   160

481  AAGAACCAGGTCAGCCTGACCTGCCTGGTCAAAGGCTTCTATCCCAGCGACATCGCCGTG    540
       161  K  N  Q  V  S  L  T  C  L  V  K  G  F  Y  P  S  D  I  A  V   180

541  GAGTGGGAGAGCAATGGGCAGCCGGAGAACAACTACAAGACCACGCCTCCCGTGCTGGAC    600
       181  E  W  E  S  N  G  Q  P  E  N  N  Y  K  T  T  P  P  V  L  D   200

601  TCCGACGGCTCCTTCTTCCTCTACAGCAAGCTCACCGTGGACAAGAGCAGGTGGCAGCAG    660
       201  S  D  G  S  F  F  L  Y  S  K  L  T  V  D  K  S  R  W  Q  Q   220

661  GGGAACGTCTTCTCATGCTCCGTGATGCATGAGGCTCTGCACAACCACTACACGCAGAAG    720
       221  G  N  V  F  S  C  S  V  M  H  E  A  L  H  N  H  Y  T  Q  K   240

721  AGCCTCTCCCTGTCTCCGGGTAAAGTCGAGGGTGGAGGCGGTTCAGGCGGAGGTGGCTCT    780
       241  S  L  S  L  S  P  G  K  V  E  G  G  G  S  G  G  G  G  S       260

781  GGCGGTGGCGGATCGTTCACCCCGCCCACCGTGAAGATCTTACAGTCGTCCTGCGACGGC    840
       261  G  G  G  G  S  F  T  P  P  T  V  K  I  L  Q  S  S  C  D  G   280

841  GGCGGGCACTTCCCCCCGACCATCCAGCTCCTGTGCCTCGTCTCTGGGTACACCCCAGGG    900
       281  G  G  H  F  P  P  T  I  Q  L  L  C  L  V  S  G  Y  T  P  G   300

901  ACTATCAACATCACCTGGCTGGAGGACGGGCAGGTCATGGACGTGGACTTGTCCACCGCC    960
       301  T  I  N  I  T  W  L  E  D  G  Q  V  M  D  V  D  L  S  T  A   320

961  TCTACCACGCAGGAGGGTGAGCTGGCCTCCACACAAAGCGAGCTCACCCTCAGCCAGAAG   1020
       321  S  T  T  Q  E  G  E  L  A  S  T  Q  S  E  L  T  L  S  Q  K   340

1021  CACTGGCTGTCAGACCGCACCTACACCTGCCAGGTCACCTATCAAGGTCACACCTTTGAG   1080
       341  H  W  L  S  D  R  T  Y  T  C  Q  V  T  Y  Q  G  H  T  F  E   360
```

FIGURE 9B: GE2 S mutant DNA and Protein Sequence

```
1081 GACAGCACCAAGAAGTGTGCAGATTCCAACCCGAGAGGGGTGAGCGCCTACCTAAGCCGG   1140
 361  D  S  T  K  K  C  A  D  S  N  P  R  G  V  S  A  Y  L  S  R   380

1141 CCCAGCCCGTTCGACCTGTTCATCCGCAAGTCGCCCACGATCACCTGTCTGGTGGTGGAC   1200
 381  P  S  P  F  D  L  F  I  R  K  S  P  T  I  T  C  L  V  V  D   400

1201 CTGGCACCCAGCAAGGGGACCGTGAACCTGACCTGGTCCCGGGCCAGTGGGAAGCCTGTG   1260
 401  L  A  P  S  K  G  T  V  N  L  T  W  S  R  A  S  G  K  P  V   420

1261 AACCACTCCACCAGAAAGGAGGAGAAGCAGCGCAATGGCACGTTAACCGTCACGTCCACC   1320
 421  N  H  S  T  R  K  E  E  K  Q  R  N  G  T  L  T  V  T  S  T   440

1321 CTGCCGGTGGGCACCCGAGACTGGATCGAGGGGGAGACCTACCAGTGCAGGGTGACCCAC   1380
 441  L  P  V  G  T  R  D  W  I  E  G  E  T  Y  Q  C  R  V  T  H   460

1381 CCCCACCTGCCCAGGGCCCTCATGCGGTCCACGACCAAGACCAGCGGCCCGCGTGCTGCC   1440
 461  P  H  L  P  R  A  L  M  R  S  T  T  K  T  S  G  P  R  A  A   480

1441 CCGGAAGTCTATGCGTTTGCGACGCCGGAGTGGCCGGGGAGCCGGGACAAGCGCACCCTC   1500
 481  P  E  V  Y  A  F  A  T  P  E  W  P  G  S  R  D  K  R  T  L   500

1501 GCCTGCCTGATCCAGAACTTCATGCCTGAGGACATCTCGGTGCAGTGGCTGCACAACGAG   1560
 501  A  C  L  I  Q  N  F  M  P  E  D  I  S  V  Q  W  L  H  N  E   520

1561 GTGCAGCTCCCGGACGCCCGGCACAGCACGACGCAGCCCCGCAAGACCAAGGGCTCCGGC   1620
 521  V  Q  L  P  D  A  R  H  S  T  T  Q  P  R  K  T  K  G  S  G   540

1621 TTCTTCGTCTTCAGCCGTCTAGAGGTGACCAGGGCCGAATGGGAGCAGAAAGATGAGTTC   1680
 541  F  F  V  F  S  R  L  E  V  T  R  A  E  W  E  Q  K  D  E  F   560

1681 ATCTGCCGTGCAGTCCATGAGGCAGCTAGCCCCTCACAGACCGTCCAGCGAGCGGTGTCT   1740
 561  I  C  R  A  V  H  E  A  A  S  P  S  Q  T  V  Q  R  A  V  S   580

1741 GTAAATCCCGGTAAATGA                                             1758
 581  V  N  P  G  K  *                                             586
```

FIGURE 10A: GE2 H mutant DNA and Protein Sequence

```
DNA       1 TATCCATATGATGTTCCAGATTATGCTGGGGCCCAGCCGGCCAGATCTGAGCCCAAATCT   60
Protein1    Y  P  Y  D  V  P  D  Y  A  G  A  Q  P  A  R  S  E  P  K  S    20

61 TGTGACAAAACTCACACATGCCCACCGTGCCCAGCACCTGAACTCCTGGGGGGACCGTCA  120
         21 C  D  K  T  H  T  C  P  P  C  P  A  P  E  L  L  G  G  P  S    40

121 GTCTTCCTCTTCCCCCCAAAACCCAAGGACACCCTCATGATCTCCCGGACCCCTGAGGTC  180
         41 V  F  L  F  P  P  K  P  K  D  T  L  M  I  S  R  T  P  E  V    60

181 ACATGCGTGGTGGTGGACGTGAGCGCGGAAGACCCTGAGGTCAAGTTCAACTGGTACGTG  240
         61 T  C  V  V  V  D  V  S  A  E  D  P  E  V  K  F  N  W  Y  V    80

241 GACGGCGTGGAGGTGCATAATGCCAAGACAAAGCCGCGGGAGGAGCAGTACAACAGCACG  300
         81 D  G  V  E  V  H  N  A  K  T  K  P  R  E  E  Q  Y  N  S  T   100

301 TACCGGGTGGTCAGCGTCCTCACCGTCCTGCACCAGGACTGGCTGAATGGCAAGGAGTAC  360
        101 Y  R  V  V  S  V  L  T  V  L  H  Q  D  W  L  N  G  K  E  Y   120

361 AAGTGCAAGGTCTCCAACAAAGCCCTCCCAGCCCCCATCGAGAAAACCATCTCCAAAGCC  420
        121 K  C  K  V  S  N  K  A  L  P  A  P  I  E  K  T  I  S  K  A   140

421 AAAGGGCAGCCCCGAGAACCACAGGTGTACACCCTGCCCCCATCCCGGGATGAGCTGACC  480
        141 K  G  Q  P  R  E  P  Q  V  Y  T  L  P  P  S  R  D  E  L  T   160

481 AAGAACCAGGTCAGCCTGACCTGCCTGGTCAAAGGCTTCTATCCCAGCGACATCGCCGTG  540
        161 K  N  Q  V  S  L  T  C  L  V  K  G  F  Y  P  S  D  I  A  V   180

541 GAGTGGGAGAGCAATGGGCAGCCGGAGAACAACTACAAGACCACGCCTCCCGTGCTGGAC  600
        181 E  W  E  S  N  G  Q  P  E  N  N  Y  K  T  T  P  P  V  L  D   200

601 TCCGACGGCTCCTTCTTCCTCTACAGCAAGCTCACCGTGGACAAGAGCAGGTGGCAGCAG  660
        201 S  D  G  S  F  F  L  Y  S  K  L  T  V  D  K  S  R  W  Q  Q   220

661 GGGAACGTCTTCTCATGCTCCGTGATGCATGAGGCTCTGCACAACCACTACACGCAGAAG  720
        221 G  N  V  F  S  C  S  V  M  H  E  A  L  H  N  H  Y  T  Q  K   240

721 AGCCTCTCCCTGTCTCCGGGTAAAGTCGAGGGTGGAGGCGGTTCAGGCGGAGGTGGCTCT  780
        241 S  L  S  L  S  P  G  K  V  E  G  G  G  S  G  G  G  G  S     260

781 GGCGGTGGCGGATCGTTCACCCCGCCCACCGTGAAGATCTTACAGTCGTCCTGCGACGGC  840
        261 G  G  G  G  S  F  T  P  P  T  V  K  I  L  Q  S  S  C  D  G   280

841 GGCGGGCACTTCCCCCCGACCATCCAGCTCCTGTGCCTCGTCTCTGGGTACACCCCAGGG  900
        281 G  G  H  F  P  P  T  I  Q  L  L  C  L  V  S  G  Y  T  P  G   300

901 ACTATCAACATCACCTGGCTGGAGGACGGGCAGGTCATGGACGTGGACTTGTCCACCGCC  960
        301 T  I  N  I  T  W  L  E  D  G  Q  V  M  D  V  D  L  S  T  A   320

961 TCTACCACGCAGGAGGGTGAGCTGGCCTCCACACAAAGCGAGCTCACCCTCAGCCAGAAG 1020
        321 S  T  T  Q  E  G  E  L  A  S  T  Q  S  E  L  T  L  S  Q  K   340

1021 CACTGGCTGTCAGACCGCACCTACACCTGCCAGGTCACCTATCAAGGTCACACCTTTGAG 1080
        341 H  W  L  S  D  R  T  Y  T  C  Q  V  T  Y  Q  G  H  T  F  E   360
```

FIGURE 10B: GE2 H mutant DNA and Protein Sequence

```
1081  GACAGCACCAAGAAGTGTGCAGATTCCAACCCGAGAGGGGTGAGCGCCTACCTAAGCCGG   1140
 361   D   S   T   K   K   C   A   D   S   N   P   R   G   V   S   A   Y   L   S   R    380

1141  CCCAGCCCGTTCGACCTGTTCATCCGCAAGTCGCCCACGATCACCTGTCTGGTGGTGGAC   1200
 381   P   S   P   F   D   L   F   I   R   K   S   P   T   I   T   C   L   V   V   D    400

1201  CTGGCACCCAGCAAGGGGACCGTGAACCTGACCTGGTCCCGGGCCAGTGGGAAGCCTGTG   1260
 401   L   A   P   S   K   G   T   V   N   L   T   W   S   R   A   S   G   K   P   V    420

1261  AACCACTCCACCAGAAAGGAGGAGAAGCAGCGCAATGGCACGTTAACCGTCACGTCCACC   1320
 421   N   H   S   T   R   K   E   E   K   Q   R   N   G   T   L   T   V   T   S   T    440

1321  CTGCCGGTGGGCACCCGAGACTGGATCGAGGGGGAGACCTACCAGTGCAGGGTGACCCAC   1380
 441   L   P   V   G   T   R   D   W   I   E   G   E   T   Y   Q   C   R   V   T   H    460

1381  CCCCACCTGCCCAGGGCCCTCATGCGGTCCACGACCAAGACCAGCGGCCCGCGTGCTGCC   1440
 461   P   H   L   P   R   A   L   M   R   S   T   T   K   T   S   G   P   R   A   A    480

1441  CCGGAAGTCTATGCGTTTGCGACGCCGGAGTGGCCGGGGAGCCGGGACAAGCGCACCCTC   1500
 481   P   E   V   Y   A   F   A   T   P   E   W   P   G   S   R   D   K   R   T   L    500

1501  GCCTGCCTGATCCAGAACTTCATGCCTGAGGACATCTCGGTGCAGTGGCTGCACAACGAG   1560
 501   A   C   L   I   Q   N   F   M   P   E   D   I   S   V   Q   W   L   H   N   E    520

1561  GTGCAGCTCCCGGACGCCCGGCACAGCACGACGCAGCCCCGCAAGACCAAGGGCTCCGGC   1620
 521   V   Q   L   P   D   A   R   H   S   T   T   Q   P   R   K   T   K   G   S   G    540

1621  TTCTTCGTCTTCAGCCGTCTAGAGGTGACCAGGGCCGAATGGGAGCAGAAAGATGAGTTC   1680
 541   F   F   V   F   S   R   L   E   V   T   R   A   E   W   E   Q   K   D   E   F    560

1681  ATCTGCCGTGCAGTCCATGAGGCAGCTAGCCCCTCACAGACCGTCCAGCGAGCGGTGTCT   1740
 561   I   C   R   A   V   H   E   A   A   S   P   S   Q   T   V   Q   R   A   V   S    580

1741  GTAAATCCCGGTAAATGA                                             1758
 581   V   N   P   G   K   *                                          586
```

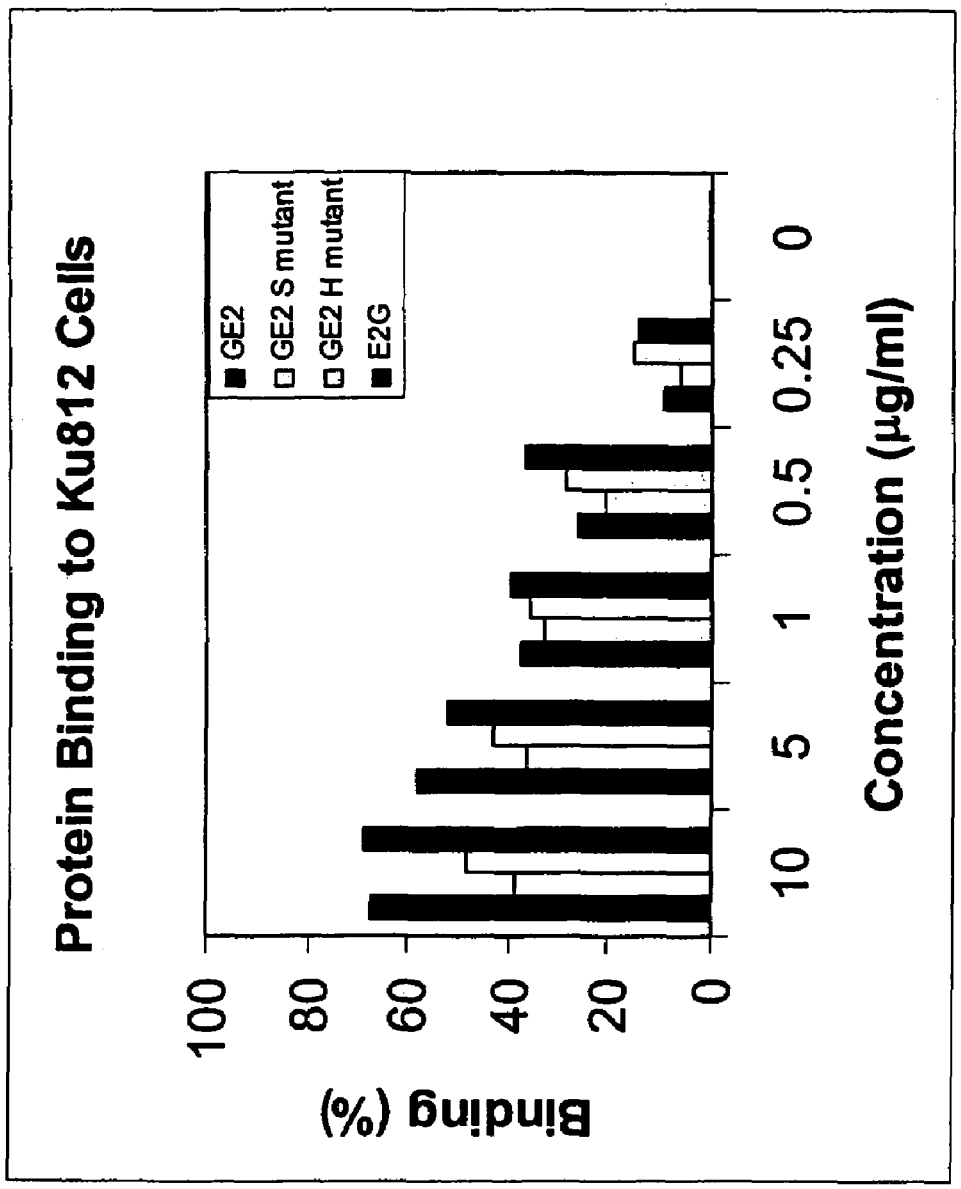
Figure 11 Comparison of GE2 proteins binding to a basophil-like cell line, Ku812.

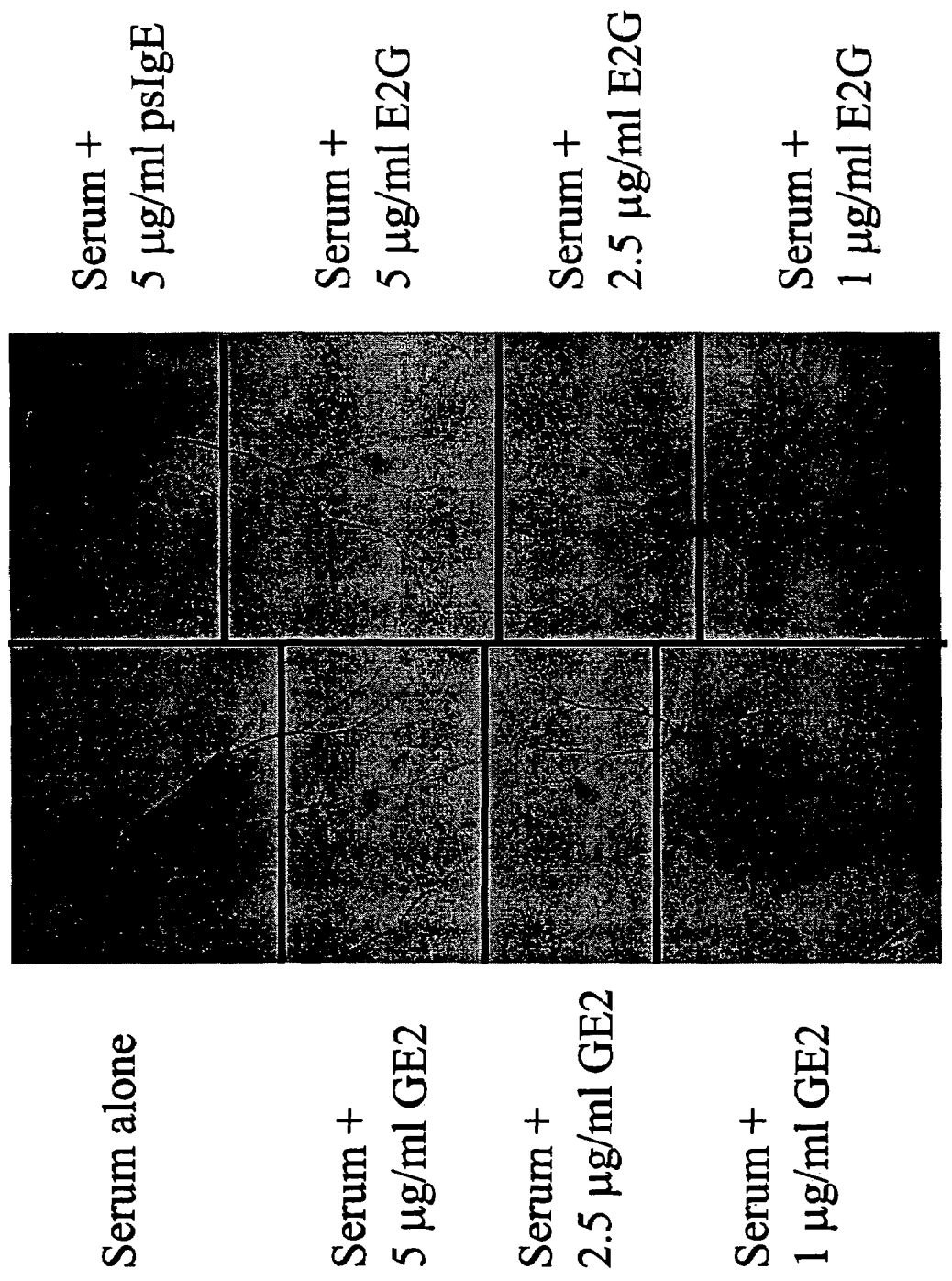
Figure12. Ability of GE2 and E2G to block IgE-mediated passive cutaneous anaphylaxis.

Serum alone

Serum +
2.5 μg/ml GE2 S mutant

Serum +
1 μg/ml GE2 S mutant

Serum +
0.5 μg/ml GE2 S mutant

Serum alone

Serum +
2.5 μg/ml GE2

Serum +
1 μg/ml GE2

Serum +
0.5 μg/ml GE2

Figure13. Ability of GE2 and GE2 S mutant to block IgE-mediated passive cutaneous anaphylaxis.

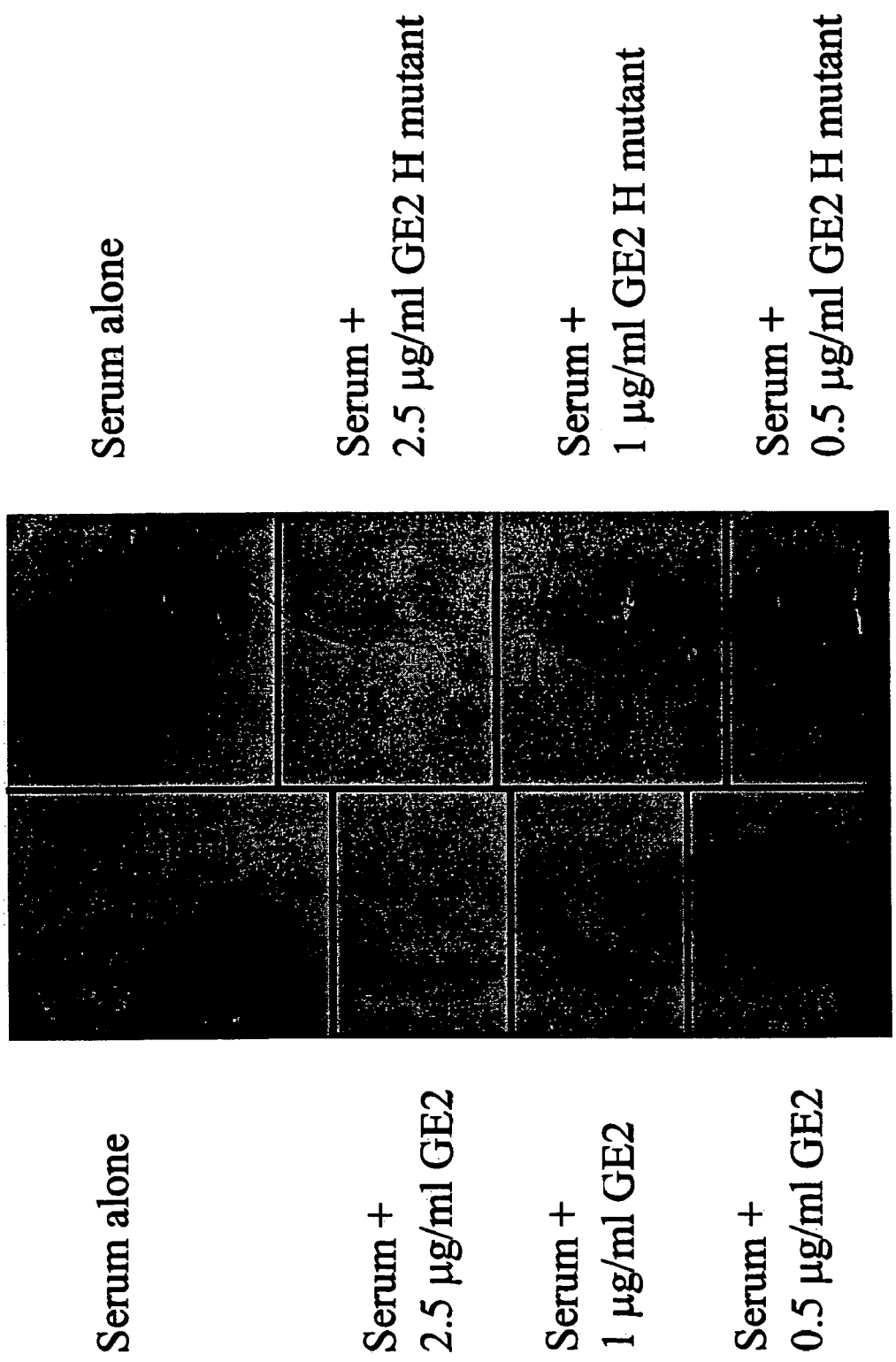
Figure14. Ability of GE2 and GE2 H mutant to block IgE-mediated passive cutaneous anaphylaxis.

Figure 15. GE2 proteins inhibit FcεRI-mediated degranulation in human basophils.

US 7,488,804 B2

MODIFIED FUSION MOLECULES FOR TREATMENT OF ALLERGIC DISEASE

This invention was made with government support under Grant No. AI15251 awarded by the National Institutes of Health. The Government has certain rights in this invention.

TECHNICAL FIELD

The invention concerns an improved approach for the management of IgE-mediated allergic diseases and other disorders mediated through IgE receptors (FcεRs) using novel fusion molecules that are able to complex with an FcεR and FcγR.

DESCRIPTION OF THE RELATED ART

Immunoglobulin receptors (also referred to as Fc receptors) are cell-surface receptors binding the constant region of immunoglobulins, and mediate various immunoglobulin functions other than antigen binding. Fc receptors for IgE molecules are found on many cell types of the immune system (Fridman, W., *FASEB J*, 5(12):2684-90 (1991)). There are two different receptors currently known for IgE. IgE mediates its biological responses as an antibody through the multichain high-affinity receptor, FcεRI, and the low-affinity receptor, FcεRII. The high-affinity FcεRI, expressed on the surface of mast cells, basophils, and Langerhans cells, belongs to the immunoglobulin gene superfamily, and has a tetrameric structure composed of an α-chain, a β-chain and two disulfide-linked γ-chains (Adamczewski, M., and Kinet, J. P., *Chemical Immun.*, 59:173-190 (1994)) that are required for receptor expression and signal transduction (Tunon de Lara, *Rev. Mal. Respir.*, 13(1):27-36 (1996)). The α-chain of the receptor interacts with the distal portion of the third constant domain of the IgE heavy chain. The specific amino acids of human IgE involved in binding to human FcεRI have been identified as including Arg-408, Ser-411, Lys-415, Glu-452, Arg-465, and Met-469 (Presta et al., *J. Biol. Chem.* 269: 26368-73 (1994)). The interaction is highly specific with a binding constant of about $10^{10}$ M$^{-1}$.

The low-affinity FcεRII receptor, represented on the surface of inflammatory cells, including eosinophils, leukocytes, B lymphocytes, and platelets, did not evolve from the immunoglobulin superfamily but has substantial homology with several animal lectins (Yodoi et al., *Ciba Found. Symp.*, 147: 133-148 (1989)) and is made up of a transmembrane chain with an intracytoplasmic NH$_2$ terminus. The low-affinity receptor, FcεRII (CD23) is currently known to have two forms (FcεRIIa and FcεRIIb), both of which have been cloned and sequenced. They differ only in the N-terminal cytoplasmic region, the extracellular domains being identical. FcεRIIa is normally expressed on B cells, while FcεRIIb is expressed on T cells, B cells, monocytes and eosinophils upon induction by the cytokine IL-4.

Through the high-affinity IgE receptor, FcεRI, IgE plays key roles in an array of acute and chronic allergic reactions, including asthma, allergic rhinitis, atopic dermatitis, severe food allergies, chronic urticaria and angioedema, as well as the serious physiological condition of anaphylactic shock as results, for example, from bee stings or penicillin allergy. Binding of a multivalent antigen (allergen) to antigen specifically bound to FcεRI on the surface of mast cells and basophils stimulates a complex series of signaling events that culminate in the release of host vasoactive and proinflammatory mediators contributing to both acute and late-phase allergic responses (Metcalfe et al., *Physiol. Rev.* 77:1033-1079 (1997)).

The function of the low affinity IgE receptor, FcεRII (also referred to as CD23), found on the surface of B lymphocytes, is much less well established than that of FcεRI. FcεRII, in a polymeric state, binds IgE, and this binding may play a role in controlling the type (class) of antibody produced by B cells.

Three groups of receptors that bind the constant region of human IgG have so far been identified on cell surfaces: FcγRI (CD64), FcγRII (CD32), and FcγRIII (CD16), all of which belong to the immunoglobulin gene superfamily. The three Fcγ receptors have a large number of various isoforms.

Along with the stimulatory FcεRI, mast cells and basophils co-express an immunoreceptor tyrosine-based inhibition motif (ITIM)-containing inhibitory low-affinity receptor, FcγRIIb, that acts as a negative regulator of antibody function. FcγRIIb represents a growing family of structurally and functionally similar inhibitory receptors, the inhibitory receptor superfamily (IRS), that negatively regulate ITAM-containing immune receptors (Ott and Cambier, *J. Allergy Clin. Immunol.*, 106:429-440 (2000)) and a diverse array of cellular responses. Coaggregation of an IRS member with an activating receptor leads to phosphorylation of the characteristic ITIM tyrosine and subsequent recruitment of the SH2 domain-containing protein tyrosine phosphatates, SHP-1 and SHP-2, and the SH2 domain-containing phospholipases, SHIP and SHIP2 (Cambier, J. C., *Proc. Natl. Acad. Sci. USA*, 94:5993-5995 (1997)). Possible outcomes of the coaggregation include inhibition of cellular activation, as demonstrated by the coaggregation of FcγRIIb and B-cell receptors, T-cell receptors, activating receptors, including FcεRI, or cytokine receptors (Malbec et al., *Curr. Top. Microbiolo. Immunol.*, 244:13-27 (1999)).

Most studies have so far concentrated on elucidating the mechanisms of FcγRII, in particular FcγRIIb, function. The three alternatively spliced isoforms of the FcγIIb receptor, of which FcγRIIb1' is only found in mice, and FcγRIIb1 and FcγRIIb2 are expressed in both humans and mice, have Ig-like loops and a conserved ITIM, but differ in their cytoplasmic domains. Co-crosslinking of the high-affinity FcεRI receptor and the inhibitory low-affinity receptor FcγII blocks a number of processes, including FcεRI-mediated secretion, IL-4 production, Ca$^{2+}$ mobilization, Syk phosphorylation, and FcεRI-mediated basophil and mast cell activation. In B cells, co-crosslinking of the B-cell receptor and FcγRIIb inhibits B-cell receptor-mediated cell activation (Cambier, J. C., Proc. Natl. Acad. Sci., 94:5993-5995 (1997); Daeron, M., *Annu. Rev. Immunol*, 5:203-234 (1997)), and specifically, inhibits B-cell receptor-induced blastogenesis and proliferation (Chan et al., *Immunology*, 21:967-981 (1971); Phillips and Parker, J. Immunol., 132:627-632 (1984)) and stimulates apoptosis (Ashman et al., *J. Immunol*, 157:5-11 (1996)). Coaggregation of FcγRIIb1 or FcγRIIb2 with FcεRI in rat basophilic leukemia cells, inhibits FcεRI-mediated release of serotonin and TNF-α (Daeron et al., *J. Clin. Invest.*, 95:577-85 (1995); Daeron et al., *Immunity*, 3:635-646 (1995)).

PCT Application Publication No. WO02/088317 describes bifunctional fusion molecules for the treatment of type 1 hypersensitive (i.e. IgE mediated) allergic conditions, methods for the prevention and or treatment of type 1 hypersensitive (i.e. IgE mediated) allergic conditions and anaphylactic responses using the fusion molecules.

U.S. Patent Application No. US 2004/0198961 also describes fusion proteins comprising Fcε fragments conjugated with Fcγ fragments.

Despite advances in understanding the cellular and molecular mechanisms that control allergic responses and improved therapies, the incidence of allergic diseases, especially asthma and severe food allergy, has increased dramatically in recent years in both developed and developing countries (Beasley et al., *J. Allergy Clin. Immunol.* 105:466-472 (2000); Peat and Li, *J. Allergy Clin. Immunol.* 103:1-10 (1999). Ma et al., *J Allergy Clin Immunol.* 112:784-8 (2003))

Allergic diseases can be treated, for example, by allergen-based vaccination, in which increasing doses of allergen are given by injection over years. This approach is costly, time consuming, poorly or not efficacious in many allergic conditions, and has serious side-effects, including death in some instances. Mild asthma can usually be controlled in most patients by relatively low doses of inhaled corticosteroids, while moderate asthma is usually managed by the additional administration of inhaled long-acting beta-antagonists or leukotriene inhibitors. The treatment of severe asthma is still a serious medical problem. In addition, many of the therapeutics currently used in allergy treatment have serious side-effects. There is need for the development of additional therapeutic strategies and agents to control allergic disease, such as asthma, severe food allergy, and chronic urticaria and angioedema.

The object of this invention is to provide an improved fusion molecule for the treatment of conditions associated with anaphylactic hypersensitivity and atopic allergies, such as, for example, asthma, allergic rhinitis, atopic dermatitis, severe food allergies, some forms of chronic urticaria and angioedema, as well as the serious physiological condition of anaphylactic shock as results, for example, from bee stings or penicillin allergy.

SUMMARY OF THE INVENTION

The present invention provides novel fusion compounds that have the ability to crosslink Fcγ receptors with Fcε receptors and block Fcε receptor-mediated biological activities, as well as methods for using such compounds, and compositions and articles of manufacture comprising them. The invention also provides compositions and methods suitable for the prevention or treatment of immune-mediated diseases.

One aspect of the invention concerns an isolated fusion molecule comprising a Fcε fragment functionally connected at its carboxy terminus to an Fcγ1 fragment. It has been found that connecting an Fcγ1 fragment to the carboxy terminus of an Fcε fragment provides a fusion protein with enhanced properties.

In another embodiment, the Fcγ1 fragment comprises an amino acid sequence having at least about 85% identity to the hinge-CH2-CH3 domain amino acid sequence of SEQ ID NO: 3, at least about 90% identity, at least about 95% identity, or at least about 98% identity. In another embodiment, the Fcγ1 fragment comprises an amino acid sequence having at least about 85% identity to the CH1-hinge-CH2-CH3 domain amino acid sequence of SEQ ID NO: 2, at least about 90% identity, at least about 95% identity, or at least about 98% identity. In still other embodiments, the Fcγ1 fragment comprises a least part of the CH2 and CH3 domains of a native human IgG$_1$ constant region, or additionally comprises a least part of the hinge of a native human IgG$_1$ constant region. Alternatively, the Fcγ fragment sequence comprises at least part of the hinge, CH2 and CH3 domains of a native human IgG$_1$ heavy chain constant region in the absence of a functional CH1 region, and alternatively still, the Fcγ1 fragment comprises an amino acid sequence encoded by a nucleic acid hybridizing under stringent conditions to the complement of the IgG heavy chain constant region nucleotide sequence of SEQ ID NO: 1.

In another embodiment, the Fcε fragment comprises an amino acid sequence having at least about 85% identity to the CH2-CH3-CH4 domain amino acid sequence of SEQ ID NO: 6, at least about 90% identity, at least about 95% identity, or at least about 98% identity. In still other embodiments, the Fcε fragment comprises a least part of the CH2, CH3 and CH4 domains of a native human IgE constant region. Alternatively, the Fcε fragment comprises at least part of the CH2, CH3 and CH4 domains of a native human IgE heavy chain constant region in the absence of a functional CH1 region, and alternatively still, the Fcε fragment comprises an amino acid sequence encoded by a nucleic acid hybridizing under stringent conditions to the complement of the IgE heavy chain constant region nucleotide sequence of SEQ ID NO: 4.

In another embodiment, the fusion molecule comprises the polypeptides sequence CHε2-CHε3-CHε4-γhinge-CHγ2CHγ3. In another embodiment the fusion molecule comprises the sequence SEQ ID NO:19.

In some embodiments, the Fcε and the Fcγ1 polypeptide sequences may be functionally connected via a linker, e.g., a polypeptide linker. The length of the polypeptide linker typically is about 1 to 25 amino acid residues, or from about 2 to 25 amino acid residues. In one embodiment, the linker may replace the γhinge sequence. In another embodiment, the linker may functionally connect the CHε3 to the γhinge. In other embodiments, the polypeptide linker sequence comprises at least one endopeptidase recognition motif. In other embodiments, the polypeptide linker sequence comprises a plurality of endopeptidase recognition motifs, and these endopeptidase motifs may include cysteine, aspartate or asparagine amino acid residues. In other embodiments the linker may comprise amino acids encoded by a nuecleic acid restriction enzyme site.

In other embodiments, the fusion molecule comprises at least one amino-terminal ubiquitination target motif.

In a further aspect, the present invention provides isolated nucleic acid molecules encoding a fusion molecule of the present invention. The invention also provides vectors and host cells comprising these nucleic acids.

In a further aspect, the invention concerns a pharmaceutical composition comprising a fusion molecule as hereinabove defined in admixture with a pharmaceutically acceptable excipient or ingredient. In a still further aspect, the invention concerns an article of manufacture comprising a container, a fusion molecule as hereinabove defined within the container, and a label or package insert on or associated with the container. The label or package insert comprises instructions for the treatment or prevention of an immune disease.

In a further aspect, the present invention concerns methods for the treatment or prevention of immune-mediated diseases, where the subject is administered a fusion polypeptide as-described herein.

In another aspect, the invention provides a method for the treatment or prevention of symptoms resulting from a type I hypersensitivity reaction in a subject comprising administering at least one fusion molecule of the present invention to the subject. In another embodiment, the type I hypersensitivity reaction is an anaphylactic response. In another embodiment of this method, the type I hypersensitivity symptoms being prevented comprise an anaphylactic response.

In one aspect of this method of the invention, the immunotherapy received by the subject is for the treatment of type I hypersensitivity-mediated disease or autoimmune disease. In various embodiments of this method, the fusion molecule is administered to the subject prior to the subject receiving immunotherapy, co-administered to the subject during immunotherapy, or administered to the subject after the subject receives the immunotherapy.

In yet another aspect, the invention provides a method for the prevention of a type I hypersensitivity disease in a subject receiving immunotherapy, comprising administering at least one fusion molecule of the present invention to the subject.

These and other aspects of the invention will become more evident upon reference to the following detailed description and attached drawings. It is to be understood however that various changes, alterations and substitutions may be made to the specific embodiments disclosed herein without departing from their essential spirit and scope. In addition, it is further understood that the drawings are intended to be illustrative and symbolic representations of an exemplary embodiment of the present invention and that other non-illustrated embodiments are within the scope of the invention.

BRIEF DESCRIPTION OF THE DRAWINGS

FIG. 1 shows the nucleotide sequence encoding the human IgG1 heavy chain constant region (SEQ ID NO:1).

FIG. 2 shows the amino acid sequence of the human IgG1 heavy chain constant region (SEQ ID NO:2). In the sequence, the CH1 domain extends from amino acid position 122 to amino acid position 219, the hinge region extends from amino acid position 220 to amino acid position 231, the CH2 domain extends from amino acid position 232 to amino acid position 232 to amino acid position 344, and the CH3 domain extends from amino acid position 345 to amino acid position 451 (the C-terminus).

FIG. 3 shows the amino acid sequence of the hinge-CH2-CH3 portion of the human IgG1 heavy chain constant region (SEQ ID NO:3).

FIG. 4 shows the nucleotide sequence encoding the human IgE heavy chain constant region (SEQ ID NO:4).

FIG. 5 shows the amino acid sequence of the human IgE heavy chain constant region (SEQ ID NO:5).

FIG. 6 shows the amino acid sequence of the CH2-CH3-CH4 portion of the human IgE heavy chain constant region (SEQ ID NO:6).

FIGS. 7A and B shows the amino acid sequence of the γhinge-CH-γ2-CHγ3-linker-CHε2-CHε3-CHε4 fusion molecule (GE2) (SEQ ID NO:7 and 8).

FIGS. 8A and B shows the DNA and amino acid sequence of the CHε2-CHε3-CHε4-γhinge-CHγ2-CHγ3 fusion molecule (E2G) of the invention (SEQ ID NOs18 and 19).

FIGS. 9A and B shows the DNA and amino acid sequence of the GE2 S mutant. (SEQ ID NOs: 20 and 21)

FIGS. 10A and B shows the DNA and amino acid sequence of the GE2 H mutant. (SEQ ID NOs: 22 and 23)

FIG. 11 illustrates the binding of GE2 and E2G proteins to a basophil-like cell line Ku812.

FIG. 12 illustrates the ability of GE2 and E2G to block IgE mediated passive cutaneous anaphylaxis.

FIG. 13 illustrates the ability of GE2 and GE2 S mutant to block IgE mediated passive cutaneous anaphylaxis FIG. 14 illustrates the ability of GE2 and GE2 H mutant to block IgE mediated passive cutaneous anaphylaxis.

FIG. 15 illustrates the dose dependent inhibition of basophil histamine release using the fusion proteins GE2, GE2H mutant, GE2 S mutant and E2G mutant.

DETAILED DESCRIPTION OF THE INVENTION

Unless defined otherwise, technical and scientific terms used herein have the same meaning as commonly understood by one of skill in the art to which this invention belongs.

One skilled in the art will recognize many methods and materials similar or equivalent to those described herein, which could be used in the practice of this invention. Indeed the present invention is no way limited to the methods and materials described herein. For purposes of the present invention the following terms are defined.

I. Definitions

The term "functionally connected" with reference to the Fcε and Fcγ polypeptide sequences included in the fusion molecules herein, is used to indicate that such Fcε and Fcγ sequences retain the ability to bind to their respective receptors. As a result, the fusion molecule, comprising such Fcγ and Fcε sequences functionally connected to each other, is capable of cross-linking the respective native receptors, such as, for example, FcγRIIb and FcεRI or FcεRII. In order to achieve a functional connection between the two binding sequences within the fusion molecules of the invention, it is preferred that they retain the ability to bind to the corresponding receptor with a binding affinity similar to that of a native immunoglobulin heavy chain or other native polypeptide binding to that receptor.

The binding is "specific" when the binding affinity of a molecule for a binding target, e.g. an IgG or IgE receptor, is significantly higher (at least about 2-times, at least about 4-times, or at least about 6-times higher) than the binding affinity of that molecule to any other known native polypeptide.

The term "IgG inhibitory receptor" is used to define a member of the inhibitory receptor superfamily (IRS), now known or hereinafter discovered, that is capable of attenuating an FcεR-mediated response, regardless of whether that response is mediated via IgE acting through a high-affinity IgE receptor, e.g. FcεRI, or a low-affinity IgE receptor, or by another mechanism such as an autoantibody to the FcεRI. In one embodiment, the response is an IgE-mediated allergic response, such as a type I (immediate hypersensitivity) reaction but could include autoimmune reactions such as chronic idiopathic urticaria reported due to anti-FcεRI α-chain antibodies in about half of the cases or inflammatory arthritis.

The term "native" or "native sequence" refers to a polypeptide having the same amino acid sequence as a polypeptide that occurs in nature. A polypeptide is considered to be "native" in accordance with the present invention regardless of its mode of preparation. Thus, such native sequence polypeptide can be isolated from nature or can be produced by recombinant and/or synthetic means. The terms "native" and "native sequence" specifically encompass naturally-occurring truncated or secreted forms (e.g., an extracellular domain sequence), naturally-occurring variant forms (e.g., alternatively spliced forms) and naturally-occurring allelic variants of a polypeptide.

The terms "native FcγRIIb," "native sequence FcγRIIb," "native low-affinity IgG inhibitory receptor FcγRIIb," and "native sequence low-affinity IgG inhibitory receptor FcγRIIb" are used interchangeably, and refer to FcγRIIb receptors of any species, including any mammalian species, as occurring in nature. In one embodiment the mammal is human. FcγRIIb is an isoform of the low-affinity IgG receptor FcγRII containing an immunoreceptor tyrosine-based inhibition motif (ITIM). This receptor is the principal FcγRII species in human peripheral blood basophils and cord blood-derived mast cells. For further details see, for example, Malbec and Fridman, Curr. Top. Microbiol. Immunol. 244: 13-27 (1999); Cambier, J. C., Proc. Natl. Acad. Sci. USA 94:5993-5995 (1997); and Ott and Cambier, J. Allergy Clin. Immunol. 106(3):429-440 (2000). FcγRIIb has three alternatively spliced forms designated FcγRIIb1, FcγRIIb1', and FcγRIIb2, which differ only in their cytoplasmic domain sequences. All three alternatively spliced isoforms contain two extracellular Ig-like loops and a single conserved ITIM motif within their cytoplasmic tails, and are specifically included within the definition of FcγRIIb, along with other splice variants that might be identified in the future.

The terms "native FcϵRI," "native sequence FcϵRI," "native high-affinity IgE receptor FcϵRI," and "native sequence high-affinity IgE receptor FcϵRI" are used interchangeably and refer to FcϵRI receptors of any species, including any mammalian species, that occurs in nature. FcϵRI is a member of the multi-subunit immune response receptor (MIRR) family of cell surface receptors that lack intrinsic enzymatic activity but transduce intracellular signals through association with cytoplasmic tyrosine kinases. For further details see, for example, Kinet, J. P., *Annu. Rev. Immunol.* 17:931-972 (1999) and Ott and Cambier, *J. Allergy Clin. Immunol.*, 106:429-440 (2000).

The terms "native FcϵRII", "native sequence FcϵRII", native low-affinity IgE receptor FcϵRII," "native sequence low-affinity IgE receptor FcϵRII" and "CD23" are used interchangeably and refer to FcϵRII receptors of any species, including any mammalian species, that occur in nature. Several groups have cloned and expressed low-affinity IgE receptors of various species. The cloning and expression of a human low-affinity IgE receptor is reported, for example, by Kikutani et al., *Cell* 47:657-665 (1986), and Ludin et al., *EMBO J.* 6:109-114 (1987). The cloning and expression of corresponding mouse receptors is disclosed, for example, by Gollnick et al., *J. Immunol.* 144:1974-82 (1990), and Kondo et al., *Int. Arch. Allergy Immunol.* 105:38-48 (1994). The molecular cloning and sequencing of CD23 for horse and cattle has been recently reported by Watson et al., *Vet. Immunol. Immunopathol.* 73:323-9 (2000). For an earlier review of the low-affinity IgE receptor see also Delespesse et al., *Immunol. Rev.* 125:77-97 (1992).

The term "immunoglobulin" (Ig) is used to refer to the immunity-conferring portion of the globulin proteins of serum, and to other glycoproteins, which may not occur in nature but have the same functional characteristics. The term "immunoglobulin" or "Ig" specifically includes "antibodies" (Abs). While antibodies exhibit binding specificity to a specific antigen, immunoglobulins include both antibodies and other antibody-like molecules that lack antigen specificity. Native immunoglobulins are secreted by differentiated B cells termed plasma cells, and immunoglobulins without any known antigen specificity are produced at low levels by the immune system and at increased levels by myelomas. As used herein, the terms "immunoglobulin," "Ig," and grammatical variants thereof are used to include antibodies, and Ig molecules without known antigen specificity, or without antigen binding regions.

Native immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The main mammalian Ig isotypes (classes) found in serum, and the corresponding Ig heavy chains, shown in parentheses, are listed below:

IgG (γ chain): the principal Ig in serum, the main antibody raised in response to an antigen, has four major subtypes, several of which cross the placenta;

IgE (ϵ chain): this Ig binds tightly to mast cells and basophils, and when additionally bound to antigen, causes release of histamine and other mediators of immediate hypersensitivity; plays a primary role in allergic reactions, including hay fever, asthma and anaphylaxis; may serve a protective role against parasites and may play an important role in antigen presentation;

IgA (α chain): this Ig is present in serum and particularly abundant in external secretions, such as saliva, tears, mucous, and colostrum;

IgM (μ chain): the Ig first induced in response to an antigen; it has lower affinity than antibodies produced later, is pentameric and primarily localized in the circulation; and IgD (δ chain): this Ig is found in relatively high concentrations in umbilical cord blood, serves primarily as an early cell receptor for antigens and primarily functions as a lymphocyte cell surface molecule.

Antibodies of the IgG, IgE, IgA, IgM, and IgD isotypes may have the same variable regions, i.e. the same antigen binding cavities, even though they differ in the constant region of their heavy chains. The constant regions of an immunoglobulin, e.g. antibody are not involved directly in binding the antibody to an antigen, but correlate with the different effector functions mediated by antibodies, such as complement activation or binding to one or more of the antibody Fc receptors expressed on basophils, mast cells, lymphocytes, monocytes and granulocytes.

Some of the main human antibody isotypes (classes) are divided into further sub-classes. IgG has four known sub-classes: $IgG_1$ ($γ_1$), $IgG_2$ ($γ_2$), $IgG_3$ ($γ_3$), and $IgG_4$ ($γ_4$), while IgA has two known sub-classes: $IgA_1$ ($α_1$) and $IgA_2$ ($α_2$).

A light chain of an Ig molecule is either a κ or a λ chain.

The constant region of an immunoglobulin heavy chain is further divided into globular, structurally discrete domains, termed heavy chain constant domains. For example, the constant region of an $IgG_1$ immunoglobulin heavy chain comprises three constant domains, CH1, CH2 and CH3, and a hinge region between the CH1 and CH2 domains. The IgE immunoglobulin heavy chain comprises four constant domains: CH1, CH2, CH3 and CH4 and does not have a hinge region.

Immunoglobulin sequences, including sequences of immunoglobulin heavy chain constant regions are well known in the art and are disclosed, for example, in Kabat et al., *Sequences of Proteins of Immunological Interest,* 5th Ed. Public Health Service, National Institute of Health, Bethesda, Md. (1991). For a discussion of the human $IgG_1$ heavy chain constant region ($γ_1$), see also Ellison et al., *Nucl. Acid Res.* 10:4071-4079 (1982); and Takahashi et al., *Cell* 29:671-679 (1982). For a discussion of the human $IgG_2$ constant region ($γ_2$), see also Krawinkel et al., EMBO J. 1:403-407 (1982); Ellison et al., *Proc. Nat. Acad. Sci.* USA 79:1984-1988 (1982); and Takahashi et al. (1982), supra. For a discussion of human $IgG_3$ heavy chain constant region ($γ_3$), see also Krawinkel et al., (1982), supra, and Takahashi et al. (1982), supra. For a discussion of human $IgG_4$ heavy chain constant region ($γ_4$), see also Ellison et al., *DNA* 1:11-18 (1982), Krawinkel et al., (1982), supra, and Takahashi et al., (1982), supra. For a discussion of the human IgE heavy chain constant region (ϵ), see also Max et al., *Cell* 29:691-699 (1982). IgE isoforms are described in Saxon et al., *J. Immunol.* 147:4000

(1991); Peng et al., *J. Immunol.* 148:129-136 (1992); Zhang et al., *J. Exp. Med.* 176:233-243 (1992); and Hellman, *Eur. J. Immunol.* 23:159-167 (1992).

The terms "native Fcγ1" and "native sequence Fcγ1", are used interchangeable and refer to the Fcγ1 sequence of any species including any mammalian species, as occurring in nature. In one embodiment the animal is human.

The "Fcγ1 fragment" is an amino acid sequence having at least about 85% identity to the hinge-CH2-CH3 domain amino acid sequence of SEQ ID NO: 3, at least about 90% identity, at least about 95% identity, or at least about 98% identity. In another embodiment the "Fcγ1 fragment" is an amino acid sequence having at least about 85% identity to the CH1-hinge-CH2-CH3 domain amino acid sequence of SEQ ID NO: 2, at least about 90% identity, at least about 95% identity, or at least about 98% identity. In still other embodiments, the Fcγ1 fragment comprises a least part of the CH2 and CH3 domains of a native human $IgG_1$ constant region, or additionally comprises a least part of the hinge of a native human $IgG_1$ constant region. Alternatively, the Fcγ1 sequence comprises at least part of the hinge, CH2 and CH3 domains of a native human $IgG_1$ heavy chain constant region in the absence of a functional CH1 region, and alternatively still, the Fcγ1 fragment comprises an amino acid sequence encoded by a nucleic acid hybridizing under stringent conditions to at least a portion of the complement of the IgG heavy chain constant region nucleotide sequence of SEQ ID NO: 1. The Fcγ1 sequence g includes variants of the Fcγ1 sequence which retain the biological activity of the Fcγ1 fragment, including but not limited to the ability to bind to a native FcγRIIb receptor.

The terms "native Fcε and "native sequence Fcε", are used interchangeable and refer to the Fcε sequence of any species including any mammalian species, as occurring in nature. In one embodiment the animal is human.

In another embodiment, the Fcε fragment comprises an amino acid sequence having at least about 85% identity to the CH2-CH3-CH4 domain amino acid sequence of SEQ ID NO: 6, at least about 90% identity, at least about 95% identity, or at least about 98% identity. In still other embodiments, the Fcε fragment comprises a least part of the CH2, CH3 and CH4 domains of a native human IgE constant region. Alternatively, the Fcε fragment comprises at least part of the CH2, CH3 and CH4 domains of a native human IgE heavy chain constant region in the absence of a functional CH1 region, and alternatively still, the Fcε fragment comprises an amino acid sequence encoded by a nucleic acid hybridizing under stringent conditions to at least a portion of the complement of the IgE heavy chain constant region nucleotide sequence of SEQ ID NO: 4. The Fcε sequence includes variants of the Fcε sequence which retain the biological activity of the Fcε fragment, including but not limited to the ability to bind to a native FcεRI and/or FcεRII receptor.

The term "peptide", "polypeptide", or "protein" in singular or plural, is used herein to refer to any peptide or protein comprising two or more amino acids joined to each other in a linear chain by peptide bonds. As used herein, the term refers to both short chains, which also commonly are referred to in the art as peptides, oligopeptides and oligomers, and to longer chains, commonly referred to in the art as proteins. Polypeptides, as defined herein, may contain amino acids other than the 20 naturally occurring amino acids, and may include modified amino acids. The modification can be anywhere within the polypeptide molecule, such as, for example, at the terminal amino acids, and may be due to natural processes, such as processing and other post-translational modifications, or may result from chemical and/or enzymatic modification techniques which are well known to the art. The known modifications include, without limitation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature, such as, for instance, Creighton, T. E., *Proteins—Structure And Molecular Properties,* 2nd Ed., W. H. Freeman and Company, New York (1993); Wold, F., "Posttranslational Protein Modifications: Perspectives and Prospects," in *Posttranslational Covalent Modification of Proteins*, Johnson, B. C., ed., Academic Press, New York (1983), pp. 1-12; Seifter et al., "Analysis for protein modifications and nonprotein cofactors," *Meth. Enzymol.* 182:626-646 (1990), and Rattan et al., *Ann. N.Y Acad. Sci.* 663:48-62 (1992).

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine. Accordingly, when glycosylation is desired, a polypeptide is expressed in a glycosylating host, generally eukaryotic host cells. Insect cells often carry out the same post-translational glycosylations as mammalian cells and, for this reason, insect cell expression systems have been developed to express efficiently mammalian proteins having native patterns of glycosylation.

It will be appreciated that polypeptides are not always entirely linear. For instance, polypeptides may be branched as a result of ubiquitination, and they may be circular, with or without branching, generally as a result of post-translational events, including natural processing and events brought about by human manipulation which do not occur naturally. Circular, branched and branched circular polypeptides may be synthesized by non-translation natural process and by entirely synthetic methods, as well. Such structures are within the scope of the polypeptides as defined herein.

Amino acids are represented by their common one- or three-letter codes, as is common practice in the art. Accordingly, the designations of the twenty naturally occurring amino acids are as follows: Alanine=Ala (A); Arginine=Arg (R); Aspartic Acid=Asp (D); Asparagine=Asn (N); Cysteine=Cys (C); Glutamic Acid=Glu (E); Glutamine=Gln (O); Glycine=Gly (G); Histidine=His (H); Isoleucine=Ile (I); Leucine=Leu (L); Lysine=Lys (K); Methionine=Met (M); Phenylalanine=Phe (F); Proline—Pro (P); Serine=Ser (S); Threonine=Thr (T); Tryptophan=Trp (W); Tyrosine=Tyr (Y); Valine=Val (V). The polypeptides herein may include all L-amino acids, all D-amino acids or a mixture thereof. The polypeptides comprised entirely of D-amino acids may be advantageous in that they are expected to be resistant to proteases naturally found within the human body, and may have longer half-lives.

The term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have at least one amino acid deleted in a particular region of the molecule.

The terms "fragment," "portion" and "part," as used interchangeably herein, refer to any composition of matter that is smaller than the whole of the composition of matter from which it is derived. For example, a portion of a polypeptide may range in size from two amino acid residues to the entire amino acid sequence minus one amino acid. However, in most cases, it is desirable for a "portion" or "fragment" to retain an activity or quality which is essential for its intended use. For example, useful portions of an antigen are those portions that retain an epitope determinant. Also, in one embodiment, useful portions of an immunoglobulin heavy chain constant region are those portions that retain the ability to form covalent homodimeric structures and are able to bind an Fcγ receptor or an Fcε receptor.

The term "at least a portion," as used herein, is intended to encompass portions as well as the whole of the composition of matter.

The term "functionally connected at its carboxy terminus" means that the Fcε fragment is connected by its α-carboxy functional group to the α-amino functional group of the Fcγ1 sequence. It is contemplated that the functional connection may include a linker sequence.

"Sequence identity" is defined as the percentage of amino acid residues in a candidate sequence that are identical with the amino acid residues in a reference polypeptide sequence (e.g., a native polypeptide sequence), after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", Nucleic Acids Res., 25:3389-3402. The parameters are set to default values, with the exception of the Penalty for mismatch, which is set to −1.

The term "sequence similarity" as used herein, is the measure of nucleic acid sequence identity, as described above, and in addition also incorporates conservative amino acid substitutions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions see Ausubel et al., *Current Protocols in Molecular Biology*, Wiley Interscience Publishers 1995).

"Stringent" hybridization conditions are sequence dependent and will be different with different environmental parameters (e.g., salt concentrations, and presence of organics). Generally, stringent conditions are selected to be about 5° C. to 20° C. lower than the thermal melting point ($T_m$) for the specific nucleic, acid sequence at a defined ionic strength and pH. Stringent conditions are about 50° C. to 10° C. lower than the thermal melting point for a specific nucleic acid bound to a perfectly complementary nucleic acid. The $T_m$ is the temperature (under defined ionic strength and pH) at which 50% of a nucleic acid (e.g., tag nucleic acid) hybridizes to a perfectly matched probe.

"Stringent" wash conditions are ordinarily determined empirically for hybridization of each set of tags to a corresponding probe array. The arrays are first hybridized (typically under stringent hybridization conditions) and then washed with buffers containing successively lower concentrations of salts, or higher concentrations of detergents, or at increasing temperatures until the signal to noise ratio for specific to non-specific hybridization is high enough to facilitate detection of specific hybridization. Stringent temperature conditions will usually include temperatures in excess of about 30° C., more usually in excess of about 37° C., and occasionally in excess of about 45° C. Stringent salt conditions will ordinarily be less than about 1000 mM, usually less than about 500 mM, more usually less than about 400 mM, typically less than about 300 mM, less than about 200 mM, or less than about 150 mM. However, the combination of parameters is more important than the measure of any single parameter. See, e.g., Wetmur et al, *J. Mol. Biol.* 31:349-70 (1966), and Wetmur, *Critical Reviews in Biochemistry and Molecular Biology* 26(34):227-59 (1991).

In one embodiment, "stringent conditions" or "high stringency conditions," as defined herein, may be hybridization in 50% formamide, 6×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (100 µg/ml), 0.5% SDS, and 10% dextran sulfate at 42° C., with washes at 42° C. in 2×SSC (sodium chloride/sodium citrate) and 0.1% SDS at 55° C., followed by a high-stringency wash consisting of 0.2×SSC containing 0.1% SDS at 42° C.

The terms "complement," "complementarity" or "complementary," as used herein, are used to describe single-stranded polynucleotides related by the rules of antiparallel base-pairing. For example, the sequence 5'-CTAGT-3' is completely complementary to the sequence 5'ACTAG-3'. Complementarity may be "partial" where the base pairing is less than 100%, or complementarity may be "complete" or "total," implying perfect 100% antiparallel complementation between the two polynucleotides. By convention in the art, single-stranded nucleic acid molecules are written with their 5' ends to the left, and their 3' ends to the right.

The tem "allergen," and grammatical variants thereof, are used to refer to special antigens that are capable of inducing IgE-mediated allergies. An allergen can be almost anything that acts as an antigen and stimulates an IgE-mediated allergic reaction. Common allergens can be found, for example, in food, pollen, mold, house dust which may contain mites as well as dander from house pets, venom from insects such as bees, wasps and mosquitoes.

The term "antigen," as used herein, refers to any agent that is recognized by an antibody, while the term "immunogen" refers to any agent that can elicit an immunological response in a subject. The terms "antigen" and "immunogen" both encompass, but are not limited to, polypeptides. In most, but not all cases, antigens are also immunogens.

The terms "epitope" or "antigenic determinant" as used herein, refer to that portion of an antigen that forms the region that reactions with a particular antibody variable region, and thus imparts specificity to the antigen/antibody binding. A single antigen may have more than one epitope. An immunodominant epitope is an epitope on an antigen that is preferentially recognized by antibodies to the antigen. In some cases, where the antigen is a protein, the epitope can be "mapped," and an "antigenic peptide" produced corresponding approximately to just those amino acids in the protein that are responsible for the antibody/antigen specificity. Such "antigenic peptides" find use in peptide immunotherapies.

The terms "immunotherapy," "desensitisation therapy," "hyposensitisation therapy," "tolerance therapy" and the like, as used herein, describe methods for the treatment of various hypersensitivity disorders, where the avoidance of an allergen or autoantigen is not possible or is impractical. As used herein, these terms are used largely interchangeably. These methods generally entail the delivery to a subject of the antigenic material in a controlled manner to induce tolerance to the antigen and/or downregulate an immune response that occurs upon environmental exposure to the antigen. These therapies typically entail injections of the antigen (e.g., an allergen or autoantigen) over an extended period of time (months or years) in gradually increasing doses. The antigen used in the immunotherapies is typically, but not exclusively, polypeptides. For example, hayfever desensitisation therapy downregulates allergic response to airborn pollen, where the subject is injected with a pollen extract. From a clinical perspective, these treatments are suboptimal, as the injections are often uncomfortable, as well as inconvenient. Furthermore, a significant risk of potentially life-threatening anaphylactic responses during the therapies exists. Adapting immunotherapy techniques for the treatment of various autoimmune disorders has been proposed, where the autoantigen is administered to a subject in the hope of inducing tolerance to the autoantigen, and thereby eliminating the immune destruction of the endogenous autoantigen or autoantigenic tissue. For example, insulin and myelin-basic-protein have been delivered to animal models and humans for the purpose of downregulating autoimmune type-I diabetes mellitus and multiple sclerosis, respectively.

The terms "peptide therapy" and "peptide immunotherapy," and the like, as used herein, describe methods of immunotherapy, wherein the antigen (e.g., an allergen or autoantigen) delivered to a subject is a short polypeptide (i.e., a peptide). Furthermore, the peptide delivered during peptide therapy may contain only those amino acids defining an immunodominant epitope (e.g., the myelin-basic-protein epitope (MBP).

The terms "vaccine therapy," "vaccination" and "vaccination therapy," as used interchangeably herein, refer in general to any method resulting in immunological prophylaxis. In one aspect, vaccine therapy induces an immune response, and thus long-acting immunity, to a specific antigen. These methods generally entail the delivery to a subject of an immunogenic material to induce immunity. In this case, the immunogenic material is generally killed microbes of virulent stains or living, attenuated strains, or derivatives or products of virulent pathogens. In another aspect, the "vaccine therapy" refers to a method for the downregulation of an immune potential to a particular antigen (e.g., to suppress an allergic response). This type of vaccine therapy is also referred to as "tolerance therapy." Vaccine therapies typically entail a series of parenteral or oral administrations of the immunogenic material over an extended period of time.

A "Type I" allergic reaction or "immediate hypersensitivity" or "atopic allergy" occurs when an antigen entering the body encounters mast cells or basophils which have been sensitized by IgE attached to its high-affinity receptor, FcєRI on these cells. When an allergen reaches the sensitized mast cell or basophil, it cross-links surface-bound IgE, causing an increase in intracellular calcium ($Ca^{2+}$) that triggers the release of pre-formed mediators, such as histamine and proteases, and newly synthesized, lipid-derived mediators such as leukotrienes and prostaglandins. These autocoids produce the clinical symptoms of allergy. In addition, cytokines, e.g. IL-4, TNF-alpha, are released from degranulating basophils and mast cells, and serve to augment the inflammatory response that accompanies an IgE reaction (see, e.g. *Immunology*, Fifth Edition, Roitt et al., eds., 1998, pp. 302-317).

Symptoms and signs associated with type I hypersensitivity responses are extremely varied due to the wide range of tissues and organs that can be involved. These symptoms and signs can include, but are not limited to: itching of the skin, eyes, and throat, swelling and rashes of the skin (angioedema and urticaria/hives), hoarseness and difficulty breathing due to swelling of the vocal cord area, a persistent bumpy red rash that may occur anywhere on the body, shortness of breath and wheezing (from tightening of the muscles in the airways and plugging of the airways, i.e., bronchoconstriction) in addition to increased mucus and fluid production, chest tightness and pain due to construction of the airway muscles, nausea, vomiting diarrhea, dizziness and fainting from low blood pressure, a rapid or irregular heartbeat and even death as a result of airway and/or cardiac compromise.

Examples of disease states that result from allergic reactions, and demonstrating hypersensitivity symptoms and/or signs include, but are not limited to, allergic rhinitis, allergic conjunctivitis, atopic dermatitis, allergic [extrinsic] asthma, some cases of urticaria and angioedema, food allergy, and anaphylactic shock in which there is systemic generalized reactivity and loss of blood pressure that may be fatal.

The terms "anaphylaxis," "anaphylactic response," "anaphylactic reaction," "anaphylactic shock," and the like, as used interchangeably herein, describe the acute, often explosive, IgE-mediated systemic physiological reaction that occurs in a previously sensitized subject who receives the sensitizing antigen. Anaphylaxis occurs when the previously sensitizing antigen reaches the circulation. When the antigen reacts with IgE on basophils and mast cells, histamine, leukotrienes, and other inflammatory mediators are released. These mediators cause the smooth muscle contraction (responsible for wheezing and gastrointestinal symptoms) and vascular dilation (responsible for the low blood pressure) that characterize anaphylaxis. Vasodilation and escape of plasma into the tissues causes urticaria and angioedema and results in a decrease in effective plasma volume, which is the major cause of shock. Fluid escapes into the lung alveoli and may produce pulmonary edema. Obstructive angioedema of the upper airway may also occur. Arrhythmias and cardiogenic shock may develop if the reaction is prolonged. The term "anaphylactoid reaction" refers to a physiological response that displays characteristics of an anaphylactic response.

Symptoms of an anaphylactic reaction vary considerably among patients. Typically, in about 1 to 15 minutes (but rarely after as long as 2 hours), symptoms can include agitation and flushing, palpitations, paresthesias, pruritus, throbbing in the ears, coughing, sneezing, urticaria and angioedema, vasodilation, and difficulty breathing owing to laryngeal edema or bronchospasm. Nausea, vomiting, abdominal pain, and diarrhea are also sometimes observed. Shock may develop within another 1 or 2 minutes, and the patient may convulse, become incontinent, unresponsive, and succumb to cardiac arrest, massive angioedema, hypovolemia, severe hypotension and vasomotor collapse and primary cardiovascular collapse. Death may ensue at this point if the antagonist epinephrine is not immediately available. Mild forms of anaphylactic response result in various symptoms including generalized pruritus, urticaria, angioedema, mild wheezing, nausea and vomiting. Patients with the greatest risk of anaphylaxis are those who have reacted previously to a particular drug or antigen.

The terms "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, conjugated with transferrin, complexed with compounds such as polyethylene glycol (PEG) to immunologically "mask" the molecule and/or increase half-life, or conjugated to a non-viral protein. In one embodiment the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A "host cell" includes an individual cell or cell culture which can be or has been a recipient of any vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a nucleic acid of the present invention.

The term "promoter" means a nucleotide sequence that, when operably linked to a DNA sequence of interest, promotes transcription of that DNA sequence.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The term "IgE-mediated biological response" is used to refer to a condition or disease which is characterized by signal transduction through an IgE receptor, including the high-affinity IgE receptor, FcεRI, and the low-affinity IgE receptor FcεRII. The definition includes, without limitation, conditions associated with anaphylactic hypersensitivity and atopic allergies, such as, for example, asthma, allergic rhinitis, atopic dermatitis, food allergies, chronic urticaria and angioedema, as well as the serious physiological condition of anaphylactic shock, usually caused by bee stings or medications such as penicillin.

The terms "treat" or "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder as well as those prone to have the condition or disorder or those in which the condition or disorder is to be prevented.

"Chronic" administration refers to administration of the agent(s) in a continuous mode as opposed to an acute mode, so as to maintain a desired effect or level of agent(s) for an extended period of time.

"Intermittent" administration is treatment that is not consecutively done without interruption, but rather is periodic in nature.

Administration "in combination with" one or more further therapeutic agents includes simultaneous (concurrent) and consecutive administration in any order.

An "effective amount" is an amount sufficient to effect beneficial or desired therapeutic (including preventative) results. An effective amount can be administered in one or more administrations.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "mammal" or "mammalian species" refers to any animal classified as a mammal, including humans, domestic and farm animals, and zoo, sports, or pet animals, such as dogs, cats, cattle, horses, sheep, pigs, goats, rabbits, as well as rodents such as mice and rats, etc. In one embodiment the mammal is human.

The terms "subject" or "patient," as used herein, are used interchangeably, and can refer to any animal, and in one embodiment a mammal, that is the subject of an examination, treatment, analysis, test or diagnosis. In one embodiment, humans are the subject. A subject or patient may or may not have a disease or other pathological condition.

The terms "disease," "disorder" and "condition" are used interchangeably herein, and refer to any disruption of normal body function, or the appearance of any type of pathology. The etiological agent causing the disruption of normal physiology may or may not be known. Furthermore, although two patients may be diagnosed with the same disorder, the particular symptoms displayed by those individuals may or may not be identical.

II. Detailed Description

In one embodiment, the present invention is directed to an isolated fusion molecule comprising an Fcε fragment functionally connected at the carboxy end of the Fcε fragment to an Fcγ1 fragment.

In one embodiment, the fusion molecules of the present invention comprise a Fcε fragment sequence including functionally active CH2, CH3 and CH4 domains of the constant region of an IgE heavy chain (CHε2-CHε3-CHε4 sequence) linked at its C-terminus to the N-terminus of a second polypeptide including functionally active hinge, CH2 and CH3 domains of the constant region of an $IgG_1$ heavy chain (γhinge-CHγ2-CHγ3 sequence).

In one embodiment, the IgE heavy chain constant region sequence (or a homologous sequence) is fused C-terminally to the N-terminus of the $IgG_1$ heavy chain constant region sequence (or a homologous sequence). The fusion molecules may also comprise repeats of identical or different IgG and/or IgE heavy chain constant region sequences. For example, a IgE heavy chain constant region sequence can be followed by two repeats of $IgG_1$ heavy chain constant region sequences (EGG structure), or two repeats of identical or different IgG heavy chain constant region sequences may flank an IgE heavy chain constant region sequence (GEG structure), etc. Fusion molecules comprising more than one binding sequence for a target receptor (e.g. an FcγRIIb receptor) are expected to have superior biological, e.g. anti-allergic properties.

In all embodiments, the two polypeptide sequences are functionally connected, which means that they retain the ability to bind to the respective native receptors, such as a native IgG inhibitory receptor, e.g. a low-affinity FcγRIIb receptor, and to a native high-affinity IgE receptor, e.g. FcεRI or low-affinity IgE receptor, e.g. FcεRII as desired. As a result, the fusion molecules, comprising the Fcε fragment and the Fcγ fragment functionally connected to each other, are capable of cross-linking the respective native receptors, such as FcγRIIb and FcεRI or FcγRIIb and FcεRII. In order to achieve a functional connection between the two binding sequences within the fusion molecules of the invention, it is preferred that they retain the ability to bind to the corresponding receptor with a binding affinity similar to that of a native immunoglobulin ligand of that receptor.

In one embodiment, the Fcε fragment present in the fusion molecules of the invention has at least about 80%, at least about 85%, at least about 90%, at least about 95%, or at least about 98% sequence identity with the amino acid sequence of the CH2-CH3-CH3 region of a native IgE, e.g. native human IgE. In one embodiment, the sequence identity is defined with reference to the human CHγ2-CHγ3-CHε4 sequence of SEQ ID NO: 6.

In one embodiment, the Fcγ fragment present in the fusion molecules of the invention has at least about 80%, at least about 85%, at least about 90%, at least about 95%, or at least about 98% sequence identity with the amino acid sequence of the hinge-CH2-CH3 region of a native $IgG_1$, e.g. native human $IgG_1$. In one embodiment, the Fcγ fragment present in the fusion molecules of the invention has at least about 80%, at least about 85%, at least about 90%, at least about 95%, or at least about 98% sequence identity with the amino acid sequence of the CH1-hinge-CH2-CH3 region of a native $IgG_1$, e.g. native human $IgG_1$. In one embodiment, the sequence identity is defined with reference to the human γhinge-CHγ2-CHγ3 sequence of SEQ ID NO: 3.

It is required that Fcε fragment and the Fcγ1 fragment retain the ability to bind to the corresponding native receptor, such as a native high-affinity IgE receptor (e.g. FcεRI) or native low-affinity IgE receptor (FcεRII, CD23) and a native IgG inhibitory receptor (e.g. FcγRIIb), respectively. The receptor binding domains within the native IgG and IgE heavy chain constant region sequences have been identified. It has been reported that the CH2-CH3 interface of the IgG Fc domain contains the binding sites for a number of Fc receptors, including the FcγRIIb low-affinity receptor (Wines et al., *J. Immunol.* 164(10):5313-5318 (2000)). Based on FcεRI binding studies, Presta et al., *J. Biol. Chem.* 269:26368-26373 (1994) proposed that six amino acid residues (Arg-408, Ser-411, Lys-415, Glu-452, Arg-465, and Met-469) located in three loops, C-D, E-F, and F-G, computed to form the outer ridge on the most exposed side of the human IgE heavy chain CH3 domain, are involved in binding to the high-affinity receptor FcεRI, mostly by electrostatic interactions. Helm et al., *J. Cell Biol.* 271(13):7494-7500 (1996), reported that the high-affinity receptor binding site in the IgE molecule includes the Pro343-Ser353 peptide sequence within the CH3 domain of the IgE heavy chain, but sequences N— or C-terminal to this core peptide are also necessary to provide structural scaffolding for the maintenance of a receptor binding conformation. In particular, they found that residues, including His, in the C-terminal region of the ε-chain make an important contribution toward the maintenance of the high-affinity of interaction between IgE and FcεRI. The Fcε and Fcγ1 polypeptide sequences within the fusion molecules of the invention are designed to bind to residues within such binding regions.

Based on this knowledge, the amino acid sequence variants may be designed to retain the native amino acid residues essential for receptor binding, or to perform only conservative amino acid alterations (e.g. substitutions) at such residues.

In making amino acid sequence variants that retain the required binding properties of the corresponding native sequences, the hydropathic index of amino acids may be considered. For example, it is known that certain amino acids may be substituted for other amino acids having a similar hydropathic index or score without significant change in biological activity. Thus, isoleucine, which has a hydrophatic index of +4.5, can generally be substituted for valine (+4.2) or leucine (+3.8), without significant impact on the biological activity of the polypeptide in which the substitution is made. Similarly, usually lysine (−3.9) can be substituted for arginine (−4.5), without the expectation of any significant change in the biological properties of the underlying polypeptide.

Other considerations for choosing amino acid substitutions include the similarity of the side-chain substituents, for example, size, electrophilic character, charge in various amino acids. In general, alanine, glycine and serine; arginine and lysine; glutamate and aspartate; serine and threonine; and valine, leucine and isoleucine are interchangeable, without the expectation of any significant change in biological properties. Such substitutions are generally referred to as conservative amino acid substitutions, and, as noted above, are one type of substitutions within the polypeptides of the present invention.

Alternatively or in addition, the amino acid alterations may serve to enhance the receptor binding properties of the fusion molecules of the invention. Variants with improved receptor binding and, as a result, superior biological properties can be readily designed using standard mutagenesis techniques, such as alanine-scanning mutagenesis, PCR mutagenesis or other mutagenesis techniques, coupled with receptor binding assays, such as the assay discussed below or described in the Example.

The fusion molecules of the present invention are typically produced and act as homodimers or heterodimers, comprising two of the fusion molecules hereinabove described covalently linked to each other. The covalent attachment may be achieved via one or more disulfide bonds. For example, the prototype protein designated E2G is produced as a homodimer composed of the two CH$\epsilon$2-CH$\epsilon$3-CH$\epsilon$4-$\gamma_1$hinge-CH $\gamma_1$2-CH $\gamma_1$3-chains connected to each other by interchain disulfide bonds, to provide an immunoglobulin-like structure. It is also possible to produce heterodimers, in which two different fusion molecules are linked to each other by one or more covalent linkages, e.g. disulfide bond(s). Such bifunctional structures might be advantageous in that they are able to cross-link the same or different Ig$\epsilon$R(s) with different inhibitory receptors.

Receptor binding can be tested using any known assay method, such as competitive binding assays, direct and indirect sandwich assays. Thus, the binding of Fc $\gamma_1$ polypeptide included in the fusion molecules herein to a low-affinity IgG inhibitory receptor, or the binding of Fc$\epsilon$ polypeptide included herein to a high-affinity or low-affinity IgE receptor can be tested using conventional binding assays, such as competitive binding assays, including RIAs and ELISAs. Ligand/receptor complexes can be identified using traditional separation methods as filtration, centrifugation, flow cytometry, and the results from the binding assays can be analyzed using any conventional graphical representation of the binding data, such as Scatchard analysis. The assays may be performed, for example, using a purified receptor, or intact cells expressing the receptor. One or both of the binding partners may be immobilized and/or labeled. A particular cell-based binding assay is described in the Example below.

In one embodiment, the IgE constant region sequence is directly functionally connected to the $\gamma$hinge sequence of the Fc$\gamma$1 constant region.

In another embodiment, the Fc$\epsilon$ and the Fc$\gamma$1 polypeptide sequences may be connected by a polypeptide linker replacing the hinge region of the IgG1 fragment or in addition to the hinge region. The polypeptide linker functions as a "spacer" whose function is to separate the Fc$\gamma$ receptor binding domain and the Fc$\epsilon$ receptor binding domain so that they can independently assume their proper tertiary conformation. The polypeptide linker usually comprises between about 1 and about 25 residues or from about 2 to about 25 residues. The polypeptide linker may contain at least about 10, or at least about 15 amino acids. The polypeptide linker may be composed of amino acid residues which together provide a hydrophilic, relatively unstructured region. Linking amino acid sequences with little or no secondary structure work well. The specific amino acids in the spacer can vary, however, cysteines should be avoided. Suitable polypeptide linkers are, for example, disclosed in WO 88/09344 (published on Dec. 1, 1988), as are methods for the production of multifunctional proteins comprising such linkers.

The IgG1 and IgE constant region sequences may connected by a non-polypeptide linker. Such linkers may, for example, be residues of covalent bifunctional cross-linking agents capable of linking the two sequences without the impairment of the receptor (antibody) binding function. The bifunctional cross-linking reagents can be divided according to the specificity of their functional groups, e.g. amino, sulf-hydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group (for review, see Ji, T. H. "Bifunctional Reagents" in: Meth. Enzymol. 91:580-609 (1983)).

In a further specific embodiment, the two polypeptide sequences (including variants of the native sequences) are dimerized by amphiphilic helices. It is known that recurring copies of the amino acid leucine (Leu) in gene regulatory proteins can serve as teeth that "zip" two protein molecules together to provide a dimer. For further details about leucine zippers, which can serve as linkers for the purpose of the present invention, see for example: Landschulz, W. H., et al. *Science* 240:1759-1764 (1988); O'Shea, E. K. et al., *Science* 243: 38-542 (1989); McKnight, S. L., *Scientific American* 54-64, April 1991; Schmidt-Dorr. T. et al., *Biochemistry* 30:9657-9664 (1991); Blondel, A. and Bedouelle, H. *Protein Engineering* 4:457-461 (1991), and the references cited in these papers.

In a different approach, the two polypeptide sequences (including variants of the native sequences) are linked via carbohydate-directed bifunctional cross-linking agents, such as those disclosed in U.S. Pat. No. 5,329,028.

The cross-linking of an inhibitory receptor expressed on mast cells and/or basophils, such as IgG inhibitory receptors, e.g. Fc$\gamma$RIIb to a high-affinity IgE receptor, e.g. Fc$\epsilon$RI or low-affinity IgE receptor, e.g. Fc$\epsilon$RII, inhibits Fc$\epsilon$R mediated biological responses. Such biological responses are the mediation of an allergic reactions or autoimmune reactions via Fc$\epsilon$R, including, without limitation, conditions associated with IgE mediated reactions, such as, for example, asthma, allergic rhinitis, food allergies, chronic urticaria and angioedema, allergic reactions to hymenophthera (e.g. bee and yellow jacket) stings or medications such as penicillin up to and including the severe physiological reaction of anaphylactic shock.

2. Preparation of the Fusion Molecules

When the fusion molecules are polypeptides, in which the Fc$\epsilon$ and Fc$\gamma$1 polypeptide sequences are directly fused or functionally connected by a polypeptide linker, they can be prepared by well known methods of recombinant DNA technology or traditional chemical synthesis. If the polypeptides are produced by recombinant host cells, cDNA encoding the desired polypeptide of the present invention is inserted into a replicable vector for cloning and expression. As discussed before, the nucleotide and amino acid sequences of native immunoglobulin constant regions, including native IgG and IgE constant region sequences, are well known in the art and are readily available, for example, from Kabat et al., *Sequences of Proteins of Immunological Interest*, 5th Ed. Public Health Service, National Institute of Health, Bethesda, Md. (1991).

Suitable vectors are prepared using standard techniques of recombinant DNA technology, and are, for example, described in "Molecular Cloning: A Laboratory Manual", 2nd edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4 h edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991). Isolated plasmids and DNA fragments are cleaved, tailored, and ligated together in a specific order to generate the desired vectors. After ligation, the vector containing the gene to be expressed is transformed into a suitable host cell.

Host cells can be any eukaryotic or prokaryotic hosts known for expression of heterologous proteins. Accordingly, the polypeptides of the present invention can be expressed in eukaryotic hosts, such as eukaryotic microbes (yeast) or cells isolated from multicellular organisms (mammalian cell cultures), plants and insect cells. Examples of mammalian cell lines suitable for the expression of heterologous polypeptides include monkey kidney CV1 cell line transformed by SV40 (COS-7, ATCC CRL 1651); human embryonic kidney cell line 293S (Graham et al, J. Gen. Virol. 36:59 [1977]); baby hamster kidney cells (BHK, ATCC CCL 10); Chinese hamster ovary (CHO) cells (Urlaub and Chasin, *Proc. Natl. Acad. Sci. USA* 77:4216 [1980]; monkey kidney cells (CV1-76, ATCC CCL 70); African green monkey cells (VERO-76, ATCC CRL-1587); human cervical carcinoma cells (HELA, ATCC CCL 2); canine kidney cells (MDCK, ATCC CCL 34); human lung cells (W138, ATCC CCL 75); and human liver cells (Hep G2, HB 8065). In general myeloma cells, in particular those not producing any endogenous antibody, e.g. the non-immunoglobulin producing myelome cell line SP2/0, may be used for the production of the fusion molecules herein.

Eukaryotic expression systems employing insect cell hosts may rely on either plasmid or baculoviral expression systems. The typical insect host cells are derived from the fall army worm (*Spodoptera frugiperda*). For expression of a foreign protein these cells are infected with a recombinant form of the baculovirus *Autographa californica* nuclear polyhedrosis virus which has the gene of interest expressed under the control of the viral polyhedrin promoter. Other insects infected by this virus include a cell line known commercially as "High 5" (Invitrogen) which is derived from the cabbage looper (*Trichoplusia ni*). Another baculovirus sometimes used is the *Bombyx mori* nuclear polyhedorsis virus which infect the silk worm (*Bombyx mori*). Numerous baculovirus expression systems are commercially available, for example, from Invitrogen (Bac-N-Blue™), Clontech (BacPAK™ Baculovirus Expression System), Life Technologies (BAC-TO-BAC™), Novagen (Bac Vector System™), Pharmingen and Quantum Biotechnologies). Another insect cell host is common fruit fly, Drosophila melanogaster, for which a transient or stable plasmid based transfection kit is offered commercially by Invitrogen (The DES™ System).

*Saccharomyces cerevisiae* is the most commonly used among lower eukaryotic hosts. However, a number of other genera, species, and strains are also available and useful herein, such as *Pichia pastoris* (EP 183,070; Sreekrishna et al., *J. Basic Microbiol.* 28:165-278 (1988)). Yeast expression systems are commercially available, and can be purchased, for example, from Invitrogen (San Diego, Calif.). Other yeasts suitable for bi-functional protein expression include, without limitation, *Kluyveromyces* hosts (U.S. Pat. No. 4,943,529), e.g. *Kluyveromyces lactis*; *Schizosaccharomyces pombe* (Beach and Nurse, Nature 290:140 (1981); *Aspergillus* hosts, e.g. *A. niger* (Kelly and Hynes, *EMBO J.* 4:475-479 (1985])) and *A. nidulans* (Ballance et al., *Biochem. Biophys. Res. Commun.* 112:284-289 (1983)), and *Hansenula* hosts, e.g. *Hansenula polymorpha*. Yeasts rapidly grow on inexpensive (minimal) media, the recombinant can be easily selected by complementation, expressed proteins can be specifically engineered for cytoplasmic localization or for extracellular export, and they are well suited for large-scale fermentation.

Prokaryotes may be hosts for the initial cloning steps, and are useful for rapid production of large amounts of DNA, for production of single-stranded DNA templates used for site-directed mutagenesis, for screening many mutants simultaneously, and for DNA sequencing of the mutants generated. *E. coli* strains suitable for the production of the peptides of the present invention include, for example, BL21 carrying an inducible T7 RNA polymerase gene (Studier et al., *Methods Enzymol.* 185:60-98 (1990)); AD494 (DE3); EB105; and CB (*E. coli* B) and their derivatives; K12 strain 214 (ATCC 31,446); W3110 (ATCC 27,325); X1776 (ATCC 31,537); HB101 (ATCC 33,694); JM101 (ATCC 33,876); NM522 (ATCC 47,000); NM538 (ATCC 35,638); NM539 (ATCC 35,639), etc. Many other species and genera of prokaryotes may be used as well. Indeed, the peptides of the present invention can be readily produced in large amounts by utilizing recombinant protein expression in bacteria, where the peptide is fused to a cleavable ligand used for affinity purification.

Suitable promoters, vectors and other components for expression in various host cells are well known in the art and are disclosed, for example, in the textbooks listed above.

Whether a particular cell or cell line is suitable for the production of the polypeptides herein in a functionally active form, can be determined by empirical analysis. For example, an expression construct comprising the coding sequence of the desired molecule may be used to transfect a candidate cell line. The transfected cells are then grown in culture, the medium collected, and assayed for the presence of secreted polypeptide. The product can then be quantitated by methods known in the art, such as by ELISA with an antibody specifically binding the IgG, IgE portion of the molecule.

In certain instances, especially if the two polypeptide sequences making up the bifunctional molecule of the present invention are connected with a non-polypeptide linker, it may be advantageous to individually synthesize the IgE and IgG1 polypeptide sequences, e.g. by any of the recombinant approaches discussed above, followed by functionally linking the two sequences.

Alternatively, the two polypeptide sequences, or the entire molecule, may be prepared by chemical synthesis, such as solid phase peptide synthesis. Such methods are well known to those skilled in the art. In general, these methods employ either solid or solution phase synthesis methods, described in basic textbooks, such as, for example, J. M. Stewart and J. D. Young, *Solid Phase Peptide Synthesis*, 2nd Ed., Pierce Chemical Co., Rockford, Ill. (1984) and G. Barany and R. B. Merrifield, *The Peptide: Analysis Synthesis, Biology*, editors E. Gross and J. Meienhofer, Vol. 2, Academic Press, New York, (1980), pp. 3-254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis.

The fusion molecules of the present invention may include amino acid sequence variants of native immunoglobulin (e.g. IgG and/or IgE). Such amino acid sequence variants can be produced by expressing the underlying DNA sequence in a suitable recombinant host cell, or by in vitro synthesis of the desired polypeptide, as discussed above. The nucleic acid sequence encoding a polypeptide variant may be prepared by site-directed mutagenesis of the nucleic acid sequence encoding the corresponding native (e.g. human) polypeptide. Site-directed mutagenesis using polymerase chain reaction (PCR) amplification may be used.(see, for example, U.S. Pat. No. 4,683,195 issued Jul. 28, 1987; and *Current Protocols In Molecular Biology*, Chapter 15 (Ausubel et al., ed., 1991). Other site-directed mutagenesis techniques are also well known in the art and are described, for example, in the following publications: Current Protocols In Molecular Biology, supra, Chapter 8; *Molecular Cloning: A Laboratory Manual.*, 2nd edition (Sambrook et al., 1989); Zoller et al., *Methods Enzymol.* 100:468-500 (1983); Zoller & Smith, DNA 3:479-488 (1984); Zoller et al., Nucl. Acids Res., 10:6487 (1987); Brake et al., *Proc. Natl. Acad. Sci.* USA 81:4642-4646 (1984); Botstein et al., Science 229:1193 (1985); Kunkel et al., *Methods Enzymol.* 154:367-82 (1987), Adelman et al., *DNA* 2:183 (1983); and Carter et al., *Nucl. Acids Res.,* 13:4331 (1986). Cassette mutagenesis (Wells et al., *Gene* 34:315 [1985]), and restriction selection mutagenesis (Wells et al., *Philos. Trans. R. Soc. London SerA,* 317:415 [1986]) may also be used.

Amino acid sequence variants with more than one amino acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g. separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

The polypeptides of the invention can also be prepared by the combinatorial peptide library method disclosed, for example, in International Patent Publication PCT WO 92/09300. This method is particularly suitable for preparing and analyzing a plurality of molecules, that are variants of given predetermined sequences, and is, therefore, particularly useful in identifying polypeptides with improved biological properties, which can then be produced by any technique known in the art, including recombinant DNA technology and/or chemical synthesis.

3. Therapeutic Uses of the Fusion Molecules of the Invention

The present invention provides a new therapeutic strategy for treating immediate hypersensitivity diseases mediated through the high-affinity IgE receptor. In particular, the invention provides compounds for use in the treatment of both allergic diseases where IgE bridging of FcεR receptors occurs and autoimmune disorders where autoantibodies bind to the FcεR.

4. Nature of the Diseases Targeted

Following the Gell and Coombs Classification, allergic reactions are classified depending on the type of immune response induced and the resulting tissue damage that develops as a result of reactivity to an antigen. A Type I reaction (immediate hypersensitivity) occurs when an antigen (called an allergen in this case) entering the body encounters mast cells or basophils which are sensitized as a result of IgE to that antigen being attached to its high-affinity receptor, FcεRI. Upon reaching the sensitized mast cell, the allergen cross-links IgE bound to FcεRI, causing an increase in intracellular calcium ($Ca^{2+}$) that triggers the release of pre-formed mediators, such as histamine and proteases, and newly synthesized, lipid-derived mediators such as leukotrienes and prostaglandins. These autocoids produce the acute clinical symptoms of allergy. The stimulated basophils and mast cells will also produce and release proinflammatory mediators, which participate in the acute and delayed phase of allergic reactions.

As discussed before, a large variety of allergens has been identified so far, and new allergens are identified, cloned and sequenced practically every day.

Ingestion of an allergen results in gastrointestinal and systemic allergic reactions. The most common food allergens involved are peanuts, shellfish, milk, fish, soy, wheat, egg and tree nuts such as walnuts. In susceptible people, these foods can trigger a variety of allergic symptoms, such as nausea, vomiting, diarrhea, urticaria, angioedema, asthma and full-blown anaphylaxis. Inhalation of airborne allergens results in allergic rhinitis and allergic asthma, which can be acute or chronic depending on the nature of the exposure(s). Exposure to airborne allergens in the eye results in allergic conjunctivitis. Common airborne allergens includes pollens, mold spores, dust mites and other insect proteins that are the most frequent cause of seasonal hay fever and allergic asthma.

Cutaneous exposure to an allergen, e.g. natural rubber latex proteins as found in latex gloves, may result in local allergic reactions manifest as hives (urticaria) at the places of contact with the allergen.

Systemic exposure to an allergen such as occurs with a bee sting, the injection of penicillin, or the use of natural rubber latex (NRL) gloves inside a patient during surgery may result in, cutaneous, gastrointestinal and respiratory reactions up to and including airway obstruction and full blown anaphylaxis. Hymenoptera stings are insects that commonly cause allergic reactions, often leading the anaphylactic shock. Examples include various bees including honeybees, yellow jackets, yellow hornets, wasps and white-faced hornets. Certain ants known as fire ants (*Solenopsis invicta*) are an increasing cause of allergy in the US as they expand their range in this country. Proteins in NRL gloves have become an increasing concern to health care workers and patients and at present, there is no successful form of therapy for this problem except avoidance.

5. Uses of Compounds for Targeted Diseases

The compounds disclosed herein can be used to acutely or chronically inhibit IgE mediated reaction to major environmental and occupational allergens, can be used to provide protection for allergy vaccination (immunotherapy) to induce a state of non-allergic reactivity during treatment for specific allergens and can also have a prophylactic effect against allergic disease by preventing allergic sensitization to environmental and occupational allergens when administered to at-risk individuals (e.g., those at genetic risk of asthma and those exposed to occupational allergens in the workplace).

The bifunctional epsilon-gamma compounds described can be used to prevent allergic reactions to any specific allergen or group of allergens. By occupying a critical number of FcεRI receptors, these molecules will inhibit the ability of basophils and mast cells to react to any allergen so as to prevent including, without limitation, asthma, allergic rhinitis, atopic dermatitis, food allergies, urticaria, angioedema, up to and including anaphylactic shock. Thus these compounds could be used acutely to desensitize a patient so that the administration of a therapeutic agent (e.g. penicillin) can be given safely. Similarly, they can be used to desensitize a patient so that standard allergen vaccination may be given with greater safety, e.g. peanut or latex treatment. They can also be used as chronic therapy to prevent clinical reactivity to prevent environmental allergens such as foods or inhalant allergens.

In addition, the chimeric epsilon-gamma compounds herein hold great promise for the treatment of chronic urticaria and angioedema. Urticaria is a skin symptom that may accompany allergies but often is idiopathic. It is a relatively common disorder caused by localized cutaneous mast cell degranulation, with resultant increased dermal vascular permeability culminating in pruritic wheals. Angioedema is a vascular reaction involving the deep dermis or subcutaneous or submucosal tissues caused by localized mast cell degranulation. This results in tissue swelling that is pruritic or painful. Chronic urticaria and angioedema often occur together although they occur individually as well. These conditions are common and once present for more than six months, they often last a decade or more. Although not fatal, they are very troubling to patients as the frequent recurring attaching disrupt daily activities and thereby result in significant morbidity. Standard therapy is often unsuccessful in these conditions and they are distressing to the point that chemotherapy with cyclosporine and other potent immunosuppressive drugs has recently been advocated. Increasing evidence suggests that as many as 60% of patients with these conditions actually have an autoimmune disease, in which they make functional antibodies against the FcεRI receptor. For further details, see Hide et al., N. Engl. J. Med. 328:1599-1604 (1993); Fiebiger et al., J. Clin. *Invest.* 96:2606-12 (1995); Fiebiger et a., *J. Clin. Invest.* 101:243-51 (1998); Kaplan, A. P., Urticaria and Angioedema, In: *Inflammation: Basic Principles and Clinical Correlates* (Galliin and Snyderman eds.), 3rd Edition, Lippincott & Wilkins, Philadelphia, 1999, pp. 915-928. The fusion molecules of the present invention are believed to form the basis for a novel and effective treatment of these diseases by safely blocking access to the FcεRI.

In addition the chimeric epsilon-gamma compounds herein may be used for the treatment of inflammatory arthritis, e.g. rheumatoid arthritis or other autoimmune conditions depending on the role of mast cells and basophils in those diseases. Mast cells have been historically thought of primarily as a critical component of IgE-mediated allergic diseases through degranulation and cytokine production triggered by allergen driven aggregation of IgE bound to the high affinity IgE receptor (FcεRI). More recent studies have provided evidence that mast cells also may play a key role in autoimmune disease and especially those with autoantibody-dependent immune pathology. Activation and subsequent degranulation of mast cells via FcεRI cross-linking and anaphylatoxins generated through complement pathways are thought to be important for these processes. Thus prevention and/or inhibition of mast cell activation, degranulation and cytokine production provide a potential therapeutic target in autoimmune diseases such as inflammatory arthritis (Benoist and Mathis *Arthritis Res.* 2000 vol. 2:90-94). In addition to inflammatory arthritis, mast cells appear to be very important in experimental allergic encephalomyelitis (EAE), multiple sclerosis, and certain type of autoimmune skin disease such as bullous pemphigoid.

6. Compositions and Formulations of the Invention

For therapeutic uses, including prevention, the compounds of the invention can be formulated as pharmaceutical compositions in admixture with pharmaceutically acceptable carriers or diluents. Methods for making pharmaceutical formulations are well known in the art.

Techniques and formulations generally may be found in *Remington's Pharmaceutical Sciences,* 18th Edition, Mack Publishing Co., Easton, Pa. 1990. See, also, Wang and Hanson "Parenteral Formulations of Proteins and Peptides: Stability and Stabilizers", *Journal of Parenteral Science and Technology, Technical Report No.* 10, Supp. 42-2S (1988). A suitable administration format can best be determined by a medical practitioner for each patient individually.

Pharmaceutical compositions of the present invention can comprise a fusion molecule of the present invention along with conventional carriers and optionally other ingredients.

Suitable forms, in part, depend upon the use or the route of entry, for example oral, transdermal, inhalation, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms that prevent the agent or composition from exerting its effect.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical compositions can be administered by different routes including, but not limited to, oral, intravenous, intra-arterial, intraperitoneal, subcutaneous, intranasal or intrapulmonary routes. The desired isotonicity of the compositions can be accomplished using sodium chloride or other pharmaceutically acceptable agents such as dextrose, boric acid, sodium tartrate, propylene glycol, polyols (such as mannitol and sorbitol), or other inorganic or organic solutes.

For systemic administration, injection may be used e.g., intramuscular, intravenous, intra-arterial, etc. For injection, the compounds of the invention are formulated in liquid solutions, such as in physiologically compatible buffers such as Hank's solution or Ringer's solution. Alternatively, the compounds of the invention are formulated in one or more excipients (e.g., propylene glycol) that are generally accepted as safe as defined by USP standards. They can, for example, be suspended in an inert oil, suitably a vegetable oil such as sesame, peanut, olive oil, or other acceptable carrier.

They are suspended in an aqueous carrier, for example, in an isotonic buffer solution at pH of about 5.6 to 7.4. These compositions can be sterilized by conventional sterilization techniques, or can be sterile filtered. The compositions can contain pharmaceutically acceptable auxiliary substances as required to approximate physiological conditions, such as pH buffering agents. Useful buffers include for example, sodium acetate/acetic acid buffers. A form of repository or "depot" slow release preparation can be used so that therapeutically effective amounts of the preparation are delivered into the bloodstream over many, hours or days following transdermal injection or delivery. In addition, the compounds can be formulated in solid form and redissolved or suspended immediately prior to use. Lyophilized forms are also included.

Alternatively, certain molecules identified in accordance with the present invention can be administered orally. For oral administration, the compounds are formulated into conventional oral dosage forms such as capsules, tablets and tonics.

Systemic administration can also be by transmucosal or transdermal. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be, for example, through nasal sprays or using suppositories.

One route for administration of the compounds of the invention may be inhalation for intranasal and/or intrapulmonary delivery. For administration by inhalation, usually inhalable dry powder compositions or aerosol compositions are used, where the size of the particles or droplets is selected to ensure deposition of the active ingredient in the desired part of the respiratory tract, e.g. throat, upper respiratory tract or lungs. Inhalable compositions and devices for their administration are well known in the art. For example, devices for the delivery of aerosol medications for inspiration are known. One such device is a metered dose inhaler that delivers the same dosage of medication to the patient upon each actuation of the device. Metered dose inhalers typically include a canister containing a reservoir of medication and propellant under pressure and a fixed volume metered dose chamber. The canister is inserted into a receptacle in a body or base having a mouthpiece or nosepiece for delivering medication to the patient. The patient uses the device by manually pressing the canister into the body to close a filling valve and capture a metered dose of medication inside the chamber and to open a release valve which releases the captured, fixed volume of medication in the dose chamber to the atmosphere as an aerosol mist. Simultaneously, the patient inhales through the mouthpiece to entrain the mist into the airway. The patient then releases the canister so that the release valve closes and the filling valve opens to refill the dose chamber for the next administration of medication. See, for example, U.S. Pat. No. 4,896,832 and a product available from 3M Healthcare known as Aerosol Sheathed Actuator and Cap.

Another device is the breath actuated metered dose inhaler that operates to provide automatically a metered dose in response to the patient's inspiratory effort. One style of breath actuated device releases a dose when the inspiratory effort moves a mechanical lever to trigger the release valve. Another style releases the dose when the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978.

Devices also exist to deliver dry powdered drugs to the patient's airways (see, e.g. U.S. Pat. No. 4,527,769) and to deliver an aerosol by heating a solid aerosol precursor material (see, e.g. U.S. Pat. No. 4,922,901). These devices typically operate to deliver the drug during the early stages of the patient's inspiration by relying on the patient's inspiratory flow to draw the drug out of the reservoir into the airway or to actuate a heating element to vaporize the solid aerosol precursor.

Devices for controlling particle size of an aerosol are also known, see, for example, U.S. Pat. Nos. 4,790,305; 4,926,852; 4,677,975; and 3,658,059.

For topical administration, the compounds of the invention are formulated into ointments, salves, gels, or creams, as is generally known in the art.

If desired, solutions of the above compositions can be thickened with a thickening agent such as methyl cellulose. They can be prepared in emulsified form, either water in oil or oil in water. Any of a wide variety of pharmaceutically acceptable emulsifying agents can be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components can be mixed simply in a blender or other standard device to produce a concentrated mixture which can then be adjusted to the final concentration and viscosity by the addition of water or thickening agent and possibly a buffer to control pH or an additional solute to control tonicity.

The amounts of various compounds for use in the methods of the invention to be administered can be determined by standard procedures. Generally, a therapeutically effective amount is between about 100 mg/kg and $10^{-12}$ mg/kg depending on the age and size of the patient, and the disease or disorder associated with the patient. Generally, it is an amount between about 0.05 and 50 mg/kg, or between about 1.0 and 10 mg/kg for the individual to be treated. The determination of the actual dose is well within the skill of an ordinary physician.

The compounds of the present invention may be administered in combination with one or more further therapeutic agents for the treatment of IgE-mediated allergic diseases or conditions.

Such further therapeutic agents include, without limitation, corticosteroids, beta-antagonists, theophylline, leukotriene inhibitors, allergen vaccination, and biologic response modifiers such as soluble recombinant human soluble IL-4 receptors (Immunogen), and therapies that target Toll-like receptors. (see, e.g. Barnes, *The New England Journal of Medicine* 341:2006-2008 (1999)). Thus the compounds of the present invention can be used to supplement traditional allergy therapy, such as corticosteroid therapy performed with inhaled or oral corticosteroids.

7. Articles of Manufacture

The invention also provides articles of manufacture comprising the single-chain fusion compounds herein The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The container may also be an inhalation device such as those discussed above. At least one active agent in the composition is a fusion compound of the invention. The label or package insert indicates that the composition is used for treating the condition of choice, such as an allergic condition, e.g. asthma or any of the IgE-mediated allergies discussed above. The article of manufacture may further comprise a further container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Further details of the invention are illustrated by the following non-limiting Examples.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control.

EXAMPLES

Example 1

Construction and Expression

Construction of the Fcγ-Fcε gene from genomic DNA and Fcγ-Fcε (GE2) fusion protein expression were previously described (Zhu et al., (2002) *Nat Med* 8, 518-21). The Fcγ-Fcε protein consists of a hemagglutinin A (HA) epitope, 7 vector amino acids, the IgG1 hinge-CH2-CH3, a 17 amino acids including a (Gly$_4$Ser)$_3$ linker, and IgE CH2-CH3-CH4 (See FIGS. 7A and B; SEQ ID NO:7 AND 8).

E2G protein:

To minimize the antibody response to the foreign protein sequence of the linker and maintain the flexibility between the epsilon and gamma regions, we constructed a Fcε-Fcγ gene encoding the protein "E2G" in which the position of the epsilon and gamma genes were exchanged and all other sequences were removed except a Bgl II site at the site which links IgE CH3 to the IgG1 hinge. The HA tag, vector sequences, and (Gly$_4$Ser)$_3$ linker of GE2 were removed. Overlap PCR was used to add the 5' kappa leader sequence to the IgE CH2 sequence and replace-the IgE stop codon in CH4 with a Bgl II site. The two overlapping leader sequence primers were 5'-AAG CTT GAT ATC CAC CAT GGA GAC AGA CAC ACT CCT GCT ATG GGT ACT GCT GCT CTG GGT TCC AGG TTC CAC TGG TGA C-3' (SEQ ID NO:15) which contained a EcoRV site at the 5' end and 5'TCC AGG TTC CAC TGG TGA CTT CAC CCC GCC CAC CGT GAA GAT TTT ACA GTC GTC CTG CGA CGG C-3' (SEQ ID NO:16) and the CH4 3' primer was 5'-GGT ACC AGA TCT TTT ACC GGG ATT TAC AGA CAC C-3' (SEQ ID NO:17). The amplified product was cloned into the PCR 4.0 vector and sequenced. The EcoRV-Bgl II product was inserted into a plasmid containing a Bgl II site at the beginning of the IgG1 hinge (provided by S. L. Morrison). The final expression vector was made using a three way ligation between EcoRV-Nsi I of the E2G sequence and two fragments Nsi I-Bam HI and Bam HI-EcoRV from a plasmid containing the CMV promoter (provided by S. L. Morrison). FIGS. 8A and 8B show the amino acid sequence of the E2G fusion molecule (SEQ ID NO:19).

The following two constructs provide examples of how mutant or variant polypeptides could be generated. A substitution from serine to alanine at position 267 (EU index) within the CH2 domain of human IgG1 has been shown to increase the binding affinity of IgG1 to FcγRIIb, a low affinity Fcγ receptor with an immunoreceptor tyrosine-based inhibitory motif (Shields et al., (2001). *J Biol Chem* 276, 6591-604). We used nested PCR to introduce this mutation into our Fcγ-Fcε gene at the same position within the IgG1 CH2 domain and named it GE2 S mutant (FIGS. 9A and B). The 5' primer containing a Bgl II site was 5'-GGC CAG ATC TGA GCC CAA ATC TTG T-3' (SEQ ID NO:9), the 3' primer containing a Sac II site was 5'-CCT CCC GCG GCT TTG TCT TGG C-3' (SEQ ID NO:10), and the 5' and 3' nested primers were 5'-TTG ACC TCA GGG TCT TCG TGT GCC ACG TCC ACC ACG CAT-3' (SEQ ID NO:11) and 5'-ATG CGT GGT GGT GGA CGT GGC ACA CGA AGA CCCTGA GGT CAA-3' (SEQ ID NO:12) respectively.

A substitution from histadine to alanine at position 268 (EU index) in CH2 of human IgG1 is known to increase affinity to FcγRIIb while decreasing its affinity to the activation receptor FcγRIIIA (Shields et al., (2001). *J Biol Chem* 276, 6591-604). We used the same nested PCR strategy to create the GE2 H mutant (FIGS. 10A and B) containing a histadine to alanine substitution at the corresponding position in the GE2 protein. The nested PCR primers were 5' primer 5'-TTG ACC TCA GGG TCT TCC GCG CTC ACG TCC ACC ACC ACG CAT-3' (SEQ ID NO:13)and 3' primer 5'-ATG CGT GGT GGT GGA CGT GAG CGC GGA AGA CCC TGA GGT CAA-3' (SEQ ID NO:14) (FIG. 10). For both mutants, the PCR product was cloned into the pCR4.0 vector (Invitrogen, Carlsbad, Calif.) and sequenced. Then the Bgl II-Sac II fragment was inserted into the Fcγ-Fcε plasmid using a 3-way ligation with the SacII-Not I gene fragment and the Bgl II-Not I backbone.

Each gene was transfected by electroporation into 2-4×10$^7$ Ns0/1 myeloma cells. The cells, including 2×10$^6$ cells for a no DNA control, were spun at 1000 rpm for 5 min and resuspended in 0.5 ml cold PBS and placed in a 0.4 cm electroporation cuvette (BioRad, Hercules, Calif.). 50 μl linearized plasmid DNA in PBS was added to the cuvette and incubated on ice for 10 min. The cells were pulsed with 200V, 960 μF and then set on ice for 10 min. Cells were washed in 10 ml Iscoves' Modified Dulbecco Media (IMDM, Irvine Scientific, Santa Ana, Calif.)+5% Supplemented Bovine Calf Serum (CS, Hyclone, Logan, Utah) and plated at 2×10$^6$ cells/plate in IMDM+10% calf serum. Two days later, the cells were fed with IMDM+10% CS+1 mg/ml geneticin (Invitrogen). Selective media was replenished after three days. Wells that contained colonies were tested by ELISA and metabolic labeling for production of the different GE2 or E2G proteins. Protein producing cells were grown in roller bottles and the protein was purified on a protein A-sepharose column (Sigma Aldrich, St. Louis, Mo.) by acid elution using citric acid pH 4.5 and glycine pH 2.5. 1 ml protein fractions were neutralized with 2 M Tris, pH 8.0 and then dialyzed against PBS.

Example 2

Flow Cytometry

Binding to FcεRI was assessed by flow cytometry on Ku812 cells that express FcεRI and FcγRII Cells were grown in IMDM+5% CS. For each sample, 10$^6$ cells were washed in 1 ml PBS, pH 7.4, spun at 2000 rpm for 5 min and the supernatant was removed. The cells were resuspended in 100 μl IMDM+10% CS with or without GE2 proteins at several concentrations and incubated at 4° C. for 1 hour. The cells were washed twice with 1 ml PBS and then incubated at 37° C. with 100 μl 10 μg/ml FITC labeled goat anti-human epsilon chain (Sigma) or 0.4 mg/ml FITC labeled human IgE control for 30 min at 4° C. Cells were washed 3 times in 1 ml PBS and resuspended in 500 μl 2% paraformaldhyde diluted in PBS. Samples were analyzed on a FACScan flow cytometer (Becton Dickinson Immnunocytometry Systems, San Jose, Calif.), gating out dead cells and debris. Protein binding was reported as the percentage of FITC positive cells detected by flow cytometry (FIG. 11).

Given the sequence differences and changes in domain positions of the GE2 proteins, we examined the ability of these proteins to bind to receptors on the human basophil-like cell line, Ku812. Ku812 expresses FcεRI and FcγRIIb but not FcγRIIA and FcγRIII on its surface (Saxon et al., (2004) *Current Opinion in Allergy & Clinical Immunology* 4, 563-568), (Blom et al., (1992) *Eur J Immunol* 22, 2025-32),(Blom et al., (1996) *Scand J Immunol* 44, 54-61). Using flow cytometry to detect cell surface binding of GE2 proteins to Ku812 cells, GE2 and E2G had similar binding profiles with approximately 70% of the cells detected by a FITC labeled anti-human epsilon chain antibody when incubated with 10 μg/ml protein.

Example 3

Passive Cutaneous Anaphylaxis

Mice expressing human FcεRI alpha but not murine FcεRI alpha (Dombrowicz et al., (1996) *Journal of Immunology* 157, 1645-1651.) (provided by J.-P. Kinet) were used to measure passive cutaneous anaphylaxis as described previously (Zhu et al., (2002). *Nat Med* 8, 518-21). The fur on the back of a mouse was shaved and various concentrations of GE2 proteins in 50 μl human cat allergic serum (#9632) diluted 1:5 were injected intradermally. Four hours later, the mouse was challenged intravenously with 200 μl 1% Evan's blue dye in saline containing 10 μg purified natural Fel D1 (Indoor Biotechnology Inc, Charlottesville, Va.). After 30 minutes, the mouse was sacrificed and the under surface of the skin examined. Passive cutaneous anaphylaxis was visualized by leakage of blue dye into the skin through dilated blood vessels at the site of injection.

GE2 has been shown to inhibit FcεRI-dependant passive cutaneous anaphylaxis in mice when co-administered with anti-NP IgE and challenged with NP-BSA as well as in mice pre-sensitized with cat allergic human serum and challenged with the native Fel d1 antigen (Zhang K. et al., (2004) *J Allergy Clin Immunol.* 114, 321-7) (Zhu D. et al., (2002) *Nat Med* 8, 518-21). E2G is more effective than GE2 in blocking PCA when locally co-administered intradermally with serum from a cat allergic patient (#9632) and the mouse challenged intravenously 4 hours later with Fel d1 antigen (FIG. 12). In the representative experiment shown, PCA reactivity was completely blocked when all three doses of E2G protein injections (5, 2.5 and 1 μg/ml) were given whereas GE2 appeared to completely block at only 5 and 2.5 μg/ml doses with a small amount of dye leakage at 1 μg/ml GE2. E2G appeared to be slightly more effective than GE2 when tested on other mice although the exact dose differences varied. GE2 S mutant and GE2 H mutant completely blocked PCA reactivity at 5 μg/ml, however, at lower doses both mutants displayed less inhibition of PCA reactivity than the original GE2 at concentrations of 1 μg/ml and 0.5 μg/ml (FIGS. 13 and 14). At the sites where serum but no treatment was given, a strong PCA reactivity was observed. In addition, we observed that human myeloma IgE at the high 5 μg/ml dose did not block the PCA response (FIGS. 12, 13 and 14).

Example 4

Histamine Release

Human basophils were isolated from the buffy coat of human blood as described (Zhu et al., 2002) *Nat Med* 8, 518-21). The basophils were sensitized overnight with 10 μg/ml NP-IgE. The next day 10 μg/ml of each of the mutants, IgE, or IgG were added to the basophils for 2 hours in the incubator at 37° C. Cells were washed and activated with optimal concentrations of NP-BSA for 30 minutes. Histamine release was measured as described previously (Kepley et al., (2000). *J Allergy Clin Immunol.* 106, 337-48.). Degranulation was measured as the percent histamine released.

We have previously shown that GE2 blocks FcεRI-mediated histamine release in human basophils in a time and dose dependant manner (Zhu et al., (2002). *Nat Med* 8, 518-21.). Now we compare the ability of GE2 and the other GE2 proteins to inhibit degranulation of human basophils sensitized with 10 μg/ml NP-IgE (FIG. 15). When tested on a single donor, 10 μg/ml GE2 and E2G appeared to have similar effectiveness in blocking histamine release by over 50%. The GE2 S mutant and GE2 H mutants were also able to inhibit degranulation when compared with NP-BSA antigen alone but were less effective than either GE2 or E2G in blocking NP-BSA activated degranulation. The nonspecific IgE and IgG controls did not affect the level of degranulation. Spontaneous histamine release was less than 10%.

While the present application has been described in the context of embodiments illustrated and described herein, the invention may be embodied in other specific ways or in other specific forms without departing from its spirit or essential characteristics. Therefore, the described embodiments are to be considered in all respects as illustrative and not restrictive. The scope of the invention is therefore indicated by the appended claims rather than the foregoing description, an all changes that come within the meaning and range of equivalency of the claims are to be embraced within their scope.

What is claimed is:

1. A fusion molecule comprising the polypeptide sequence CHε2-CHε3-CHε4-γhinge-CHγ2-CHγ3, wherein the sequence comprises the sequence of SEQ ID NO: 19.

* * * * *

SEQUENCE LISTING

<160> NUMBER OF SEQ ID NOS: 23

<210> SEQ ID NO 1
<211> LENGTH: 696
<212> TYPE: DNA
<213> ORGANISM: homo sapiens

<400> SEQUENCE: 1

```
gagcccaaat cttgtgacaa aactcacaca tgcccaccgt gcccagcacc tgaactcctg      60
gggggaccgt cagtcttcct cttccccca  aaacccaagg acaccctcat gatctcccgg     120 accctgagg  tcacatgcgt ggtggtggac gtgagccacg aagaccctga ggtcaagttc     180
aactggtacg tggacggcgt ggaggtgcat aatgttaaga caaagccgcg ggaggagcag     240
tacaacagca cgtaccgtgt ggtcagcgtc ctcaccgtcc tgcaccagaa ctggatgaat     300
```

```
ggaaaggagt acaagtgcaa ggtctccaac aaagccctcc cagcccccat cgagaaaacc    360
atctccaaag ccaaagtgca gccccgagaa ccacaggtgt acaccctgcc cccatcccgg    420
gatgagctga ccaagaacca ggtcagcctg acctgcctgg tcaaaggctt ctatcccagc    480
gacatcgccg tggagtggga gagcaatggg cagccggaga acaactacaa gaccacgcct    540
cccgtgctgg actccgtcgg ctccttcttc ctctacagca agctcaccgt ggacaagagc    600
aggtggcagc aggggaacgt cttctcatgc tccgtgatgc atgaggctct gcacaaccac    660
taccagcaga ggagcctctc cctgtctccg ggtaaa                              696
```

<210> SEQ ID NO 2
<211> LENGTH: 330
<212> TYPE: PRT
<213> ORGANISM: homo sapiens

<400> SEQUENCE: 2

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asn Trp Met Asn Gly Lys Glu Tyr Lys Cys Lys Val Ser Asn
        195                 200                 205

Lys Ala Leu Pro Ala Pro Ile Glu Lys Thr Ile Ser Lys Ala Lys Val
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Val Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Gln
305                 310                 315                 320

Gln Arg Ser Leu Ser Leu Ser Pro Gly Lys
                325                 330

<210> SEQ ID NO 3
<211> LENGTH: 232
<212> TYPE: PRT
<213> ORGANISM: homo sapiens

<400> SEQUENCE: 3

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Val Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asn Trp Met Asn Gly Lys Glu Tyr Lys Cys Lys Val Ser Asn Lys Ala
            100                 105                 110

Leu Pro Ala Pro Ile Glu Lys Thr Ile Ser Lys Ala Lys Val Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Val Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Gln Gln Arg
    210                 215                 220

Ser Leu Ser Leu Ser Pro Gly Lys
225                 230

<210> SEQ ID NO 4
<211> LENGTH: 1445
<212> TYPE: DNA
<213> ORGANISM: homo sapiens

<400> SEQUENCE: 4
tccacacaga gccatccgt cttcccttg acccgctgct gcaaaaacat tccctccaat      60
gccacctccg tgactctggg ctgcctggcc acgggctact tcccggagcc ggtgatggtg    120
acctgggaca caggctccct caacgggaca ctatgacct taccagccac acccctcacg    180
ctctctggtc actatgccac catcagcttg ctgaccgtct cgggtgcgtg ggccaagcag   240
atgttcacct gccgtgtggc acacactcca tcgtccacag actgggtcga caacaaaacc   300
ttcagcgtct gctccaggga cttcacccccg cccaccgtga agatcttaca gtcgtcctgc   360
```

-continued

```
gacggcggcg ggcacttccc cccgaccatc cagctcctgt gcctcgtctc tgggtacacc    420
ccagggacta tcaacatcac ctggctggag gacgggcagg tcatggacgt ggacttgtcc    480
accgcctcta ccacgcagga gggtgagctg gcctccacac aaagcgagct caccctcagc    540
cagaagcact ggctgtcaga ccgcacctac acctgccagg tcacctatca aggtcacacc    600
tttgaggaca gcaccaagaa gtgtgcagat tccaacccga gagggtgagc gcctaccta     660
agccggccca gcccgttcga cctgttcatc cgcaagtcgc ccacgatcac ctgtctggtg    720
gtggacctgg cacccagcaa ggggaccgtg aacctgacct ggtcccgggc cagtgggaag    780
cctgtgaacc actccaccag aaaggaggag aagcagcgca atggcacgtt aaccgtcacg    840
tccaccctgc cggtgggcac ccgagactgg atcgagggg agacctacca gtgcagggtg    900
acccacccc acctgcccag ggccctcatg cggtccacga ccaagaccag cggcccgcgt    960
gctgccccgg aagtctatgc gtttgcgacg ccggagtggc cggggagccg ggacaagcgc   1020
accctcgcct gcctgatcca gaacttcatg cctgaggaca tctcggtgca gtggctgcac   1080
aacgaggtgc agctcccgga cgcccggcac agcacgacgc agccccgcaa gaccaagggc   1140
tccggcttct tcgtcttcag ccgcctggag gtgaccaggg ccgaatggga gcagaaagat   1200
gagttcatct gccgtgcagt ccatgaggca gcgagcccct cacagaccgt ccagcgagcg   1260
gtgtctgtaa atcccggtaa atgacgtact cctgcctccc tccctcccag ggctccatcc   1320
agctgtgcag tggggaggac tggccagacc ttctgtccac tgttgcaatg accccaggaa   1380
gctaccccca ataaactgtg cctgctcaga gccccagtac acccattctt gggagcgggc   1440
agggc                                                                1445
```

<210> SEQ ID NO 5
<211> LENGTH: 427
<212> TYPE: PRT
<213> ORGANISM: homo sapiens

<400> SEQUENCE: 5

```
Ser Thr Gln Ser Pro Ser Val Phe Pro Leu Thr Arg Cys Cys Lys Asn
  1               5                  10                  15

Ile Pro Ser Asn Ala Thr Ser Val Thr Leu Gly Cys Leu Ala Thr Gly
             20                  25                  30

Tyr Phe Pro Glu Pro Val Met Val Thr Trp Asp Thr Gly Ser Leu Asn
         35                  40                  45

Gly Thr Thr Met Thr Leu Pro Ala Thr Thr Leu Thr Leu Ser Gly His
     50                  55                  60

Tyr Ala Thr Ile Ser Leu Leu Thr Val Ser Gly Ala Trp Ala Lys Gln
 65                  70                  75                  80

Met Phe Thr Cys Arg Val Ala His Thr Pro Ser Ser Thr Asp Trp Val
                 85                  90                  95

Asp Asn Lys Thr Phe Ser Val Cys Ser Arg Asp Phe Thr Pro Pro Thr
            100                 105                 110

Val Lys Ile Leu Gln Ser Ser Cys Asp Gly Gly Gly His Phe Pro Pro
        115                 120                 125

Thr Ile Gln Leu Leu Cys Leu Val Ser Gly Tyr Thr Pro Gly Thr Ile
    130                 135                 140

Asn Ile Thr Trp Leu Glu Asp Gly Gln Val Met Asp Val Asp Leu Ser
145                 150                 155                 160

Thr Ala Ser Thr Thr Gln Glu Gly Glu Leu Ala Ser Thr Gln Ser Glu
                165                 170                 175
```

```
Leu Thr Leu Ser Gln Lys His Trp Leu Ser Asp Arg Thr Tyr Thr Cys
            180                 185                 190

Gln Val Thr Tyr Gln Gly His Thr Phe Glu Asp Ser Thr Lys Lys Cys
            195                 200                 205

Ala Asp Ser Asn Pro Arg Gly Val Ser Ala Tyr Leu Ser Arg Pro Ser
210                 215                 220

Pro Phe Asp Leu Phe Ile Arg Lys Ser Pro Thr Ile Thr Cys Leu Val
225                 230                 235                 240

Val Asp Leu Ala Pro Ser Lys Gly Thr Val Asn Leu Thr Trp Ser Arg
            245                 250                 255

Ala Ser Gly Lys Pro Val Asn His Ser Thr Arg Lys Glu Glu Lys Gln
            260                 265                 270

Arg Asn Gly Thr Leu Thr Val Thr Ser Thr Leu Pro Val Gly Thr Arg
            275                 280                 285

Asp Trp Ile Glu Gly Glu Thr Tyr Gln Cys Arg Val Thr His Pro His
            290                 295                 300

Leu Pro Arg Ala Leu Met Arg Ser Thr Thr Lys Thr Ser Gly Pro Arg
305                 310                 315                 320

Ala Ala Pro Glu Val Tyr Ala Phe Ala Thr Pro Glu Trp Pro Gly Ser
            325                 330                 335

Arg Asp Lys Arg Thr Leu Ala Cys Leu Ile Gln Asn Phe Met Pro Glu
            340                 345                 350

Asp Ile Ser Val Gln Trp Leu His Asn Glu Val Gln Leu Pro Asp Ala
            355                 360                 365

Arg His Ser Thr Thr Gln Pro Arg Lys Thr Lys Gly Ser Gly Phe Phe
            370                 375                 380

Val Phe Ser Arg Leu Glu Val Thr Arg Ala Glu Trp Glu Gln Lys Asp
385                 390                 395                 400

Glu Phe Ile Cys Arg Ala Val His Glu Ala Ala Ser Pro Ser Gln Thr
            405                 410                 415

Val Gln Arg Ala Val Ser Val Asn Pro Gly Lys
            420                 425

<210> SEQ ID NO 6
<211> LENGTH: 320
<212> TYPE: PRT
<213> ORGANISM: homo sapiens

<400> SEQUENCE: 6

Phe Thr Pro Pro Thr Val Lys Ile Leu Gln Ser Ser Cys Asp Gly Gly
  1               5                  10                  15

Gly His Phe Pro Pro Thr Ile Gln Leu Leu Cys Leu Val Ser Gly Tyr
            20                  25                  30

Thr Pro Gly Thr Ile Asn Ile Thr Trp Leu Glu Asp Gly Gln Val Met
        35                  40                  45

Asp Val Asp Leu Ser Thr Ala Ser Thr Thr Gln Glu Gly Glu Leu Ala
    50                  55                  60

Ser Thr Gln Ser Glu Leu Thr Leu Ser Gln Lys His Trp Leu Ser Asp
65                  70                  75                  80

Arg Thr Tyr Thr Cys Gln Val Thr Tyr Gln Gly His Thr Phe Glu Asp
                85                  90                  95

Ser Thr Lys Lys Cys Ala Asp Ser Asn Pro Arg Gly Val Ser Ala Tyr
            100                 105                 110

Leu Ser Arg Pro Ser Pro Phe Asp Leu Phe Ile Arg Lys Ser Pro Thr
        115                 120                 125
```

```
Ile Thr Cys Leu Val Val Asp Leu Ala Pro Ser Lys Gly Thr Val Asn
    130                 135                 140
Leu Thr Trp Ser Arg Ala Ser Gly Lys Pro Val Asn His Ser Thr Arg
145                 150                 155                 160
Lys Glu Glu Lys Gln Arg Asn Gly Thr Leu Thr Val Thr Ser Thr Leu
                165                 170                 175
Pro Val Gly Thr Arg Asp Trp Ile Glu Gly Glu Thr Tyr Gln Cys Arg
            180                 185                 190
Val Thr His Pro His Leu Pro Arg Ala Leu Met Arg Ser Thr Thr Lys
        195                 200                 205
Thr Ser Gly Pro Arg Ala Ala Pro Glu Val Tyr Ala Phe Ala Thr Pro
    210                 215                 220
Glu Trp Pro Gly Ser Arg Asp Lys Arg Thr Leu Ala Cys Leu Ile Gln
225                 230                 235                 240
Asn Phe Met Pro Glu Asp Ile Ser Val Gln Trp Leu His Asn Glu Val
                245                 250                 255
Gln Leu Pro Asp Ala Arg His Ser Thr Thr Gln Pro Arg Lys Thr Lys
            260                 265                 270
Gly Ser Gly Phe Phe Val Phe Ser Arg Leu Glu Val Thr Arg Ala Glu
        275                 280                 285
Trp Glu Gln Lys Asp Glu Phe Ile Cys Arg Ala Val His Glu Ala Ala
    290                 295                 300
Ser Pro Ser Gln Thr Val Gln Arg Ala Val Ser Val Asn Pro Gly Lys
305                 310                 315                 320

<210> SEQ ID NO 7
<211> LENGTH: 1758
<212> TYPE: DNA
<213> ORGANISM: homo sapiens

<400> SEQUENCE: 7
tatccatatg atgttccaga ttatgctggg gcccagccgg ccagatctga gcccaaatct    60
tgtgacaaaa ctcacacatg cccaccgtgc ccagcacctg aactcctggg gggaccgtca   120
gtcttcctct tccccccaaa acccaaggac accctcatga tctcccggac ccctgaggtc   180
acatgcgtgg tggtggacgt gagccacgaa gaccctgagg tcaagttcaa ctggtacgtg   240
gacggcgtgg aggtgcataa tgccaagaca aagccgcggg aggagcagta caacagcacg   300
taccgggtgg tcagcgtcct caccgtcctg caccaggact ggctgaatgg caaggagtac   360
aagtgcaagg tctccaacaa agccctccca gcccccatcg agaaaaccat ctccaaagcc   420
aaagggcagc cccgagaacc acaggtgtac accctgcccc catcccggga tgagctgacc   480
aagaaccagg tcagcctgac ctgcctggtc aaaggcttct atcccagcga catcgccgtg   540
gagtgggaga gcaatgggca gccggagaac aactacaaga ccacgcctcc cgtgctggac   600
tccgacggct ccttcttcct ctacagcaag ctcaccgtgg acaagagcag gtggcagcag   660
gggaacgtct tctcatgctc cgtgatgcat gaggctctgc acaaccacta cacgcagaag   720
agcctctccc tgtctccggg taaagtcgag ggtggaggcg gttcaggcgg aggtggctct   780
ggcggtggcg gatcgttcac cccgcccacc gtgaagatct acagtcgtc ctgcgacggc   840
ggcgggcact ccccccgac catccagctc ctgtgcctcg tctctgggta caccccaggg   900
actatcaaca tcacctggct ggaggacggg caggtcatgg acgtggactt gtccaccgcc   960
tctaccacgc aggagggtga gctggcctcc acacaaagcg agctcaccct cagccagaag  1020
```

-continued

```
cactggctgt cagaccgcac ctacacctgc caggtcacct atcaaggtca cacctttgag    1080
gacagcacca agaagtgtgc agattccaac ccgagagggg tgagcgccta cctaagccgg    1140
cccagcccgt tcgacctgtt catccgcaag tcgcccacga tcacctgtct ggtggtggac    1200
ctggcaccca gcaaggggac cgtgaacctg acctggtccc gggccagtgg gaagcctgtg    1260
aaccactcca ccagaaagga ggagaagcag cgcaatggca cgttaaccgt cacgtccacc    1320
ctgccggtgg gcacccgaga ctggatcgag ggggagacct accagtgcag ggtgacccac    1380
ccccacctgc cagggccct catgcggtcc acgaccaaga ccagcggccc gcgtgctgcc    1440
ccggaagtct atgcgtttgc gacgccgag tggccgggga ccgggacaa gcgcaccctc    1500 gcctgcctga tccagaactt catgcctgag gacatctcgg tgcagtggct gcacaacgag    1560
gtgcagctcc cggacgcccg gcacagcacg acgcagcccc gcaagaccaa gggctccggc    1620
ttcttcgtct tcagccgtct agaggtgacc agggccgaat gggagcagaa agatgagttc    1680
atctgccgtg cagtccatga ggcagctagc ccctcacaga ccgtccagcg agcggtgtct    1740
gtaaatcccg gtaaatga                                                 1758
```

<210> SEQ ID NO 8
<211> LENGTH: 585
<212> TYPE: PRT
<213> ORGANISM: homo sapiens

<400> SEQUENCE: 8

```
Tyr Pro Tyr Asp Val Pro Asp Tyr Ala Gly Ala Gln Pro Ala Arg Ser
  1               5                  10                  15

Glu Pro Lys Ser Cys Asp Lys Thr His Thr Cys Pro Pro Cys Pro Ala
             20                  25                  30

Pro Glu Leu Leu Gly Gly Pro Ser Val Phe Leu Phe Pro Pro Lys Pro
         35                  40                  45

Lys Asp Thr Leu Met Ile Ser Arg Thr Pro Glu Val Thr Cys Val Val
 50                  55                  60

Val Asp Val Ser His Glu Asp Pro Glu Val Lys Phe Asn Trp Tyr Val
65                  70                  75                  80

Asp Gly Val Glu Val His Asn Ala Lys Thr Lys Pro Arg Glu Glu Gln
                 85                  90                  95

Tyr Asn Ser Thr Tyr Arg Val Val Ser Val Leu Thr Val Leu His Gln
            100                 105                 110

Asp Trp Leu Asn Gly Lys Glu Tyr Lys Cys Lys Val Ser Asn Lys Ala
        115                 120                 125

Leu Pro Ala Pro Ile Glu Lys Thr Ile Ser Lys Ala Lys Gly Gln Pro
    130                 135                 140

Arg Glu Pro Gln Val Tyr Thr Leu Pro Pro Ser Arg Asp Glu Leu Thr
145                 150                 155                 160

Lys Asn Gln Val Ser Leu Thr Cys Leu Val Lys Gly Phe Tyr Pro Ser
                165                 170                 175

Asp Ile Ala Val Glu Trp Glu Ser Asn Gly Gln Pro Glu Asn Asn Tyr
            180                 185                 190

Lys Thr Thr Pro Pro Val Leu Asp Ser Asp Gly Ser Phe Phe Leu Tyr
        195                 200                 205

Ser Lys Leu Thr Val Asp Lys Ser Arg Trp Gln Gln Gly Asn Val Phe
    210                 215                 220

Ser Cys Ser Val Met His Glu Ala Leu His Asn His Tyr Thr Gln Lys
225                 230                 235                 240
```

```
Ser Leu Ser Leu Ser Pro Gly Lys Val Glu Gly Gly Gly Ser Gly
            245                 250                 255
Gly Gly Gly Ser Gly Gly Gly Ser Phe Thr Pro Thr Val Lys
        260                 265                 270
Ile Leu Gln Ser Cys Asp Gly Gly His Phe Pro Pro Thr Ile
            275                 280                 285
Gln Leu Leu Cys Leu Val Ser Gly Tyr Thr Pro Gly Thr Ile Asn Ile
        290                 295                 300
Thr Trp Leu Glu Asp Gly Gln Val Met Asp Val Asp Leu Ser Thr Ala
305                 310                 315                 320
Ser Thr Thr Gln Glu Gly Glu Leu Ala Ser Thr Gln Ser Glu Leu Thr
            325                 330                 335
Leu Ser Gln Lys His Trp Leu Ser Asp Arg Thr Tyr Thr Cys Gln Val
            340                 345                 350
Thr Tyr Gln Gly His Thr Phe Glu Asp Ser Thr Lys Lys Cys Ala Asp
            355                 360                 365
Ser Asn Pro Arg Gly Val Ser Ala Tyr Leu Ser Arg Pro Ser Pro Phe
        370                 375                 380
Asp Leu Phe Ile Arg Lys Ser Pro Thr Ile Thr Cys Leu Val Val Asp
385                 390                 395                 400
Leu Ala Pro Ser Lys Gly Thr Val Asn Leu Thr Trp Ser Arg Ala Ser
            405                 410                 415
Gly Lys Pro Val Asn His Ser Thr Arg Lys Glu Glu Lys Gln Arg Asn
            420                 425                 430
Gly Thr Leu Thr Val Thr Ser Thr Leu Pro Val Gly Thr Arg Asp Trp
        435                 440                 445
Ile Glu Gly Glu Thr Tyr Gln Cys Arg Val Thr His Pro His Leu Pro
            450                 455                 460
Arg Ala Leu Met Arg Ser Thr Thr Lys Thr Ser Gly Pro Arg Ala Ala
465                 470                 475                 480
Pro Glu Val Tyr Ala Phe Ala Thr Pro Glu Trp Pro Gly Ser Arg Asp
            485                 490                 495
Lys Arg Thr Leu Ala Cys Leu Ile Gln Asn Phe Met Pro Glu Asp Ile
            500                 505                 510
Ser Val Gln Trp Leu His Asn Glu Val Gln Leu Pro Asp Ala Arg His
            515                 520                 525
Ser Thr Thr Gln Pro Arg Lys Thr Lys Gly Ser Gly Phe Phe Val Phe
            530                 535                 540
Ser Arg Leu Glu Val Thr Arg Ala Glu Trp Glu Gln Lys Asp Glu Phe
545                 550                 555                 560
Ile Cys Arg Ala Val His Glu Ala Ala Ser Pro Ser Gln Thr Val Gln
            565                 570                 575
Arg Ala Val Ser Val Asn Pro Gly Lys
            580                 585

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
ggccagatct gagcccaaat cttgt                                        25
```

```
<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
cctcccgcgg ctttgtcttg gc                                              22

<210> SEQ ID NO 11
<211> LENGTH: 42
<212> TYPE: DNA
<213> ORGANISM: Artificial Sequence
<220> FEATURE:
<223> OTHER INFORMATION: primer

<400> SEQUENCE: 11
ttgacctcag ggtcttcgtg tgccacgtcc accaccacgc at                        42

<210> SEQ ID NO 12
<211> LENGTH: 42
<212> TYPE: DNA
<213> ORGANISM: Artificial Sequence
<220> FEATURE:
<223> OTHER INFORMATION: primer

<400> SEQUENCE: 12
atgcgtggtg gtggacgtgg cacacgaaga ccctgaggtc aa                        42

<210> SEQ ID NO 13
<211> LENGTH: 42
<212> TYPE: DNA
<213> ORGANISM: Artificial Sequence
<220> FEATURE:
<223> OTHER INFORMATION: primer

<400> SEQUENCE: 13
ttgacctcag ggtcttccgc gctcacgtcc accaccacgc at                        42

<210> SEQ ID NO 14
<211> LENGTH: 42
<212> TYPE: DNA
<213> ORGANISM: Artificial Sequence
<220> FEATURE:
<223> OTHER INFORMATION: primer

<400> SEQUENCE: 14
atgcgtggtg gtggacgtga gcgcggaaga ccctgaggtc aa                        42

<210> SEQ ID NO 15
<211> LENGTH: 79
<212> TYPE: DNA
<213> ORGANISM: Artificial Sequence
<220> FEATURE:
<223> OTHER INFORMATION: primer

<400> SEQUENCE: 15
aagcttgata tccaccatgg agacagacac actcctgcta tgggtactgc tgctctgggt     60
tccaggttcc actggtgac                                                  79

<210> SEQ ID NO 16
<211> LENGTH: 64
<212> TYPE: DNA
<213> ORGANISM: Artificial Sequence
<220> FEATURE:
```

<223> OTHER INFORMATION: primer

<400> SEQUENCE: 16

```
tccaggttcc actggtgact tcaccccgcc caccgtgaag attttacagt cgtcctgcga   60
cggc                                                                64
```

<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17

```
ggtaccagat cttttaccgg gatttacaga cacc                               34
```

<210> SEQ ID NO 18
<211> LENGTH: 1665
<212> TYPE: DNA
<213> ORGANISM: homo sapiens

<400> SEQUENCE: 18

```
ttcaccccgc ccaccgtgaa gatcttacag tcgtcctgcg acggcggcgg gcacttcccc     60
ccgaccatcc agctcctgtg cctcgtctct gggtacaccc cagggactat caacatcacc    120
tggctggagg acgggcaggt catggacgtg gacttgtcca ccgcctctac cacgcaggag    180
ggtgagctgg cctccacaca aagcgagctc accctcagcc agaagcactg gctgtcagac    240
cgcacctaca cctgccaggt cacctatcaa ggtcacacct ttgaggacag caccaagaag    300
tgtgcagatt caacccgag aggggtgagc gcctaccta gccggcccag cccgttcgac     360
ctgttcatcc gcaagtcgcc cacgatcacc tgtctggtgg tggacctggc acccagcaag    420
gggaccgtga acctgacctg gtcccgggcc agtgggaagc tgtgaacca ctccaccaga     480
aaggaggaga agcagcgcaa tggcacgtta accgtcacgt ccaccctgcc ggtgggcacc    540
cgagactgga tcgaggggga gacctaccag tgcagggtga cccacccca cctgcccagg    600
gccctcatgc ggtccacgac caagaccagc ggcccgcgtg ctgccccgga agtctatgcg    660
tttgcgacgc cggagtggcc ggggagccgg acaagcgca ccctcgcctg cctgatccag    720
aacttcatgc ctgaggacat ctcggtgcag tggctgcaca cgaggtgca gctcccggac    780
gcccggcaca gcacgacgca gccccgcaag accaagggct ccggcttctt cgtcttcagc    840
cgtctagagg tgaccagggc cgaatgggag cagaaagatg agttcatctg ccgtgcagtc    900
catgaggcag ctagcccctc acagaccgtc cagcgagcgg tgtctgtaaa tcccggtaaa    960
agatctgagc ccaaatcttg tgacaaaact cacacatgcc caccgtgccc agcacctgaa   1020
ctcctggggg gaccgtcagt cttcctcttc cccccaaaac ccaaggacac cctcatgatc   1080
tcccggaccc ctgaggtcac atgcgtggtg gtggacgtga gccacgaaga ccctgaggtc   1140
aagttcaact ggtacgtgga cggcgtggag gtgcataatg ccaagacaaa gccgcgggag   1200
gagcagtaca acagcacgta ccgggtggtc agcgtcctca ccgtcctgca ccaggactgg   1260
ctgaatggca aggagtacaa gtgcaaggtc tccaacaaag ccctcccagc ccccatcgag   1320
aaaaccatct ccaaagccaa aggcagccc cgagaaccac aggtgtacac cctgccccca   1380
tcccgggatg agctgaccaa gaaccaggtc agcctgacct gcctggtcaa aggcttctat   1440
cccagcgaca tcgccgtgga gtgggagagc aatgggcagc cggagaacaa ctacaagacc   1500
acgcctcccg tgctggactc cgacggctcc ttcttcctct acagcaagct caccgtggac   1560
```

-continued

```
aagagcaggt ggcagcaggg gaacgtcttc tcatgctccg tgatgcatga ggctctgcac   1620
aaccactaca cgcagaagag cctctccctg tctccgggta aatga                  1665
```

<210> SEQ ID NO 19
<211> LENGTH: 554
<212> TYPE: PRT
<213> ORGANISM: homo sapiens

<400> SEQUENCE: 19

```
Phe Thr Pro Pro Thr Val Lys Ile Leu Gln Ser Ser Cys Asp Gly Gly
  1               5                  10                  15

Gly His Phe Pro Pro Thr Ile Gln Leu Leu Cys Leu Val Ser Gly Tyr
             20                  25                  30

Thr Pro Gly Thr Ile Asn Ile Thr Trp Leu Glu Asp Gly Gln Val Met
         35                  40                  45

Asp Val Asp Leu Ser Thr Ala Ser Thr Thr Gln Glu Gly Glu Leu Ala
     50                  55                  60

Ser Thr Gln Ser Glu Leu Thr Leu Ser Gln Lys His Trp Leu Ser Asp
 65                  70                  75                  80

Arg Thr Tyr Thr Cys Gln Val Thr Tyr Gln Gly His Thr Phe Glu Asp
                 85                  90                  95

Ser Thr Lys Lys Cys Ala Asp Ser Asn Pro Arg Gly Val Ser Ala Tyr
            100                 105                 110

Leu Ser Arg Pro Ser Pro Phe Asp Leu Phe Ile Arg Lys Ser Pro Thr
        115                 120                 125

Ile Thr Cys Leu Val Val Asp Leu Ala Pro Ser Lys Gly Thr Val Asn
    130                 135                 140

Leu Thr Trp Ser Arg Ala Ser Gly Lys Pro Val Asn His Ser Thr Arg
145                 150                 155                 160

Lys Glu Glu Lys Gln Arg Asn Gly Thr Leu Thr Val Thr Ser Thr Leu
                165                 170                 175

Pro Val Gly Thr Arg Asp Trp Ile Glu Gly Glu Thr Tyr Gln Cys Arg
            180                 185                 190

Val Thr His Pro His Leu Pro Arg Ala Leu Met Arg Ser Thr Thr Lys
        195                 200                 205

Thr Ser Gly Pro Arg Ala Ala Pro Glu Val Tyr Ala Phe Ala Thr Pro
    210                 215                 220

Glu Trp Pro Gly Ser Arg Asp Lys Arg Thr Leu Ala Cys Leu Ile Gln
225                 230                 235                 240

Asn Phe Met Pro Glu Asp Ile Ser Val Gln Trp Leu His Asn Glu Val
                245                 250                 255

Gln Leu Pro Asp Ala Arg His Ser Thr Thr Gln Pro Arg Lys Thr Lys
            260                 265                 270

Gly Ser Gly Phe Phe Val Phe Ser Arg Leu Glu Val Thr Arg Ala Glu
        275                 280                 285

Trp Glu Gln Lys Asp Glu Phe Ile Cys Arg Ala Val His Glu Ala Ala
    290                 295                 300

Ser Pro Ser Gln Thr Val Gln Arg Ala Val Ser Val Asn Pro Gly Lys
305                 310                 315                 320

Arg Ser Glu Pro Lys Ser Cys Asp Lys Thr His Thr Cys Pro Pro Cys
                325                 330                 335

Pro Ala Pro Glu Leu Leu Gly Gly Pro Ser Val Phe Leu Phe Pro Pro
            340                 345                 350
```

```
Lys Pro Lys Asp Thr Leu Met Ile Ser Arg Thr Pro Glu Val Thr Cys
            355                 360                 365
Val Val Val Asp Val Ser His Glu Asp Pro Glu Val Lys Phe Asn Trp
        370                 375                 380
Tyr Val Asp Gly Val Glu Val His Asn Ala Lys Thr Lys Pro Arg Glu
385                 390                 395                 400
Glu Gln Tyr Asn Ser Thr Tyr Arg Val Val Ser Val Leu Thr Val Leu
                405                 410                 415
His Gln Asp Trp Leu Asn Gly Lys Glu Tyr Lys Cys Lys Val Ser Asn
            420                 425                 430
Lys Ala Leu Pro Ala Pro Ile Glu Lys Thr Ile Ser Lys Ala Lys Gly
        435                 440                 445
Gln Pro Arg Glu Pro Gln Val Tyr Thr Leu Pro Pro Ser Arg Asp Glu
    450                 455                 460
Leu Thr Lys Asn Gln Val Ser Leu Thr Cys Leu Val Lys Gly Phe Tyr
465                 470                 475                 480
Pro Ser Asp Ile Ala Val Glu Trp Glu Ser Asn Gly Gln Pro Glu Asn
                485                 490                 495
Asn Tyr Lys Thr Thr Pro Pro Val Leu Asp Ser Asp Gly Ser Phe Phe
            500                 505                 510
Leu Tyr Ser Lys Leu Thr Val Asp Lys Ser Arg Trp Gln Gln Gly Asn
        515                 520                 525
Val Phe Ser Cys Ser Val Met His Glu Ala Leu His Asn His Tyr Thr
    530                 535                 540
Gln Lys Ser Leu Ser Leu Ser Pro Gly Lys
545                 550

<210> SEQ ID NO 20
<211> LENGTH: 1758
<212> TYPE: DNA
<213> ORGANISM: homo sapiens

<400> SEQUENCE: 20
tatccatatg atgttccaga ttatgctggg gcccagccgg ccagatctga gcccaaatct     60
tgtgacaaaa ctcacacatg cccaccgtgc ccagcacctg aactcctggg gggaccgtca    120
gtcttcctct tccccccaaa acccaaggac accctcatga tctcccggac ccctgaggtc    180
acatgcgtgg tggtggacgt gagccacgaa gaccctgagg tcaagttcaa ctggtacgtg    240
gacggcgtgg aggtgcataa tgccaagaca aagccgcggg aggagcagta caacagcacg    300
taccgggtgg tcagcgtcct caccgtcctg caccaggact ggctgaatgg caaggagtac    360
aagtgcaagg tctccaacaa agccctccca gcccccatcg agaaaaccat ctccaaagcc    420
aaagggcagc cccgagaacc acaggtgtac accctgcccc catcccggga tgagctgacc    480
aagaaccagg tcagcctgac ctgcctggtc aaaggcttct atcccagcga catcgccgtg    540
gagtgggaga gcaatgggca gccggagaac aactacaaga ccacgcctcc cgtgctggac    600
tccgacggct ccttcttcct ctacagcaag ctcaccgtgg acaagagcag gtggcagcag    660
gggaacgtct tctcatgctc cgtgatgcat gaggctctgc acaaccacta cacgcagaag    720
agcctctccc tgtctccggg taaagtcgag ggtggaggcg gttcaggcgg aggtggctct    780
ggcggtggcg gatcgttcac cccgcccacc gtgaagatct acagtcgtc ctgcgacggc    840 ggcgggcact ccccccgac catccagctc ctgtgcctcg tctctgggta cacccccagg    900
actatcaaca tcacctggct ggaggacggg caggtcatgg acgtggactt gtccaccgcc    960
```

-continued

```
tctaccacgc aggagggtga gctggcctcc acacaaagcg agctcaccct cagccagaag    1020
cactggctgt cagaccgcac ctacacctgc caggtcacct atcaaggtca cacctttgag    1080
gacagcacca agaagtgtgc agattccaac ccgagagggg tgagcgccta cctaagccgg    1140
cccagcccgt tcgacctgtt catccgcaag tcgcccacga tcacctgtct ggtggtggac    1200
ctggcaccca gcaaggggac cgtgaacctg acctggtccc gggccagtgg gaagcctgtg    1260
aaccactcca ccagaaagga ggagaagcag cgcaatggcc gttaaccgt cacgtccacc     1320 ctgccggtgg caccgaga ctggatcgag ggggagacct accagtgcag ggtgacccac       1380 cccacctgc ccagggccct catgcggtcc acgaccaaga ccagcggccc gcgtgctgcc      1440
ccggaagtct atgcgtttgc gacgccggag tggccgggga ccgggacaa gcgcaccctc     1500 gcctgcctga tccagaactt catgcctgag gacatctcgg tgcagtggct gcacaacgag    1560
gtgcagctcc cggacgcccg gcacagcacg acgcagcccc gcaagaccaa gggctccggc    1620
ttcttcgtct tcagccgtct agaggtgacc agggccgaat gggagcagaa agatgagttc    1680
atctgccgtg cagtccatga ggcagctagc ccctcacaga ccgtccagcg agcggtgtct    1740
gtaaatcccg gtaaatga                                                   1758
```

```
<210> SEQ ID NO 21
<211> LENGTH: 585
<212> TYPE: PRT
<213> ORGANISM: homo sapiens

<400> SEQUENCE: 21
```

```
Tyr Pro Tyr Asp Val Pro Asp Tyr Ala Gly Ala Gln Pro Ala Arg Ser
1               5                   10                  15

Glu Pro Lys Ser Cys Asp Lys Thr His Thr Cys Pro Pro Cys Pro Ala
            20                  25                  30

Pro Glu Leu Leu Gly Gly Pro Ser Val Phe Leu Phe Pro Pro Lys Pro
        35                  40                  45

Lys Asp Thr Leu Met Ile Ser Arg Thr Pro Glu Val Thr Cys Val Val
    50                  55                  60

Val Asp Val Ala His Glu Asp Pro Glu Val Lys Phe Asn Trp Tyr Val
65                  70                  75                  80

Asp Gly Val Glu Val His Asn Ala Lys Thr Lys Pro Arg Glu Glu Gln
                85                  90                  95

Tyr Asn Ser Thr Tyr Arg Val Val Ser Val Leu Thr Val Leu His Gln
            100                 105                 110

Asp Trp Leu Asn Gly Lys Glu Tyr Lys Cys Lys Val Ser Asn Lys Ala
        115                 120                 125

Leu Pro Ala Pro Ile Glu Lys Thr Ile Ser Lys Ala Lys Gly Gln Pro
    130                 135                 140

Arg Glu Pro Gln Val Tyr Thr Leu Pro Pro Ser Arg Asp Glu Leu Thr
145                 150                 155                 160

Lys Asn Gln Val Ser Leu Thr Cys Leu Val Lys Gly Phe Tyr Pro Ser
                165                 170                 175

Asp Ile Ala Val Glu Trp Glu Ser Asn Gly Gln Pro Glu Asn Asn Tyr
            180                 185                 190

Lys Thr Thr Pro Pro Val Leu Asp Ser Asp Gly Ser Phe Phe Leu Tyr
        195                 200                 205

Ser Lys Leu Thr Val Asp Lys Ser Arg Trp Gln Gln Gly Asn Val Phe
    210                 215                 220

Ser Cys Ser Val Met His Glu Ala Leu His Asn His Tyr Thr Gln Lys
```

```
                        225                 230                 235                 240
Ser Leu Ser Leu Ser Pro Gly Lys Val Glu Gly Gly Gly Ser Gly
                245                 250                 255
Gly Gly Gly Ser Gly Gly Gly Ser Phe Thr Pro Thr Val Lys
            260                 265                 270
Ile Leu Gln Ser Ser Cys Asp Gly Gly His Phe Pro Pro Thr Ile
                275                 280                 285
Gln Leu Leu Cys Leu Val Ser Gly Tyr Thr Pro Gly Thr Ile Asn Ile
        290                 295                 300
Thr Trp Leu Glu Asp Gly Gln Val Met Asp Val Asp Leu Ser Thr Ala
305                 310                 315                 320
Ser Thr Thr Gln Glu Gly Glu Leu Ala Ser Thr Gln Ser Glu Leu Thr
                325                 330                 335
Leu Ser Gln Lys His Trp Leu Ser Asp Arg Thr Tyr Thr Cys Gln Val
            340                 345                 350
Thr Tyr Gln Gly His Thr Phe Glu Asp Ser Thr Lys Lys Cys Ala Asp
                355                 360                 365
Ser Asn Pro Arg Gly Val Ser Ala Tyr Leu Ser Arg Pro Ser Pro Phe
        370                 375                 380
Asp Leu Phe Ile Arg Lys Ser Pro Thr Ile Thr Cys Leu Val Val Asp
385                 390                 395                 400
Leu Ala Pro Ser Lys Gly Thr Val Asn Leu Thr Trp Ser Arg Ala Ser
                405                 410                 415
Gly Lys Pro Val Asn His Ser Thr Arg Lys Glu Glu Lys Gln Arg Asn
            420                 425                 430
Gly Thr Leu Thr Val Thr Ser Thr Leu Pro Val Gly Thr Arg Asp Trp
        435                 440                 445
Ile Glu Gly Glu Thr Tyr Gln Cys Arg Val Thr His Pro His Leu Pro
    450                 455                 460
Arg Ala Leu Met Arg Ser Thr Thr Lys Thr Ser Gly Pro Arg Ala Ala
465                 470                 475                 480
Pro Glu Val Tyr Ala Phe Ala Thr Pro Glu Trp Pro Gly Ser Arg Asp
                485                 490                 495
Lys Arg Thr Leu Ala Cys Leu Ile Gln Asn Phe Met Pro Glu Asp Ile
            500                 505                 510
Ser Val Gln Trp Leu His Asn Glu Val Gln Leu Pro Asp Ala Arg His
        515                 520                 525
Ser Thr Thr Gln Pro Arg Lys Thr Lys Gly Ser Gly Phe Phe Val Phe
    530                 535                 540
Ser Arg Leu Glu Val Thr Arg Ala Glu Trp Glu Gln Lys Asp Glu Phe
545                 550                 555                 560
Ile Cys Arg Ala Val His Glu Ala Ala Ser Pro Ser Gln Thr Val Gln
                565                 570                 575
Arg Ala Val Ser Val Asn Pro Gly Lys
            580                 585

<210> SEQ ID NO 22
<211> LENGTH: 1758
<212> TYPE: DNA
<213> ORGANISM: homo sapiens

<400> SEQUENCE: 22
tatccatatg atgttccaga ttatgctggg gcccagccgg ccagatctga gcccaaatct      60
tgtgacaaaa ctcacacatg cccaccgtgc ccagcacctg aactcctggg gggaccgtca     120
```

```
gtcttcctct tccccccaaa acccaaggac accctcatga tctcccggac ccctgaggtc      180
acatgcgtgg tggtggacgt gagcgcggaa gaccctgagg tcaagttcaa ctggtacgtg      240
gacggcgtgg aggtgcataa tgccaagaca agccgcggg aggagcagta caacagcacg       300
taccgggtgg tcagcgtcct caccgtcctg caccaggact ggctgaatgg caaggagtac      360
aagtgcaagg tctccaacaa agccctccca gcccccatcg agaaaaccat ctccaaagcc      420
aaagggcagc cccgagaacc acaggtgtac accctgcccc catcccggga tgagctgacc      480
aagaaccagg tcagcctgac ctgcctggtc aaaggcttct atcccagcga catcgccgtg      540
gagtgggaga gcaatgggca gccggagaac aactacaaga ccacgcctcc cgtgctggac      600
tccgacggct ccttcttcct ctacagcaag ctcaccgtgg acaagagcag gtggcagcag      660
gggaacgtct tctcatgctc cgtgatgcat gaggctctgc acaaccacta cacgcagaag      720
agcctctccc tgtctccggg taaagtcgag ggtggaggcg gttcaggcgg aggtggctct      780
ggcggtggcg gatcgttcac cccgcccacc gtgaagatct acagtcgtc ctgcgacggc       840
ggcgggcact ccccccgac catccagctc ctgtgcctcg tctctgggta caccccaggg       900
actatcaaca tcacctggct ggaggacggg caggtcatgg acgtggactt gtccaccgcc      960
tctaccacgc aggagggtga gctggcctcc acacaaagcg agctcacccT cagccagaag     1020
cactggctgt cagaccgcac ctacacctgc caggtcacct atcaaggtca cccttttgag     1080
gacagcacca gaagtgtgc agattccaac ccgagagggg tgagcgccta cctaagccgg      1140
cccagcccgt tcgacctgtt catccgcaag tcgcccacga tcacctgtct ggtggtggac     1200
ctggcaccca gcaagggga cgtgaacctg acctggtccc gggccagtgg gaagcctgtg     1260
aaccactcca ccagaaagga ggagaagcag cgcaatggca cgttaaccgt cacgtccacc     1320
ctgccggtgg gcacccgaga ctggatcgag ggggagacct accagtgcag ggtgacccac     1380
ccccacctgc ccagggccct catgcggtcc acgaccaaga ccagcggcc gcgtgctgcc     1440
ccggaagtct atgcgtttgc gacgccggag tggccgggga gccgggacaa gcgcaccctc     1500
gcctgcctga tccagaactt catgcctgag gacatctcgg tgcagtggct gcacaacgag     1560
gtgcagctcc cggacgcccg gcacagcacg acgcagcccc gcaagaccaa gggctccggc     1620
ttcttcgtct tcagccgtct agaggtgacc agggccgaat gggagcagaa agatgagttc     1680
atctgccgtg cagtccatga ggcagctagc ccctcacaga ccgtccagcg agcggtgtct     1740
gtaaatcccg gtaaatga                                                   1758
```

<210> SEQ ID NO 23
<211> LENGTH: 585
<212> TYPE: PRT
<213> ORGANISM: homo sapiens

<400> SEQUENCE: 23

Tyr Pro Tyr Asp Val Pro Asp Tyr Ala Gly Ala Gln Pro Ala Arg Ser
1               5                   10                  15

Glu Pro Lys Ser Cys Asp Lys Thr His Thr Cys Pro Pro Cys Pro Ala
            20                  25                  30

Pro Glu Leu Leu Gly Gly Pro Ser Val Phe Leu Phe Pro Pro Lys Pro
        35                  40                  45

Lys Asp Thr Leu Met Ile Ser Arg Thr Pro Glu Val Thr Cys Val Val
    50                  55                  60

Val Asp Val Ser Ala Glu Asp Pro Glu Val Lys Phe Asn Trp Tyr Val
65                  70                  75                  80

```
Asp Gly Val Glu Val His Asn Ala Lys Thr Lys Pro Arg Glu Glu Gln
                85                  90                  95

Tyr Asn Ser Thr Tyr Arg Val Val Ser Val Leu Thr Val Leu His Gln
            100                 105                 110

Asp Trp Leu Asn Gly Lys Glu Tyr Lys Cys Lys Val Ser Asn Lys Ala
        115                 120                 125

Leu Pro Ala Pro Ile Glu Lys Thr Ile Ser Lys Ala Lys Gly Gln Pro
    130                 135                 140

Arg Glu Pro Gln Val Tyr Thr Leu Pro Pro Ser Arg Asp Glu Leu Thr
145                 150                 155                 160

Lys Asn Gln Val Ser Leu Thr Cys Leu Val Lys Gly Phe Tyr Pro Ser
                165                 170                 175

Asp Ile Ala Val Glu Trp Glu Ser Asn Gly Gln Pro Glu Asn Asn Tyr
            180                 185                 190

Lys Thr Thr Pro Pro Val Leu Asp Ser Asp Gly Ser Phe Phe Leu Tyr
        195                 200                 205

Ser Lys Leu Thr Val Asp Lys Ser Arg Trp Gln Gln Gly Asn Val Phe
    210                 215                 220

Ser Cys Ser Val Met His Glu Ala Leu His Asn His Tyr Thr Gln Lys
225                 230                 235                 240

Ser Leu Ser Leu Ser Pro Gly Lys Val Glu Gly Gly Gly Ser Gly
                245                 250                 255

Gly Gly Gly Ser Gly Gly Gly Ser Phe Thr Pro Pro Thr Val Lys
            260                 265                 270

Ile Leu Gln Ser Ser Cys Asp Gly Gly Gly His Phe Pro Pro Thr Ile
    275                 280                 285

Gln Leu Leu Cys Leu Val Ser Gly Tyr Thr Pro Gly Thr Ile Asn Ile
    290                 295                 300

Thr Trp Leu Glu Asp Gly Gln Val Met Asp Val Asp Leu Ser Thr Ala
305                 310                 315                 320

Ser Thr Thr Gln Glu Gly Glu Leu Ala Ser Thr Gln Ser Glu Leu Thr
                325                 330                 335

Leu Ser Gln Lys His Trp Leu Ser Asp Arg Thr Tyr Thr Cys Gln Val
            340                 345                 350

Thr Tyr Gln Gly His Thr Phe Glu Asp Ser Thr Lys Lys Cys Ala Asp
        355                 360                 365

Ser Asn Pro Arg Gly Val Ser Ala Tyr Leu Ser Arg Pro Ser Pro Phe
    370                 375                 380

Asp Leu Phe Ile Arg Lys Ser Pro Thr Ile Thr Cys Leu Val Val Asp
385                 390                 395                 400

Leu Ala Pro Ser Lys Gly Thr Val Asn Leu Thr Trp Ser Arg Ala Ser
                405                 410                 415

Gly Lys Pro Val Asn His Ser Thr Arg Lys Glu Glu Lys Gln Arg Asn
            420                 425                 430

Gly Thr Leu Thr Val Thr Ser Thr Leu Pro Val Gly Thr Arg Asp Trp
        435                 440                 445

Ile Glu Gly Glu Thr Tyr Gln Cys Arg Val Thr His Pro His Leu Pro
    450                 455                 460

Arg Ala Leu Met Arg Ser Thr Thr Lys Thr Ser Gly Pro Arg Ala Ala
465                 470                 475                 480

Pro Glu Val Tyr Ala Phe Ala Thr Pro Glu Trp Pro Gly Ser Arg Asp
                485                 490                 495
```

-continued

```
Lys Arg Thr Leu Ala Cys Leu Ile Gln Asn Phe Met Pro Glu Asp Ile
            500                 505                 510

Ser Val Gln Trp Leu His Asn Glu Val Gln Leu Pro Asp Ala Arg His
        515                 520                 525

Ser Thr Thr Gln Pro Arg Lys Thr Lys Gly Ser Gly Phe Phe Val Phe
    530                 535                 540

Ser Arg Leu Glu Val Thr Arg Ala Glu Trp Glu Gln Lys Asp Glu Phe
545                 550                 555                 560

Ile Cys Arg Ala Val His Glu Ala Ala Ser Pro Ser Gln Thr Val Gln
                565                 570                 575

Arg Ala Val Ser Val Asn Pro Gly Lys
            580                 585
```